US007807678B2

United States Patent
Sharma et al.

(10) Patent No.: US 7,807,678 B2
(45) Date of Patent: *Oct. 5, 2010

(54) PEPTIDOMIMETICS OF BIOLOGICALLY ACTIVE METALLOPEPTIDES

(75) Inventors: Shubh D. Sharma, Cranbury, NJ (US); Yi-Qun Shi, East Brunswick, NJ (US); Zhijun Wu, Plainsboro, NJ (US); Ramesh Rajpurohit, Hillsboro, NJ (US)

(73) Assignee: Palatin Technologies, Inc., Cranbury, NJ (US)

( * ) Notice: Subject to any disclaimer, the term of this patent is extended or adjusted under 35 U.S.C. 154(b) by 1457 days.

This patent is subject to a terminal disclaimer.

(21) Appl. No.: 10/776,419

(22) Filed: Feb. 10, 2004

(65) Prior Publication Data
US 2004/0171520 A1    Sep. 2, 2004

Related U.S. Application Data

(63) Continuation of application No. PCT/US02/25574, filed on Aug. 12, 2002.

(60) Provisional application No. 60/311,404, filed on Aug. 10, 2001.

(51) Int. Cl.
A61K 31/497    (2006.01)
C07D 241/36    (2006.01)
C07D 403/06    (2006.01)
C07D 241/04    (2006.01)
C07D 295/02    (2006.01)

(52) U.S. Cl. .................. 514/252.12; 514/252.13; 514/254.01; 544/349; 544/359; 544/373; 544/385; 544/396

(58) Field of Classification Search .............. 544/349, 544/359, 373, 385, 396; 514/252.12, 252.13, 514/254.01
See application file for complete search history.

(56) References Cited

U.S. PATENT DOCUMENTS

| | | | |
|---|---|---|---|
| 4,148,923 A | 4/1979 | Giudicelli et al. | |
| 4,239,763 A | 12/1980 | Milavec et al. | |
| 4,626,549 A | 12/1986 | Molloy et al. | |
| 4,680,289 A | 7/1987 | Applezweig | |
| 4,711,957 A | 12/1987 | Lai | |
| 4,766,125 A | 8/1988 | Van Daele et al. | |
| 4,937,267 A | 6/1990 | Holloway et al. | |
| 4,938,763 A | 7/1990 | Dunn et al. | |
| 4,943,578 A | 7/1990 | Naylor et al. | |
| 4,968,684 A | 11/1990 | Van Daele et al. | |
| 4,997,836 A | 3/1991 | Sugihara et al. | |
| 5,120,713 A | 6/1992 | Mugica | |
| 5,292,726 A | 3/1994 | Ashton et al. | |
| 5,331,573 A | 7/1994 | Balaji et al. | |
| 5,344,830 A | 9/1994 | Mills et al. | |
| 5,348,955 A | 9/1994 | Greenlee et al. | |
| 5,464,788 A | 11/1995 | Bock et al. | |
| 5,494,919 A | 2/1996 | Morriello et al. | |
| 5,550,131 A | 8/1996 | Suighara et al. | |
| 5,574,031 A | 11/1996 | Abrams et al. | |
| 5,579,250 A | 11/1996 | Balaji et al. | |
| 5,599,809 A | 2/1997 | Hickey et al. | |
| 5,639,778 A | 6/1997 | Andersson et al. | |
| 5,672,602 A | 9/1997 | Burkholder et al. | |
| 5,721,250 A | 2/1998 | Morriello et al. | |
| 5,721,251 A | 2/1998 | Chen et al. | |
| 5,736,539 A | 4/1998 | Graham et al. | |
| 5,753,653 A | 5/1998 | Bender et al. | |
| 5,763,445 A | 6/1998 | Kruse et al. | |
| 5,798,359 A | 8/1998 | Shue et al. | |
| 5,804,578 A | 9/1998 | Chakravarty et al. | |
| 5,856,326 A | 1/1999 | Anthony | |
| 5,872,262 A | 2/1999 | Dolle et al. | |
| 5,877,182 A | 3/1999 | Nargund et al. | |
| 5,880,125 A | 3/1999 | Nargund | |
| 5,880,128 A | 3/1999 | Doll et al. | |
| 5,891,418 A | 4/1999 | Sharma | |
| 5,892,038 A | 4/1999 | Dolle et al. | |

(Continued)

FOREIGN PATENT DOCUMENTS

| | | |
|---|---|---|
| WO | WO 96/38471 | 12/1996 |
| WO | WO 97/46553 | 12/1997 |
| WO | WO 98/10653 | 3/1998 |
| WO | WO 98/17625 | 4/1998 |
| WO | WO 99/55679 | 11/1999 |
| WO | WO 99/58501 | 11/1999 |
| WO | WO 99/64002 | 12/1999 |
| WO | WO 00/01726 | 1/2000 |
| WO | WO 00/05373 | 2/2000 |
| WO | WO 00/17348 | 3/2000 |

(Continued)

OTHER PUBLICATIONS

Jones et al., Current Opinion in Pharmacology, 2003, vol. 3, pp. 530-543.*

(Continued)

*Primary Examiner*—James O Wilson
*Assistant Examiner*—Ebenezer Sackey
(74) *Attorney, Agent, or Firm*—Stephen A. Slusher

(57) ABSTRACT

The invention relates to a method of deriving a peptidomimetic of a biologically active metallopeptide, wherein the peptidomimetic includes at least one non-peptide ring structure defining a template space superimposable on a corresponding defined template space of the metallopeptide, and where the peptidomimetic further includes at least two elements independently including an amino acid residue, amino acid side chain moiety or derivative thereof, the elements defining and occupying a similar descriptor space as corresponding elements of the metallopeptide. The invention further relates to peptidomimetics with a template space heterocyclic ring structure, including 5-, 6- and 8-membered and 5-5- and 6-5-bicyclic fused ring structure melanocortin receptor-specific peptidomimetics.

2 Claims, 5 Drawing Sheets

U.S. PATENT DOCUMENTS

| | | |
|---|---|---|
| 5,936,089 A | 8/1999 | Carpino et al. |
| 5,965,565 A | 10/1999 | Chen et al. |
| 5,968,938 A | 10/1999 | Williams et al. |
| 6,020,334 A | 2/2000 | Fukushi et al. |
| 6,027,711 A | 2/2000 | Sharma |
| 6,033,656 A | 3/2000 | Mikami et al. |
| 6,127,381 A | 10/2000 | Basu et al. |
| 6,127,424 A | 10/2000 | Martin et al. |
| 6,140,354 A | 10/2000 | Dax et al. |
| 6,162,805 A | 12/2000 | Hefti |
| 6,191,117 B1 | 2/2001 | Kozachuk |
| 6,207,665 B1 | 3/2001 | Bauman |
| 6,207,699 B1 | 3/2001 | Rothman |
| 6,214,831 B1 | 4/2001 | Yokoo et al. |
| 6,245,764 B1 | 6/2001 | Kahn et al. |
| 6,284,735 B1 | 9/2001 | Girten et al. |
| 6,294,539 B1 | 9/2001 | Lou et al. |
| 6,303,611 B1 | 10/2001 | Zhang et al. |
| 6,316,470 B1 | 11/2001 | Kover et al. |
| 6,331,285 B1 | 12/2001 | Sharma |
| 6,340,868 B1 | 1/2002 | Lys et al. |
| 6,350,760 B1 | 2/2002 | Bakshi et al. |
| 6,372,747 B1 | 4/2002 | Taveras et al. |
| 6,376,509 B1 | 4/2002 | Bakshi et al. |
| 6,410,548 B2 | 6/2002 | Nargund et al. |
| 6,432,438 B1 | 8/2002 | Shukla |
| 6,432,959 B1 | 8/2002 | Cooper et al. |
| 6,451,783 B1 | 9/2002 | Cooper et al. |
| 6,458,789 B1 | 10/2002 | Forood et al. |
| 6,458,790 B2 | 10/2002 | Palucki et al. |
| 6,469,006 B1 | 10/2002 | Blair et al. |
| 6,472,398 B1 | 10/2002 | Palucki et al. |
| 6,486,165 B2 | 11/2002 | Zhand et al. |
| 6,515,122 B1 | 2/2003 | Lang et al. |
| 6,531,476 B1 | 3/2003 | Heymans et al. |
| 6,534,503 B1 | 3/2003 | Dines et al. |
| 6,534,509 B1 | 3/2003 | Bauman et al. |
| 6,555,537 B2 | 4/2003 | Bauman et al. |
| 6,569,861 B2 | 5/2003 | Bakthavatchalam et al. |
| 6,579,968 B1 | 6/2003 | Blood et al. |
| 6,612,805 B2 | 9/2003 | Rietsch |
| 6,648,848 B1 | 11/2003 | Keldmann et al. |
| 6,673,767 B1 | 1/2004 | Brodbeck et al. |
| 6,699,873 B1 | 3/2004 | Maguire et al. |
| 6,715,485 B1 | 4/2004 | Djupesland |
| 6,734,175 B2 | 5/2004 | Hadcock et al. |
| 6,811,543 B2 | 11/2004 | Keldmann et al. |
| 6,949,552 B2 | 9/2005 | Nakazato et al. |
| 7,326,707 B2 | 2/2008 | Sharma et al. |
| 7,354,923 B2 * | 4/2008 | Sharma et al. ......... 514/252.13 |
| 7,456,184 B2 | 11/2008 | Sharma et al. |
| 2001/0018075 A1 | 8/2001 | Shigeyuki et al. |
| 2001/0047001 A1 | 11/2001 | Varkhedkar et al. |
| 2002/0004512 A1 | 1/2002 | Bakshi et al. |
| 2002/0010182 A1 | 1/2002 | Masaaki |
| 2002/0019523 A1 | 2/2002 | Palucki et al. |
| 2002/0022620 A1 | 2/2002 | Kahn et al. |
| 2002/0032238 A1 | 3/2002 | Priepke et al. |
| 2002/0037837 A1 | 3/2002 | Takeda et al. |
| 2002/0042399 A1 | 4/2002 | Kruse et al. |
| 2002/0052383 A1 | 5/2002 | Bakthavatchalam et al. |
| 2002/0065277 A1 | 5/2002 | Hadcock et al. |
| 2002/0065416 A1 | 5/2002 | Stasiak et al. |
| 2002/0072604 A1 | 6/2002 | Carpino et al. |
| 2002/0082263 A1 | 6/2002 | Lou et al. |
| 2002/0107253 A1 | 8/2002 | Koh et al. |
| 2002/0107255 A1 | 8/2002 | Blumberg et al. |
| 2002/0128247 A1 | 9/2002 | Dow et al. |
| 2002/0128270 A1 | 9/2002 | Neya et al. |
| 2002/0137664 A1 | 9/2002 | Bakshi et al. |
| 2002/0143141 A1 | 10/2002 | Chen et al. |
| 2002/0173512 A1 | 11/2002 | Moltzen et al. |
| 2002/0177598 A1 | 11/2002 | Baumann |
| 2002/0183316 A1 | 12/2002 | Pan |
| 2003/0004162 A1 | 1/2003 | Treadway |
| 2003/0013721 A1 | 1/2003 | Meghaui et al. |
| 2003/0040520 A1 | 2/2003 | Guzi et al. |
| 2003/0055008 A1 | 3/2003 | Morcotte |
| 2003/0055009 A1 | 3/2003 | Steiner et al. |
| 2003/0055247 A1 | 3/2003 | Cosford et al. |
| 2003/0055265 A1 | 3/2003 | Binggeli et al. |
| 2003/0060473 A1 | 3/2003 | Neya et al. |
| 2003/0064921 A1 | 4/2003 | Millhauser et al. |
| 2003/0069169 A1 | 4/2003 | Macor et al. |
| 2003/0083228 A1 | 5/2003 | Carpino et al. |
| 2003/0083335 A1 | 5/2003 | Hayward |
| 2003/0092732 A1 | 5/2003 | Yu et al. |
| 2003/0096827 A1 | 5/2003 | Yu et al. |
| 2003/0105106 A1 | 6/2003 | Chiang et al. |
| 2003/0109556 A1 | 6/2003 | Mazur et al. |
| 2003/0125334 A1 | 7/2003 | Chiang et al. |
| 2003/0139425 A1 | 7/2003 | Bauman et al. |
| 2003/0144277 A1 | 7/2003 | DeLucca |
| 2003/0149019 A1 | 8/2003 | Bremberg et al. |
| 2003/0158205 A1 | 8/2003 | Bauman et al. |
| 2003/0158209 A1 | 8/2003 | Dyck et al. |
| 2003/0162819 A1 | 8/2003 | Eisinger et al. |
| 2003/0166637 A1 | 9/2003 | Lehmann-Lintz et al. |
| 2003/0176425 A1 | 9/2003 | Eisinger et al. |
| 2003/0181441 A1 | 9/2003 | McClure et al. |
| 2003/0191136 A1 | 10/2003 | Bakthavatchalam et al. |
| 2003/0195212 A1 | 10/2003 | Lundstedt et al. |
| 2004/0006067 A1 | 1/2004 | Fotsch et al. |
| 2004/0024211 A1 | 2/2004 | Boyce et al. |
| 2004/0034034 A1 | 2/2004 | Blumberg et al. |
| 2004/0053933 A1 | 3/2004 | Pontillo et al. |
| 2004/0147567 A1 | 7/2004 | Nakazato et al. |
| 2004/0152534 A1 | 8/2004 | Chapman et al. |
| 2004/0157264 A1 | 8/2004 | Sharma et al. |
| 2004/0171520 A1 | 9/2004 | Sharma et al. |
| 2004/0204398 A1 | 10/2004 | Bakshi et al. |
| 2004/0224957 A1 | 11/2004 | Sharma et al. |
| 2004/0254198 A1 | 12/2004 | Reynolds et al. |
| 2005/0124636 A1 | 6/2005 | Sharma et al. |
| 2005/0130988 A1 | 6/2005 | Sharma et al. |
| 2005/0176728 A1 | 8/2005 | Sharma et al. |
| 2006/0009456 A1 | 1/2006 | Hutchinson et al. |
| 2006/0084657 A1 | 4/2006 | Nakazato et al. |
| 2006/0287330 A1 | 12/2006 | Sharma et al. |
| 2006/0287331 A1 | 12/2006 | Sharma et al. |
| 2006/0287332 A1 | 12/2006 | Sharma et al. |
| 2008/0070921 A1 | 3/2008 | Burris et al. |
| 2008/0234289 A1 | 9/2008 | Sharma et al. |
| 2009/0076029 A1 | 3/2009 | Sharma et al. |

FOREIGN PATENT DOCUMENTS

| | | |
|---|---|---|
| WO | WO 00/35952 | 6/2000 |
| WO | WO 00/36136 | 6/2000 |
| WO | WO 00/40247 | 7/2000 |
| WO | WO 00/53148 | 9/2000 |
| WO | WO 00/68185 | 11/2000 |
| WO | WO 00/74679 | 12/2000 |
| WO | WO 01/05401 | 1/2001 |
| WO | WO 01/10842 | 2/2001 |
| WO | WO 01/12176 | 2/2001 |
| WO | WO 01/13112 | 2/2001 |
| WO | WO 01/18210 | 3/2001 |
| WO | WO 01/21634 | 3/2001 |
| WO | WO 01/21647 | 3/2001 |
| WO | WO 01/23392 | 4/2001 |
| WO | WO 01/30343 | 5/2001 |
| WO | WO 01/30808 | 5/2001 |
| WO | WO 01/35970 | 5/2001 |

| | | |
|---|---|---|
| WO | WO 01/52880 | 7/2001 |
| WO | WO 01/55106 | 8/2001 |
| WO | WO 01/55107 | 8/2001 |
| WO | WO 01/55109 | 8/2001 |
| WO | WO 01/70708 | 9/2001 |
| WO | WO 01/91752 | 12/2001 |
| WO | WO 02/00259 | 1/2002 |
| WO | WO 02/00654 | 1/2002 |
| WO | WO 02/12178 | 2/2002 |
| WO | WO 02/15909 | 2/2002 |
| WO | WO 02/18437 | 3/2002 |
| WO | WO 02/47670 | 6/2002 |
| WO | WO 02/059095 | 8/2002 |
| WO | WO 02/059107 | 8/2002 |
| WO | WO 02/059108 | 8/2002 |
| WO | WO 02/059117 | 8/2002 |
| WO | WO 02/062766 | 8/2002 |
| WO | WO 02/064091 | 8/2002 |
| WO | WO 02/064734 | 8/2002 |
| WO | WO 02/067869 | 9/2002 |
| WO | WO 02/068387 | 9/2002 |
| WO | WO 02/068388 | 9/2002 |
| WO | WO 02/069905 | 9/2002 |
| WO | WO 02/070511 | 9/2002 |
| WO | WO 02/079146 | 10/2002 |
| WO | WO 02/079203 | 10/2002 |
| WO | WO 02/079753 | 10/2002 |
| WO | WO 02/081443 | 10/2002 |
| WO | WO 02/085925 * | 10/2002 |
| WO | WO 02/092566 | 11/2002 |
| WO | WO 03/006620 | 1/2003 |
| WO | WO 03/007949 | 1/2003 |
| WO | WO 03/009847 | 2/2003 |
| WO | WO 03/009850 | 2/2003 |
| WO | WO 03/013509 | 2/2003 |
| WO | WO 03/013571 | 2/2003 |
| WO | WO 03/020724 | 3/2003 |
| WO | WO 03/027239 | 4/2003 |
| WO | WO 03/031410 | 4/2003 |
| WO | WO 03/045920 | 6/2003 |
| WO | WO 03/053927 | 7/2003 |
| WO | WO 03/055477 | 7/2003 |
| WO | WO 03/061660 | 7/2003 |
| WO | WO 03/066587 | 8/2003 |
| WO | WO 03/066597 | 8/2003 |
| WO | WO 03/072056 | 9/2003 |
| WO | WO 03/092690 | 11/2003 |
| WO | WO 03/093234 | 11/2003 |
| WO | WO 03/094918 | 11/2003 |
| WO | WO 2004/037796 | 5/2004 |
| WO | WO 2005/102340 | 11/2005 |
| WO | WO 2006/014552 | 2/2006 |
| WO | WO 2007/021990 | 2/2007 |
| WO | WO 2007/021991 | 2/2007 |

OTHER PUBLICATIONS

Sudoh et al., Pharmaceutical Res., vol. 15, No. 5, 1998, pp. 719-725.*
Alterman et al., J. Med. Chem., 1998, vol. 41, pp. 3782-3792.*
Fan et al., 1997, Role of melanocortinergic neurons in feeding and the agouti obesity syndrome, Nature, 385(9): 165-168.*
Hruby et al., 1997, Current Opinion in Chemical Biology, 1: 114-119.*
Holder et al., 2004, Medicinal Research Reviews, 24(3): 325-356.*
Jones et al., 2003, Current Opinion in Pharmacology, 3: 530-543.*
Dimaio et al. Synthesis of Chiral Piperazin-2-ones as Model Peptidomimetics. J. Chem. Soc. Perkin Trans. I, 1989, pp. 1687-1689.
Cornille et al. Anodic Amide Oxidations: Conformationally Restricted Peptide Building Blocks from the Direct Oxidation of Dipeptides. Tet. Letters, 1994, vol. 35, No. 38, pp. 6989-6992.
Moore et al. A Rapid Screening System to Determine Drug Affinities for the Intestinal Dipeptide Transporter 2: Affinities of ACE Inhibitors. Int. J. Pharmaceutics, 2000, vol. 210, pp. 29-44.
Hruby et al. Molecular Organization of Receptors. Ann. NY Accd. Sci. 1995, vol. 757, pp. 7-22.
"Synthetic Peptides: A User's Guide", GA Grant, editor, W.H. Freeman & Co., New York, 1992 (pp. 11-24).
Hruby, V J, Al-Obeidi F and Kazmierski, W.: Biochemistry Journal 268: 249-262 (1990).
Toniolo, C., International Journal Peptide Protein Research 35: 287-300, (1990).
U.S. Appl. No. 11/110,060, filed Apr. 19, 2005, Sharma et al.
U.S. Appl. No. 12/130,299, filed May 30, 2008, Burris et al.
U.S. Appl. No. 12/130,316, filed May 30, 2008, Sharma et al.
Abou-Gharbia et al. "Synthesis and SAR of Adatanserin: Novel Adamantyl Aryl- and Heteroarylpiperazines with Dual Serotonin $5-HT_{1A}$ and $5-HT_2$ Activity as Potential Anxiolytic and Antidepressant Agents" J. Med. Chem. 42(25):5077-5094 (1999).
Adan et al. "Identification of antagonists for melanocortin MC3, MC4 and MC5 receptors" Eur. J. Pharmacol. 269(3):331-337 (1994).
Adan et al. "Inverse agonism gains weight" Trends in Pharmacological Sciences 24(6):315-321 (2003).
Baldwin et al. "Synthesis of a bicyclic γ-lactam dipeptide analogue" Tetrahedron Letters 34(10):1665-1668 (1993).
Chang et al. "Morphiceptin (NH4-tyr-pro-phe-pro-COHN2): a potent and specific agonist for morphine (mu) receptors" Science 212(4490):75-77 (1981).
Cho et al. "Discovery of novel, potent and orally active nonpeptide antagonist of the human luteinizing hormone-releasing hormone (LHRH) receptor" J. Med. Chem. 41:4190-4195 (1998).
Chorev et al. "Toward nonpeptidal substance P mimetic analogues: Design, synthesis, and biological activity" Biopolymers 31(6):725-733 (1991).
Dorr et al. "Evaluation of melanotan-II, a superpotent cyclic melanotropic peptide in a pilot phase-I clinical study" Life Science 58(20):1777-1784 (1996).
Gante "Peptidomimetics—Tailored enzyme-inhibitors" Angewandte Chemie International Edition in English 33(17):1699-1720 (1994).
Giannis et al. "Peptidomimetics in drug design" Advances in Drug Research 29:1-78 (1997).
Hadley et al. "Discovery and development of novel melanogenic drugs. Melanotan-I and -II" Ronald. T. Borchardt, et al. editors; Integration of Pharmaceutical Discovery and Development: Case Histories, Plenum Press, New York, 575-595 (1998).
Haskell-Luevano et al. "Discovery of Prototype Peptidomimetic Agonists at the Human Melanocortin Receptors MC1R and MC4R" J. Med. Chem. 40:2133-2139 (1997).
Kask et al. "Discovery of a novel superpotent and selective melanocortin-4 receptor antagonist (HS024): Evaluation in vitro and in vivo" Endocrinology 139(12):5006-5014 (1998).
Kim et al. "Synthesis of (3R)-carboxy pyrrolidine (a β-proline analogue) and its oligomer" Bioorganic & Medicinal Chemistry Letters 10(21):2417-2419 (2000).
Klein et al. "O-benzyl hydroxyproline as a bioisostere for Phe-Pro: Novel dipeptide thrombin inhibitors" Bioorganic & Medicinal Chemistry Letters 6(18):2225-2230 (1996).
Lerner et al. "Synthetic melanocortin receptor. Agonist and antagonists" Cutaneous Neuroimmunomodulation: The Proopiomelanocortin System, Annals of the New York Academy of Sciences 885:153-160 (1995).
Medical Encyclopaedia: Female sexual dysfunction [online]. Retrieved on Oct. 10, 2007 from http://www.nlm.nih.gov/medlineplus/ency/article/003159.htm.
Mitsunobu "The use of diethyl azodicarboxylate and triphenylphosphine in synthesis and transfromation of natural products" Synthesis 1:1-28 (1981).
Moore et al. "Designing Peptide Mimetics" Trends Pharmacol. Sci. 15:124-129 (1994).
Rarey et al. "Similarity searching in large combinatorial chemistry spaces" J. Computer-Aided Mol. Des. 15(6):497-520 (2001).
Rubsam et al. "Synthesis of chiral piperazinones as versatile scaffolds for peptidomimetics" Tetrahedron 56(43):8481-8487 (2000).

Sasaki et al. "Discovery of a thieno[2,3-d]pyrimidine-2,4-dione bearing a p-methoxyureidophenyl moiety at the 6-position: A highly potent and orally bioavailable non-peptide antagonist for the human luteinizing hormone-releasing hormone receptor" J. Med. Chem. 46:113-124 (2003).

Schioth et al. "Pharmacological comparison of rat and human melanocortin 3 and 4 receptors in vitro" Regulatory Peptides 106:7-12 (2002).

Shvachkin et al. "Synthesis of analogs of the thyrotropin-releasing hormone" Journal of General Chemistry of the USSR in English Translation 43(3):686-687 (1973).

Stavropoulos et al. "Synthesis of cis-4-hydroxy-L-proline and its incorporation into biologically important peptides" Review of Clinical Pharmacology and Pharmacokinetics 103-106 (1995).

Takenaka et al. "Synthesis of met- and leu-enkephalin analogues containing chiral N,N-ethylene-bridged phenylalanyl-methionine and -leucine" J Chem. Soc., Perkin Trans I, 8:933-937 (1993).

Torres et al. "Neoglycopeptide synthesis and purification in multigram scale: preparation of O-(2,3,4,6-tetra-O-acetyl-beta-D-galactopyranosyl)-N alpha-fluoren-9-yl-methoxycarbonyl-hydroxyproline and its use in the pilot-scale synthesis of the potent analgesic glycopeptide O1.5-beta-D-galactopyranosyl [DMet2, Hyp5]enkephalinamide." Journal of Peptide Science 3(2):99-109 (1997).

Torres et al. "Synthesis and conformational analysis of a series of galactosyl enkephalin analogues showing high analgesic activity" The EMBO Journal 8(10):2925-2932 (1989).

Yamamoto "Synthesis and adhesive studies of marine polypeptides" J. Chem. Soc., Perkin Trans I, 3:613-618 (1987).

Zhorov et al. "Similarity of Ca2+-bound conformations of morphine and Met-enkephalin: A computational study" FEBS Letters 354(2):131-134 (1994).

Cachexia [online], retrieved on Nov. 19, 2009 from the internet (URL: http://en.wikipedia.org/wiki/Cachexia).

Inui "Cancer anorexia-cachexia syndrome: Current issues in research and management" CA A Cancer Journal for Clinicians 52:72-91 (2002).

Fan et al. "Role of melanocortinergic neurons in feeding and the agouti obesity syndrome" Nature 385(6612):165-168 (1997).

Holder et al. "Melanocortin ligands: 30 years of structure-activity relationship (SAR) studies" Medicinal Research Reviews 24(3): 325-356 (2004).

Hruby et al. "Synthesis of oligopeptide and peptidomimetic libraries" Current Opinion in Chemical Biology 1(1): 114-119 (1997).

* cited by examiner

PEPTIDOMIMETICS OF BIOLOGICALLY ACTIVE METALLOPEPTIDES

CROSS-REFERENCE TO RELATED APPLICATION

This application is a continuation application of International Application No. PCT/US02/25574, International Publication No. WO 03/013571, entitled "Peptidomimetics of Biologically Active Metallopeptides", filed on Aug. 12, 2002, which claimed the benefit of the filing of U.S. Provisional Patent Application Serial No. 60/311,404, entitled "Receptor-Specific Peptides Derived from Biologically Active Metallopeptides", filed on Aug. 10, 2001, and the specification thereof of each is incorporated herein by reference.

BACKGROUND OF THE INVENTION

1. Field of the Invention (Technical Field)

The present invention relates to peptidomimetics that bind to a target of interest and are agonists, antagonists or mixed agonist-antagonists, and more particularly to peptidomimetics derived from biologically active metallopeptides, including peptidomimetics specific for one or more melanocortin receptors.

2. Background Art

Note that the following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

Metallopeptides. Specific metallopeptides and methods for making and using receptor-specific metallopeptides are generally disclosed in International Patent Application Serial No. PCT/US02/04431, entitled Melanocortin Metallopeptides for Treatment of Sexual Dysfunction, filed Feb. 13, 2002; International Patent Application Serial No. PCT/US01/50075, entitled Identification of Target-Specific Folding Sites in Peptides and Proteins, filed Dec. 19, 2001; International Patent Application Serial No. PCT/US00/16396, entitled Melanocortin Metallopeptide Constructs, Combinational Libraries and Applications, filed Jun. 14, 2000; International Patent Application Serial No. PCT/US99/29743, entitled Metallopeptide Combinatorial Libraries and Applications, filed Dec. 14, 1999; U.S. Pat. No. 6,027,711 entitled Structurally Determined Metallo-Constructs and Applications, issued Feb. 22, 2000; U.S. Pat. No. 6,331,285 entitled Structurally Determined Cyclic Metallo-Constructs and Applications, issued Dec. 18, 2001; and U.S. Pat. No. 5,891,418, entitled Peptide—Metal Ion Pharmaceutical Constructs and Applications, issued Apr. 6, 1999, and the specifications thereof of each are incorporated herein by reference. In summary, the foregoing patents and applications teach metallopeptide compositions and methods of making and using metallopeptides, which metallopeptides are mimics of turn structures, bind to receptors of interest, and are agonists, antagonists, or mixed agonist-antagonists. In one simplified embodiment, an amino acid sequence provides an $N_3S_1$ ligand for a tetradentate metal ion such as rhenium (Re). The tri-peptide metal ion binding sequence can include amino acids in the L- or D-configuration, which may further have modified or unnatural side chains. The metallopeptides can include one or more amino acid residues, mimetics or other structures at either or both ends, and any terminal or capping group. Such a metallopeptide has the following general structure:

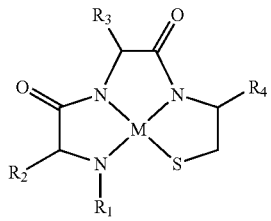

where $R_1$ and $R_4$ are the same or different and are independently selected from any terminal or capping group and optionally any one or more natural or unnatural L- or D-amino acid residues; $R_2$ and $R_3$ are the same or different and independently selected from any amino acid side chain moiety or derivative thereof; and M is a metal ion, such as Re.

It is known that linear peptides have high rotational degrees of freedom, such that for even small peptides with known primary structures the theoretically possible secondary and tertiary structures may number in the millions. In general cyclic peptides are more constrained, and at least small cyclic peptides have far fewer theoretically possible secondary and tertiary structures. However, even with cyclic peptides it is frequently impossible to predict with precision the actual secondary structures present in such peptide. By contrast, metallopeptides as described above have well-defined and limited secondary structures, with the residues involved in metal ion complexation forming a turn structure about the metal ion. The atoms forming a part of the coordination sphere of the metal ion are fixed by the coordination geometry of the metal ion. This, coupled with the peptide bonds between residues and the side chain bonds, yields a conformationally fixed and predictable secondary structure for at least the residues involved in metal ion complexation.

Peptide and Protein Folding. Determination of the biologically relevant structure of proteins and peptides, which can be characterized as a functional three-dimensional structure, is a difficult problem in the biological, biochemical and pharmaceutical sciences. Through use of any of a variety of methods the primary structure of relevant peptides or proteins may be ascertained. That is, the sequence of amino acid residues composing the peptide or protein is known, and it is known that the peptide or protein has a desired biological effect, such as binding a target molecule or receptor of interest, mediating a biological activity of interest, or the like. However, both the three-dimensional structure and sequence of the portion of the peptide or protein forming a ligand and thereby giving rise to the desired biological effect is unknown.

Peptides and proteins are highly flexible, due in large part to amino group and carboxyl group bonds of individual amino acid residues having a high rotational degree of freedom. In addition, some bonds in side chains of individual amino acid residues also have rotational degrees of freedom. The non-bonded steric interactions between amino acid residues force the peptide or protein along its degrees of freedom into some stable minimal free energy configuration. Local structures, also known as the "secondary structure," are common in peptides and proteins. These structures include α-helixes, β-bends, sheets, extended chains, loops and the like, and most often contribute to binding or receptor specificity of peptides and proteins.

There are several types of α-helixes known, differing in torsion angles within the amino acid residues of the actual turn and by the patterns of intra- and inter-molecular hydrogen bonding. There are also a number of known different β-bends, differing in the dihedral torsion angles ψ (for the $C^α$—C bond) or Φ (for the $C^α$—N bond), or both.

Generation of structure-based pharmacophores, utilizing experimental methods such as X-ray crystallography or NMR, optionally in conjunction with protein structure determination methods, such as homology modeling, is known in the art. However, in order for this approach to be employed it must be possible to obtain appropriate data from the ligand in the conformation specific for the receptor defining the pharmacophore. This is not feasible in many instances.

A number of mimetics of various turn structures are known in the art. For example, WO 00/68185, entitled A Structure-Based Approach to Design Inhibitors of Protein-Processivity Factor Interactions, discloses peptidomimetics that mimic helical portions of certain proteins. U.S. Pat. No. 6,245,764, β-Sheet Mimetics and use Thereof as Inhibitors of Biologically Active Peptides or Proteins, discloses certain β-sheet mimetics, particularly serine protease inhibitor mimetics. Two published patent applications by common inventors, U.S. Application No. 2002/0022620 A1 and 2002/0065416 A1, both entitled Reverse-Peptidomimetics and Methods Relating Thereto, disclose specific compounds for use in cell adhesion-indicated diseases and as anti-inflammatory agents, respectively. However, none of these patents or applications discloses a method for determining the formula or three-dimensional configuration of peptidomimetics for particular initial compounds, such as metallopeptides.

Melanocortin Receptors. A family of melanocortin receptor types and subtypes have been identified, including melanocortin-1 receptors (MC1-R) expressed on normal human melanocytes and melanoma cells, melanocortin-2 receptors (MC2-R) for ACTH (adrenocorticotropin) expressed in cells of the adrenal gland, melanocortin-3 and melanocortin-4 receptors (MC3-R and MC4-R) expressed primarily in cells in the hypothalamus, mid-brain and brainstem, and melanocortin-5 receptors (MC5-R), expressed in a wide distribution of peripheral tissues.

In general, compounds specific for MC1-R are believed to be useful for treatment of melanoma, including use as radiotherapeutic or drug delivery agent, and as diagnostic imaging agents, particularly when labeled with a diagnostic radionisotope. Compounds specific for MC3-R, MC4-R or MC5-R are believed to be useful in regulation of energy homeostasis, including use as agents for attenuating food intake and body weight gain, for use in treatment of anorexia, as a weight gain aid, for treatment of obesity, and other treatment of other food intake and metabolism-related purposes. Compounds specific for MC3-R and MC4-R, among other melanocortin receptors, can be used as agents for treatment of sexual dysfunction, including male erectile dysfunction. Compounds specific for MC3-R and MC4-R, among other melanocortin receptors, can be used to regulate blood pressure, heart rate and other neurophysiologic parameters. Other melanocortin receptor-specific compounds, such as MCR-1 agonists, can be used as tanning agents to increase melanin production. Compounds specific for MCR-1 and MCR-3 may be useful in regulation of inflammatory processes.

There is a significant need for compounds with high specificity for discrete melanocortin receptors, as well as compounds that are either agonists or antagonists for specific melanocortin receptors. High affinity compounds for melanocortin receptors can be used to exploit varied physiological responses associated with the melanocortin receptors, either as agonists or antagonists. In addition, melanocortin receptors have an effect on the activity of various cytokines, and high affinity compounds for melanocortin receptors can be used to regulate cytokine activity.

SUMMARY OF THE INVENTION

Disclosure of the Invention

In one embodiment the invention provides a method of deriving a peptidomimetic of a biologically active metallopeptide. In the practice of this method a biologically active metallopeptide is selected, which metallopeptide includes at least a peptide sequence with a metal ion complexed thereto, wherein biological activity is related to at least two elements of such metallopeptide, the at least two elements independently comprising an amino acid residue, amino acid side chain moiety or derivative thereof, and wherein the metal ion is complexed to at least three atoms in the peptide sequence, such at least three atoms being part of at least two amino acid residues comprising the peptide sequence, whereby such at least three atoms and the metal ion form a ring structure including at least one ring, the at least one ring of the ring structure defining a template space. A non-peptidic ring structure that is superimposable on the template space defined by at least one ring of the ring structure of the biologically active metallopeptide is then modeled, and a peptidomimetic formed by adding to the non-peptidic ring structure at least two elements independently including an amino acid residue, amino acid side chain moiety or derivative thereof, such at least two elements occupying a similar descriptor space as corresponding elements of the biologically active metallopeptide.

In the practice of this method, the biological activity of the peptidomimetic can be compared to that of the biologically active metallopeptide. Comparing the biological activity of the peptidomimetic to that of the biologically active metallopeptide can include comparison to the biological activity of a third compound, or alternatively screening for binding to a defined target of interest. Screening can include competing a known binding partner for binding to the target of interest with the peptidomimetic. Assays employed include functional assays, including comparing the biological activity of the peptidomimetic to that of the biologically active metallopeptide such as by utilizing a biological receptor capable of transmitting a signal and determining whether the peptidomimetic induces or inhibits transmission of the signal. The biologically active metallopeptide may be an agonist or antagonist. Representative examples include biologically active metallopeptides specific for one or more melanocortin, angiotensin, vasopressin or oxytocin receptors.

The metallopeptide includes compositions wherein the metal ion is a tetradentate metal ion and the metal ion is complexed to four atoms in the peptide sequence. In one embodiment, the at least four atoms constitute an $N_3S_1$ ligand. In another embodiment, the at least four atoms constitute an $N_2S_2$ ligand. In a preferred embodiment at least one amino acid residue of the at least two amino acids residues of the biologically active metallopeptide to which the metal ion is complexed is an L- or D-3-mercapto amino acid. Such L- or D-3-mercapto amino acid include L- or D-cysteine, L- or D-penicillamine, 3-mercapto phenylalanine, or a homologue of any of the foregoing. The metal ion may be an ion of V, Mn, Fe, Co, Ni, Cu, Zn, Ga, As, Se, Y, Mo, Tc, Ru, Rh, Pd, Ag, Cd, In, Sn, W, Re, Os, Ir, Pt, Au, Hg, Tl, Pb, Bi, Po, At, Sm, Eu or Gd.

In a preferred embodiment the biologically active metallopeptide binds to a target of interest. This target of interest may be a receptor, antibody, toxin, enzyme, hormone, nucleic acid, intracellular protein domain of biological relevance or extracellular protein domain of biological relevance.

The template space of the metallopeptide can be defined by fewer than all rings comprising the ring structure of the biologically active metallopeptide. This include embodiments wherein the ring structure of the biologically active metallopeptide is a tricyclic ring structure. In this event, the template space may be defined by one ring of the tricyclic ring structure or alternatively defined by two rings of the tricyclic ring structure. The defined template space of the biologically active metallopeptide is defined, at least in part, by the coordination geometry of the metal ion In the method the at least two elements independently derived from an amino acid residue or amino acid side chain moiety of the biologically active metallopeptide can include a naturally occurring amino acid, a synthetic amino acid, a modified amino acid, a side chain of an a naturally occurring amino acid, a side chain of a synthetic amino acid, a side chain of a modified amino acid, a derivative of a side chain of a naturally occurring, synthetic or modified amino acid or a mimetic of any of the foregoing.

The non-peptidic ring structure can include a 5-, 6-, 7-, or 8-membered ring, a 5-5-, 5-6-, 5-7-, 5-8-, 6-6-, 6-7-, 6-8-, 7-7-, 7-8-, or 8-8-fused bicyclic ring, or a 5-5-5-, 5-5-6- or 5-6-6-fused tricyclic ring. In instance in which the ring structure is a bicyclic or tricyclic ring structure at least one ring of the ring structure is superimposable on the template space defined by at least one ring of the ring structure of the biologically active metallopeptide.

In this method, the peptidomimetic can be of the formula:

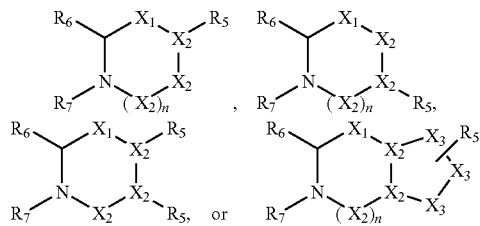

wherein
$X_1$ is $(CH_2)_m$ or $X_3$;
$X_2$ is independently $CH_2$, CH, NH or N;
$X_3$ is independently $(CH_2)_n$, CH, NH, N, O, C=O, C=S, S, S=O, or $SO_2$;
$R_5$ is any moiety other than H;
$R_6$ is an amino acid side chain moiety or derivative thereof;
$R_7$ is one or more amino acid residues or derivatives thereof and optionally a terminal group moiety, or is an amino acid side chain moiety or derivative thereof;
$R_7$ and at least one of $R_6$ or $R_5$ each constitute an element occupying a similar descriptor space as corresponding elements of the biologically active metallopeptide;
n is 0, 1, 2 or 3; and
m is 0 or 1;
provided that any two adjacent CH groups, adjacent NH and CH groups or adjacent NH groups may optionally form a double bond.

The invention further includes peptidomimetics made by the foregoing method.

In another embodiment the invention provides a peptidomimetic including a template space that is defined by a ring structure that is 5-, 6-, 7-, or 8-membered, 5-5-, 5-6-, 5-7-, 5-8-, 6-6-, 6-7-, 6-8-, 7-7-, 7-8-, or 8-8-fused bicyclic, or 5-5-5-, 5-5-6- or 5-6-6-fused tricyclic ring structure, and at least two descriptor spaces including elements that are amino acid side chain moieties or derivatives thereof joined by covalent bonds to the ring structure, wherein the descriptor spaces occupy a similar descriptor space as descriptor spaces defined by corresponding elements that are amino acid side chain moieties or derivatives thereof of a metallopeptide that binds to the same receptor as the peptidomimetic. In this embodiment, the peptidomimetic may be of the foregoing formula.

In another embodiment, the invention provides a biologically active peptidomimetic including the structure $X_1$-$X_2$-$X_3$, wherein $X_1$ and $X_3$ comprise an amino acid side chain or mimetic thereof and $X_2$ comprises a ring structure. In this embodiment, $X_2$ can be a 5-, 6-, 7-, or 8-membered ring, a 5-5-, 5-6-, 5-7-, 5-8-, 6-6-, 6-7-, 6-8-, 7-7-, 7-8-, or 8-8-fused bicyclic ring, or a 5-5-5-, 5-5-6- or 5-6-6-fused tricyclic ring. The selection of $X_1$ and $X_3$ and the position and orientation of $X_1$ and $X_3$ relative to $X_2$ can be derived from a biologically active metallopeptide.

In another embodiment, the invention provides peptidomimetics of the formula:

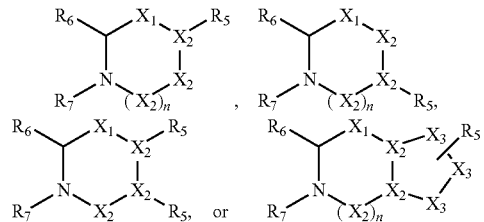

wherein
$X_1$ is $(CH_2)_m$ or $X_3$;
$X_2$ is independently $CH_2$, CH, NH or N;
$X_3$ is independently $(CH_2)_n$, CH, NH, N, O, C=O, C=S, S, S=O, or $SO_2$;
$R_5$ is any moiety other than H;
$R_6$ is an amino acid side chain moiety or derivative thereof;
$R_7$ is one or more amino acid residues or derivatives thereof and optionally a terminal group moiety, or is an amino acid side chain moiety or derivative thereof;
n is 0, 1, 2 or 3; and
m is 0 or 1;
provided that any two adjacent CH groups, adjacent NH and CH groups or adjacent NH groups may optionally form a double bond.

In this embodiment the peptidomimetic can be derived from a biologically active metallopeptide. The biologically active metallopeptide can be of the formula:

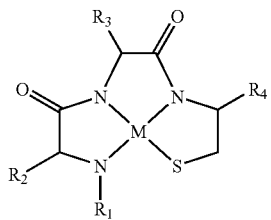

wherein
$R_1$ is one or more amino acid residues or derivatives thereof and optionally a terminal group moiety, or is an amino acid side chain moiety or derivative thereof;

$R_2$ is an amino acid side chain moiety or derivative thereof;

$R_3$ is any moiety other than H;

$R_4$ is a terminal group moiety, one or more amino acid residues or derivatives thereof and optionally a terminal group moiety, or an amino acid side chain moiety or derivative thereof; and M is a metal ion.

In this embodiment, $R_7$ can occupy a similar descriptor space as $R_1$, and at least either $R_6$ occupy a similar descriptor space as $R_2$ or $R_5$ occupy a similar descriptor space as $R_3$. The embodiment further includes instances wherein $R_7$ is a functional or structural homologue of $R_1$, and at least either $R_6$ is a functional or structural homologue of $R_2$ or $R_5$ is a functional or structural homologue of $R_3$.

In yet another embodiment the invention provides a method of deriving a peptidomimetic of a biologically active metallopeptide comprising the steps of:

(a) selecting a biologically active metallopeptide with a ring structure defining a template space, the metallopeptide being of the formula:

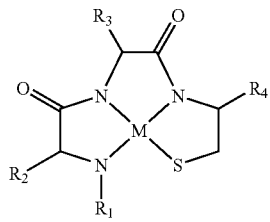

wherein $R_1$ is at least one natural or unnatural L- or D-amino acid residues and optionally any terminal or capping group;

$R_2$ and $R_3$ are the same or different and independently selected from an amino acid side chain moiety or derivative thereof;

$R_4$ is any terminal or capping group and optionally any one or more natural or unnatural L- or D-amino acid residues; and M is a metal ion;

(b) providing a non-peptidic ring structure superimposable on the template space defined by at least one ring of the ring structure of the biologically active metallopeptide, the non-peptidic ring structure being of the formula:

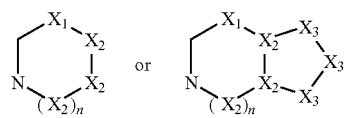

wherein $X_1$ is $(CH_2)_m$ or $X_3$;

$X_2$ is independently $CH_2$, CH, NH or N;

$X_3$ is independently $(CH_2)_n$, CH, NH, N, O, C=O, C=S, S, S=O, or $SO_2$;

n is 0, 1, 2 or 3; and m is 0 or 1;

provided that any two adjacent CH groups, adjacent NH and CH groups or adjacent NH groups may optionally form a double bond; and (c) adding at least three elements $R_5$, $R_6$, and $R_7$, to the non-peptidic ring structure, whereby a peptidomimetic of one of the following formulas results:

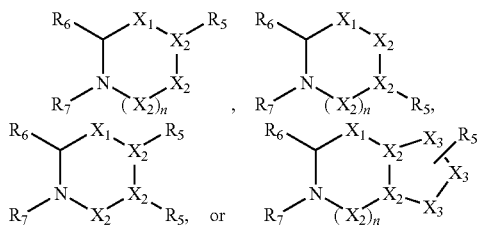

wherein $R_5$ is any moiety other than H;

$R_6$ is an amino acid side chain moiety or derivative thereof;

$R_7$ is one or more amino acid residues or derivatives thereof and optionally a terminal group moiety, or is an amino acid side chain moiety or derivative thereof; and $R_7$ occupies a similar descriptor space as $R_1$ and at least either $R_6$ occupies a similar descriptor space as $R_2$ or $R_5$ occupies a similar descriptor space as $R_3$.

In this embodiment, $R_7$ can be a functional or structural homologue of $R_1$, and at least either $R_6$ is a functional or structural homologue of $R_2$ or $R_5$ is a functional or structural homologue of $R_3$. The method can further include the step of comparing the biological activity of the peptidomimetic to that of the biologically active metallopeptide, using an known assay method, include those discussed above.

In another embodiment the invention provides melanocortin receptor-specific peptidomimetics of the formula:

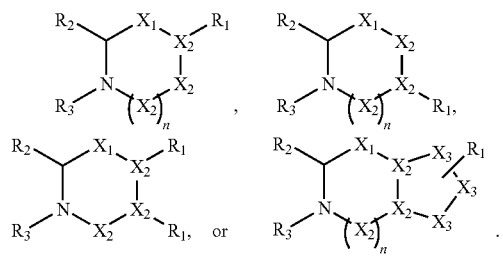

wherein $X_1$ is $(CH_2)_m$ or $X_3$;

$X_2$ is independently $CH_2$, CH, NH or N;

$X_3$ is independently $(CH_2)_n$, CH, NH, N, O, C=O, C=S, S, S=O, or $SO_2$;

$R_1$ is any moiety other than H;

$R_2$ is an amino acid side chain moiety or derivative thereof;

$R_3$ comprises $R_5$-$R_4$-, where $R_4$ is an L- or D-amino acid with an aromatic side chain group, such aromatic side chain group optionally functionalized with one or more halogen, alkyl or aryl groups, and $R_5$ is optionally not present, is one or more amino acid residues or derivatives thereof and optionally a terminal group moiety, or is a terminal group moiety;

n is 0, 1, 2 or 3; and m is 0 or 1;

provided that any two adjacent CH groups, adjacent NH and CH groups or adjacent NH groups may optionally form a double bond.

R$_4$ may be an L- or D-configuration of Phe, Phe(2-Cl), Phe(4-Cl), Phe(2,4-diCl), Phe(3,4-diCl), Phe(4-NO$_2$), Phe(4-Me), Phe(4-Phenyl), HPhe, Pgl, Trp, Nal 1, Nal 2, Bip, Dip, Bpa, Ser(Bzl), Lys(Z), Lys(Z-2'Br), Lys(Bz), Thr(Bzl), Cys (Bzl), Tyr(BzlCl$_2$), pF-Phe, Phe(4-Br), Phe(4-CF$_3$), Phe(3,4-diF), Phe(4-I) or Phe(3,4-di-OMe). R$_5$ may include an L- or D-configuration of His, Ser(Bzl), Tic, heptanoyl-Ser(Bzl), hexanoyl-Ser(Bzl), Hyp(Bzl), 4-phenylPro, 5-phenylPro, Tiq, Atc, Igl, Hyp(O-2-Naphthyl), Hyp(O-Phenyl), 2-Aic, Idc, 1-Aic, NH$_2$(CH$_2$)$_6$CO—, Benzyl, Beta-homoSer(Bzl), Ser(O-2-Naphthyl), Ser(O-Phenyl), Ser(O-4-Cl-Phenyl), Ser (O-2-Cl-Phenyl), Thr(Bzl), Tic, heptanoyl-Thr(Bzl), hexanoyl-Thr(Bzl), Beta-homoThr(Bzl), Thr(O-2-Naphthyl), Thr(O-Phenyl), Thr(O-4-Cl-Phenyl) or Thr(O-2-Cl-Phenyl).

In one embodiment, R$_1$ is

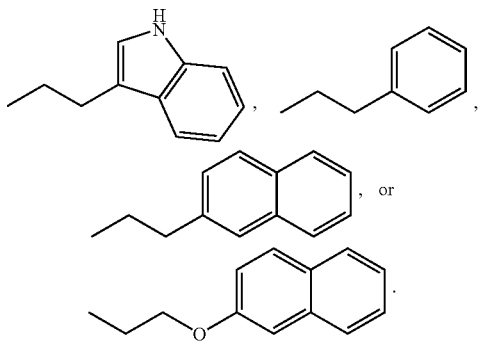

In another embodiment, R$_2$ is —(CH$_2$)$_4$NH$_2$, —(CH$_2$)$_3$NHC(NH$_2$)=NH, —(CH$_2$)$_3$NHCOCH$_3$, —(CH$_2$)$_3$NH-COOCH$_3$, —(CH$_2$)$_2$NHC(NH$_2$)=NH, —(CH$_2$)$_2$NHCONH$_2$, —(CH$_2$)$_4$NHCOH, —(CH$_2$)$_4$NHCOCH$_3$, —(CH$_2$)$_3$NHCONHCH$_3$, —(CH$_2$)$_3$NHSO$_2$NH$_2$, —(CH$_2$)$_3$NHSO$_2$CH$_3$, —(CH$_2$)$_3$NH$_2$, —(CH$_2$)$_2$CONH$_2$, —(CH$_2$)$_3$NH(C=NH)NHMe, —(CH$_2$)$_3$NH(C=NH)NHEt, —(CH$_2$)$_3$NH(C=NH)NHPr, —(CH$_2$)$_3$NH(C=NH)NHPr-i, —(CH$_2$)$_3$NH(C=NH)NH$_2$, —(CH$_2$)$_4$NHCONH$_2$, —(CH$_2$)$_4$NH(C=NH)NH$_2$,

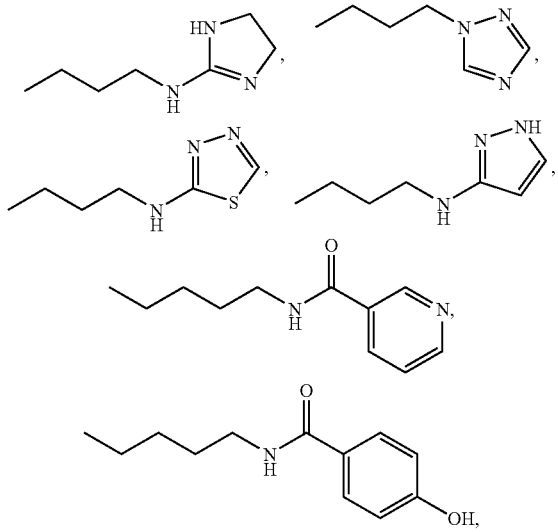

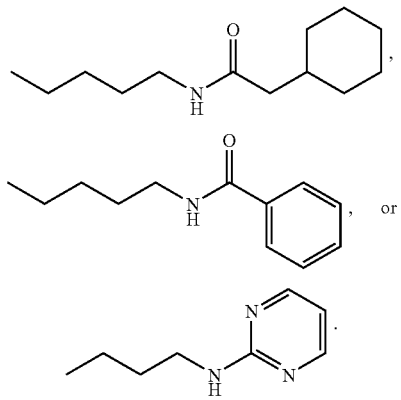

The melanocortin receptor-specific peptidomimetics thus include peptidomimetics of the following formulas:

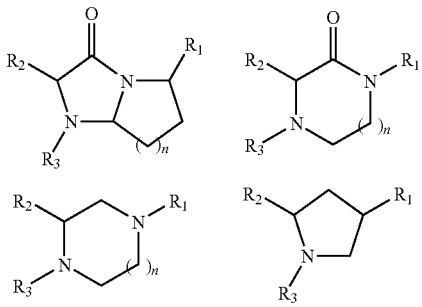

where R$_1$, R$_2$, R$_3$ and n are as defined above.

In another embodiment, the invention provides a melanocortin receptor-specific peptidomimetic of the formula:

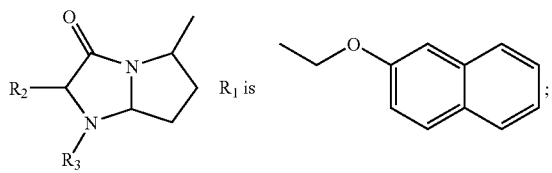

wherein

R$_2$ is —(CH$_2$)$_4$NH$_2$ or —(CH$_2$)$_3$NH(C=NH)NH$_2$; and

R$_3$ includes R$_5$—R$_4$—, where R$_4$ is is L- or D-Phe, pF-Phe, Phe(4-Br), Phe(4-CF$_3$), Phe(4-Cl), Phe(2-Cl), Phe(2,4-diCl), Phe(3,4-diCl), Phe(3,4-diF), Phe(4-I), Phe(3,4-di-OMe), Phe(4-Me) or Phe(4-NO$_2$) and R$_5$ is optionally not present or is L- or D-His, Ser(Bzl), Tic, heptanoyl-Ser(Bzl), Hyp(Bzl), 4-phenylPro, 5-phenylPro, Tiq, Atc, Igl, Hyp(O-2-Naphthyl), Hyp(O-Phenyl), 2-Aic, Idc, 1-Aic, NH$_2$(CH$_2$)$_6$CO—, Benzyl, Beta-homoSer(Bzl), Ser(O-2-Naphthyl), Ser(O-Phenyl), Ser(O-4-Cl-Phenyl) or Ser(O-2-Cl-Phenyl).

In another embodiment, the invention provides a melanocortin receptor-specific peptidomimetic of the formula:

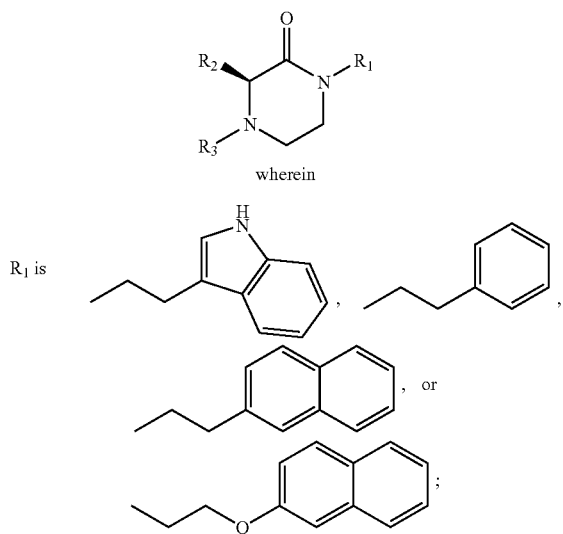

wherein R₁ is

R₂ is —(CH₂)₄NH₂, —(CH₂)₃NHC(NH₂)=NH, —(CH₂)₃NHCOCH₃, —(CH₂)₃NHCOOCH₃, —(CH₂)₂NHC(NH₂)=NH, —(CH₂)₂NHCONH₂, —(CH₂)₄NHCOH, —(CH₂)₄NHCOCH₃, —(CH₂)₃NHCONHCH₃, —(CH₂)₃NHSO₂NH₂, —(CH₂)₃NHSO₂CH₃, —(CH₂)₃NH₂, —(CH₂)₂CONH₂, —(CH₂)₃NH(C=NH)NHMe, —(CH₂)₃NH(C=NH)NHEt, —(CH₂)₃NH(C=NH)NHPr, —(CH₂)₃NH(C=NH)NHPr-i, —(CH₂)₃NH(C=NH)NH₂, —(CH₂)₄NHCONH₂, —(CH₂)₄NH(C=NH)NH₂,

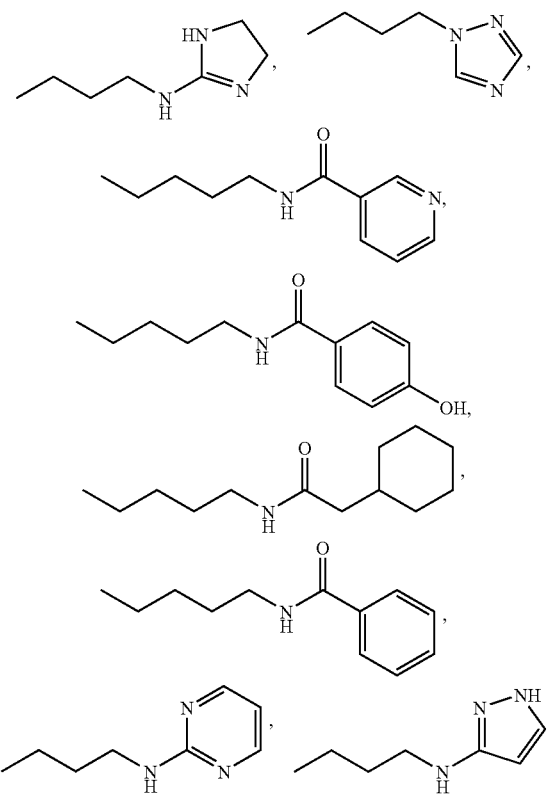

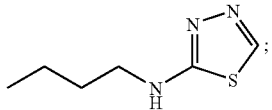

R₃ includes R₅-R₄-, where R₄ is is L- or D-Phe, pF-Phe, Phe(4-Br), Phe(4-CF₃), Phe(4-Cl), Phe(2-Cl), Phe(2,4-diCl), Phe(3,4-diCl), Phe(3,4-diF), Phe(4-I), Phe(3,4-di-OMe), Phe(4-Me) or Phe(4-NO₂) and R₅ is optionally not present or is L- or D-His, Ser(Bzl), Tic, heptanoyl-Ser(Bzl), Hyp(Bzl), 4-phenylPro, 5-phenylPro, Tiq, Atc, Igl, Hyp(O-2-Naphthyl), Hyp(O-Phenyl), 2-Aic, Idc, 1-Aic, NH₂(CH₂)₆CO—, Benzyl, Beta-homoSer(Bzl), Ser(O-2-Naphthyl), Ser(O-Phenyl), Ser(O-4-Cl-Phenyl) or Ser(O-2-Cl-Phenyl).

The invention further provides a method of deriving a peptidomimetic that binds to a target of interest, such method including the steps of:

(a) selecting a known amino acid sequence with a known primary structure of n residues, where n is at least 4, which known amino acid sequence binds to the target of interest;

(b) designing a library of amino acid sequences by selecting at least two consecutive residues from a stretch of consecutive residues in the known primary structure and inserting a residue providing both an N and S for metal ion complexation on the carboxy terminal end of two of the at least two selected consecutive residues, or alternatively selecting at least three consecutive residues from a stretch of consecutive residues in the known primary structure and substituting a residue providing both an N and S for metal ion complexation for the carboxy terminal residue of any consecutive stretch of three of the at least three selected consecutive residues, each such sequence constituting a library member, wherein each library member differs by at least one residue or the location of the insertion of or substitution with the residue providing both an N and S for metal ion complexation;

(c) constructing the library of designed amino acid sequences;

(d) complexing each library member of designed amino acid sequences to a metal ion, thereby forming a library of metallopeptides wherein the metal ion is complexed to at least three atoms in the peptide sequence, such at least three atoms being part of at least two amino acid residues comprising the peptide sequence, whereby such at least three atoms and the metal ion form a ring structure comprising at least one ring, the at least one ring of the ring structure defining a template space;

(e) screening the library of metallopeptides for binding to the target of interest;

(f) selecting a metallopeptide exhibiting binding to the target of interest;

(g) modeling a non-peptidic ring structure that is superimposable on the template space defined by at least one ring of the ring structure of the selected metallopeptide; and (h) forming a peptidomimetic by adding to the non-peptidic ring structure at least two elements independently comprising an amino acid residue, amino acid side chain moiety or derivative thereof, such at least two elements occupying a similar descriptor space as corresponding elements of the selected metallopeptide.

This method can further include the step of comparing the biological activity of the peptidomimetic to that of the selected metallopeptide. Such comparison may be by any means known, including the assays disclosed above. In one embodiment, screening for binding to the target of interest includes competing a known binding partner for binding to the target of interest with members of the library of metallopeptides, which known binding partner can be the known amino acid sequence with a known primary structure of n residues.

In this method, the known amino acid sequence with a known primary structure of n residues can be a peptide, a polypeptide or a protein. The library of designed amino acid sequences preferably includes at least one member wherein the residue providing both an N and S for metal ion complexation is the carboxyl terminal end residue of the amino acid sequence. In one embodiment, the library of designed amino acid sequences includes at least one member wherein the residue providing both an N and S for metal ion complexation is not the carboxyl terminal end residue of the amino acid sequence. In another embodiment, the library of designed amino acid sequences includes at least one member with at least four residues, wherein the residue providing both an N and S for metal ion complexation is inserted between two adjacent consecutive residues from a stretch of consecutive residues in the known primary structure.

The residue providing both an N and S for metal ion complexation can be an L- or D-3-mercapto amino acid, such as L- or D-cysteine, L- or D-penicillamine, 3-mercapto phenylalanine, or a homologue of any of the foregoing. The metal ion can be an ion of V, Mn, Fe, Co, Ni, Cu, Zn, Ga, As, Se, Y, Mo, Tc, Ru, Rh, Pd, Ag, Cd, In, Sn, W, Re, Os, Ir, Pt, Au, Hg, Tl, Pb, Bi, Po, At, Sm, Eu or Gd.

In the practice of this invention, any cysteine residue in the library of amino acid sequences other than the inserted residue providing both an N and S for metal ion complexation can be is substituted with a homologue not containing a free sulfhydryl group. Thus the cysteine can be substituted with a glycine, alanine, serine, aminoisobutyric acid or dehydroalanine residue, with an S-protected cysteine, or in general with any neutral mimetic of an amino acid residue of less than about 150 MW.

In the practice of this invention, any proline residue in the two residues immediately adjacent the amino-terminus side of the residue providing both an N and S in any library member can be substituted with a residue providing an N for metal ion complexation. Thus the praline can be substituted with a glycine, alanine, serine, aminoisobutyric acid or dehydroalanine residue, or in general with any neutral mimetic of an amino acid of less than about 150 MW that provides an N for metal ion complexation.

In the practice of this invention, if n is at least about 15 the method further can optionally include the step of dividing the primary structure into at least three divided primary structures, each such divided primary structure overlapping the primary structure of each adjacent divided primary structure by at least two residues, and thereafter following steps (b) through (f) with respect to each such secondary parent polypeptide. Further, in the method at least one residue of the selected at least two consecutive residues can be a homologue of the corresponding residue in the stretch of consecutive residues in the known primary structure.

A primary object of this invention is provide a method for making peptidomimetic compounds based on information derived from metallopeptides, which peptidomimetic compounds incorporate a ring structure.

Another object of this invention to provide peptidomimetic compounds derived from conformationally-constrained metallopeptides that form a surrogate for naturally-occurring structural motifs, such as those motifs commonly found in naturally-occurring peptides and proteins, including reverse turn structures, type I, II and III beta turns, gamma turns, inverse gamma turns, and short helical, sheet and extended chain structures. A secondary structural motif is necessarily defined by a conformationally-constrained metallopeptide, which secondary structural motif, mimics, or can be made to mimic, the topologies found in naturally occurring structural motifs. The peptidomimetic compounds are derived from such metallopeptides, whereby the peptidomimetics compounds similar mimic topologies found in naturally occurring structural motifs.

Another object of this invention is to provide peptidomimetics compounds that include a ring structure that positions amino acid residues, amino acid side chain moieties and derivatives thereof in stereochemical space mimicking a naturally occurring reverse turn structure.

Another object of this invention is to provide peptidomimetic compounds with amino acid side chain moieties or derivatives thereof with substantial topological similarities to either metallopeptides or classical protein turn structures or both. Amino acid side chain moieties and derivatives thereof associated with the peptidomimetic compounds can be topographically positioned such that they occupy the same chemical space as the corresponding side chains in either metallopeptides or classical turn structures or both.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

DESCRIPTION OF THE PREFERRED EMBODIMENTS

Figure 1:
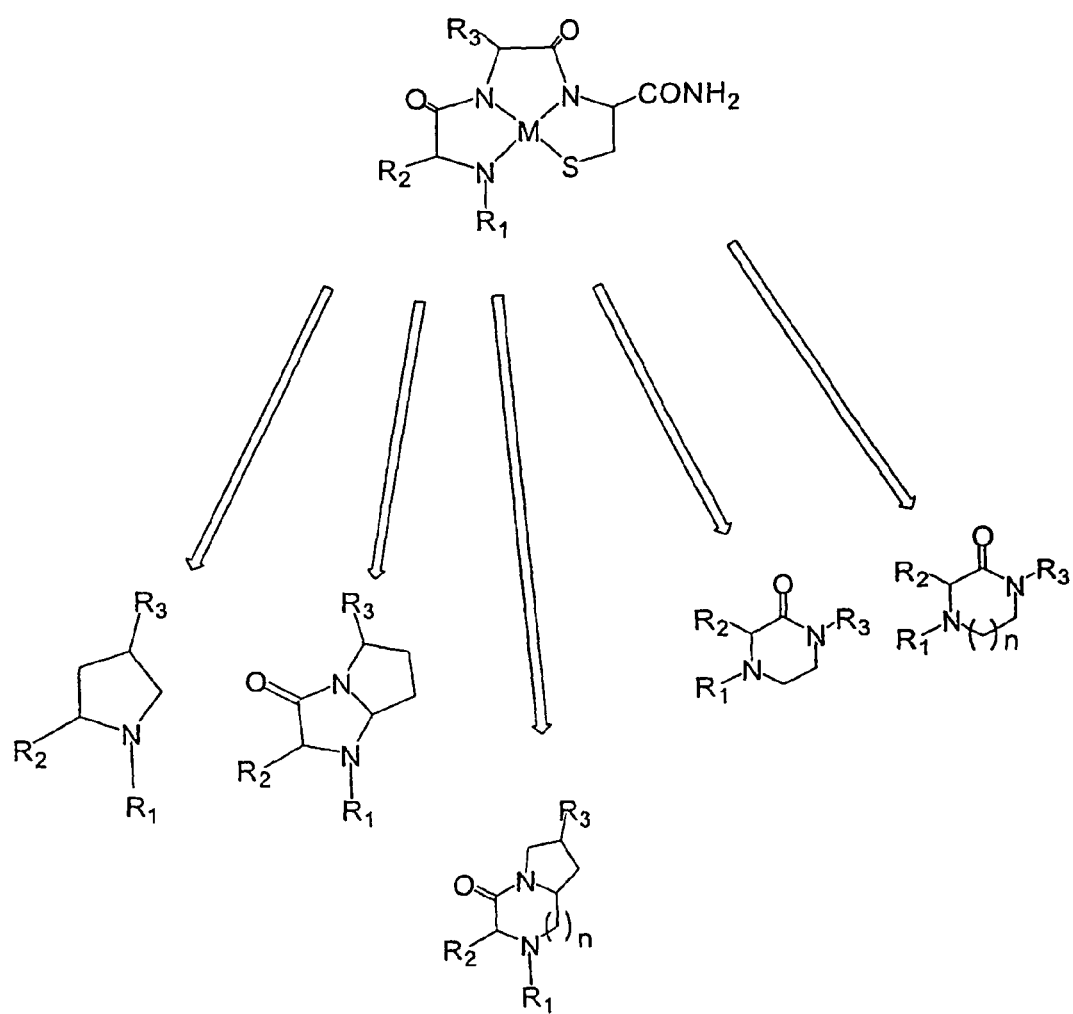
FIG. 1 depicts an idealized scheme of this invention for deriving biologically active peptidomimetics from a metallopeptide, wherein $R_1$, $R_2$ and $R_3$ each independently represent an amino acid side chain moiety, derivative thereof, terminal group, capping group or chain of two or more amino acid residues and M depicts a metal ion, such as a metal ion forming a tetradentate complex.

Best Modes for Carrying Out the Invention

Definitions. Certain terms as used throughout the specification and claims are defined as follows:

The terms "bind," "binding," "complex," and "complexing," as used throughout the specification and claims, are generally intended to cover all types of physical and chemical binding, reactions, complexing, attraction, chelating and the like.

The "peptides" of this invention can be a) naturally-occurring, b) produced by chemical synthesis, c) produced by recombinant DNA technology, d) produced by biochemical or enzymatic fragmentation of larger molecules, e) produced by methods resulting from a combination of methods a through d listed above, or f) produced by any other means for producing peptides.

By employing chemical synthesis, a preferred means of production, it is possible to introduce various amino acids which do not naturally occur along the chain, modify the N- or C-terminus, and the like, thereby providing for improved stability and formulation, resistance to protease degradation, and the like.

The term "peptide" as used throughout the specification and claims is intended to include any structure comprised of two or more amino acids, including chemical modifications and derivatives of amino acids. For the most part, peptides discussed herein comprise fewer than 100 amino acids, and preferably fewer than 60 amino acids, and most preferably from about 2 to 20 amino acids. The amino acids forming all or a part of a peptide may be naturally occurring amino acids, stereoisomers and modifications of such amino acids, non-protein amino acids, post-translationally modified amino acids, enzymatically modified amino acids, constructs or structures designed to mimic amino acids, and the like, so that the term "peptide" includes pseudopeptides and peptidomimetics, including structures which have a non-peptidic backbone. The term "peptide" also includes dimers or multimers of peptides. A "manufactured" peptide includes a peptide produced by chemical synthesis, recombinant DNA technology, biochemical or enzymatic fragmentation of larger molecules, combinations of the foregoing or, in general, made by any other method.

The "amino acid" and "amino acids" used in this invention, and the terms as used in the specification and claims, include the known naturally occurring protein amino acids, which are referred to by both their common three letter abbreviation and single letter abbreviation. See generally *Synthetic Peptides: A User's Guide*, G A Grant, editor, W. H. Freeman & Co., New York, 1992, the teachings of which are incorporated herein by reference, including the text and table set forth at pages 11 through 24. As set forth above, the term "amino acid" also includes stereoisomers and modifications of naturally occurring protein amino acids, non-protein amino acids, post-translationally modified amino acids, enzymatically synthesized amino acids, derivatized amino acids, constructs or structures designed to mimic amino acids, and the like. Modified and unusual amino acids are described generally in *Synthetic Peptides: A User's Guide*, cited above; Hruby V J, Al-obeidi F and Kazmierski W: *Biochem J* 268:249-262, 1990; and Toniolo C: *Int J Peptide Protein Res* 35:287-300, 1990; the teachings of all of which are incorporated herein by reference.

The term "amino acid side chain moiety" used in this invention, including as used in the specification and claims, includes any side chain of any amino acid, as the term "amino acid" is defined herein. This thus includes the side chain moiety present in naturally occurring amino acids. It further includes side chain moieties in modified naturally occurring amino acids, such as glycosylated amino acids. It further includes side chain moieties in stereoisomers and modifications of naturally occurring protein amino acids, non-protein amino acids, post-translationally modified amino acids, enzymatically synthesized amino acids, derivatized amino acids, constructs or structures designed to mimic amino acids, and the like. For example, the side chain moiety of any amino acid disclosed herein is included within the definition.

The "derivative" of an amino acid side chain moiety includes any modification to or variation in any amino acid side chain moieties, including a modification of naturally occurring amino acid side chain moieties. By way of example, derivatives of amino acid side chain moieties include straight chain or branched, cyclic or noncyclic, substituted or unsubstituted, saturated or unsaturated, alkyl, aryl or aralkyl moieties.

The following abbreviations for amino acids have the meanings giving, it being understood that any amino acid list may be in the L- or D-configuration:

| | |
|---|---|
| Abu | gamma-amino butyric acid |
| 2-Abz | 2-amino benzoic acid |
| 3-Abz | 3-amino benzoic acid |
| 4-Abz | 4-amino benzoic acid |
| Achc | 1-amino-cyclohexane-1-carboxylic acid |
| Acpc | 1-amino-cyclopropane-1-carboxylic acid |
| 12-Ado | 12-amino dodecanoic acid |
| 7-Ahept | 7-amino heptanoic acid |
| Aib | alpha-aminoisobutyric acid |
| Aic | 2-aminoindane-2-carboxylic acid |
| 6-Ahx | 6-amino hexanoic acid |
| Amb | 4-(aminomethyl)-benzoic acid |
| Amc | 4-(aminomethyl)-cyclohexane carboxylic acid |
| 7'-amino-heptanoyl | $NH_2-(CH_2)_6CO-$ |
| 8-Aoc | 8-amino octanoic acid |
| Arg(Tos) | $N^G$-para-tosyl-arginine |
| Asp(anilino) | beta-anilino-aspartic acid |
| Asp(3-Cl-anilino) | beta-(3-chloro-anilino)-aspartic acid |
| Asp(3,5-diCl-anilino) | beta-(3,5-dichloro anilino)-aspartic acid |
| Atc | 2-aminotetralin-2-carboxylic acid |
| 11-Aun | 11-amino undecanoic acid |
| AVA | 5-amino valeric acid |
| Beta-hHyp(Bzl) | Beta-(O-benzyl)-homohydroxyproline |
| Beta-hSer(Bzl) | Beta-(O-benzyl)-homoserine |
| Bip | biphenylalanine |
| Bzl | benzyl |
| Bz | benzoyl |
| Cha | cyclohexylalanine |
| Chg | cyclohexylglycine |
| Cmpi | 4-caboxymethyl-piperazine |
| Dip | 3,3-diphenylalanine |
| Disc | 1,3-dihydro-2H-isoindolecarboxylic acid |
| Dpr(beta-Ala) | $N^{beta}$-(3-aminopropionyl)-alpha,beta-diaminopropionic acid |
| Et- | ethyl |
| GAA | epsilon-guanidino acetic acid |
| GBzA | 4-guanidino benzoic acid |
| B-Gpa | 3-guanidino propionic acid |
| GVA(Cl) | beta-chloro-epsilon-guanidino valeric acid |
| Heptanoyl | $CH_3-(CH_2)_5CO-$ |
| hPhe | homophenylalanine |
| hSer | homoserine |
| Hyp | hydroxy proline |
| hHyp | homo hydroxy proline |
| Hyp(Bzl) | O-benzyl-hydroxyproline |
| Idc | indoline-2-carboxylic acid |
| Igl | indanylglycine |
| Inp | isonipecotic acid |
| Lys(Z) | N-epsilon-benzyloxycarbonyl-lysine |

-continued

| | |
|---|---|
| Me- | methyl |
| Nal 1 | 3-(1-naphthyl)alanine |
| Nal 2 | 3-(2-naphthyl)alanine |
| (N-Bzl)Nal 2 | N-benzyl-3-(2-naphthyl) alanine |
| 2-Naphthylacetyl | 2-naphthyl-CH$_2$CO— |
| (Nlys)Gly | N-(4-aminobutyl)-glycine |
| (N-PhEt)Nal 2 | N(2-phenylethyl)-3-(2-naphthyl) alanine |
| OcHx | cyclohexyl ester |
| Phg | phenylglycine |
| pF-Phe | para-fluoro-phenylalanine |
| Phe(4-Br) | 4-bromo-phenylalanine |
| Phe(4-CF$_3$) | 4-trifluoromethyl-phenylalanine |
| Phe(4-Cl) | 4-chloro-phenylalanine |
| Phe(2-Cl) | 2-chloro-phenylalanine |
| Phe(2,4-diCl) | 2,4,-dichloro-phenylalanine |
| Phe(3,4-diCl) | 3,4,-dichloro-phenylalanine |
| Phe(3,4-diF) | 3,4,-difluoro-phenylalanine |
| Phe(4-I) | 4-iodo-phenylalanine |
| Phe(3,4-di-OMe) | 3,4,-dimethoxy-phenylalanine |
| Phe(4-Me) | 4-methyl-phenylalanine |
| Phe(4-NO$_2$) | 4-nitro-phenylalanine |
| Pip | pipecolic acid |
| Pr | propyl |
| Pr-I | isopropyl |
| 3-Pya | 3-pyridylalanine |
| Pyr | pyroglutamic acid |
| Qal(2') | beta-(2-quinolyl)-alanine |
| Sal | 3-styrylalanine |
| Sar | sarcosine |
| Ser(Bzl) | O-benzyl-serine |
| Ser(2-Naphthyl) | O-2-Naphthyl-serine |
| Ser(Phenyl) | O-2-Phenyl-serine |
| Ser(4-Cl-Phenyl) | O-4-Cl-Phenyl-serine |
| Ser(2-Cl-Phenyl) | O-2-Cl-Phenyl-serine |
| Ser(p-Cl-Bzl) | O-4-Cl-Benzyl-serine |
| Thr(Bzl) | O-Benzyl-threonine |
| Tic | 1,2,3,4-tetrahydroisoquinoline-3-carboxylic acid |
| Tiq | 1,2,3,4-tetrahydroisoquinoline-1-carboxytic acid |
| Tle | tert-butylalanine |
| Tpi | 1,2,3,4-tetrahydronorharman-3-carboxylic acid |
| Tyr(Bzl) | O-benzyl-tyrosine |
| Tyr(2,6-DiCl-Bzl) | O-(2,6 dichloro)benzyl-tyrosine |
| Z | benzyloxycarbonyl |

In the listing of compounds according to the present invention, conventional amino acid residues have their conventional meaning as given in Chapter 2400 of the *Manual of Patent Examining Procedure*, 7$^{th}$ Ed. Thus, "Nle" is norleucine; "Asp" is aspartic acid; "His" is histidine; "D-Phe" is D-phenylalanine; "Arg" is arginine; "Trp" is tryptophan; "Lys" is lysine; "Gly" is glycine; "Pro" is proline; "Tyr" is tyrosine, "Ser" is serine and so on. The following amino acids are employed in certain embodiments of this invention:

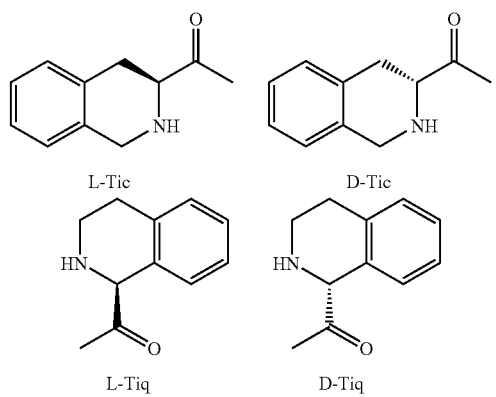

L-Tic   D-Tic

L-Tiq   D-Tiq

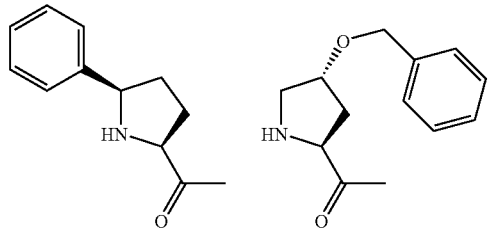

(2S,5R)-5-Phenyl-pyrrolidine-2-carbonyl   trans-Hyp(Bzl)

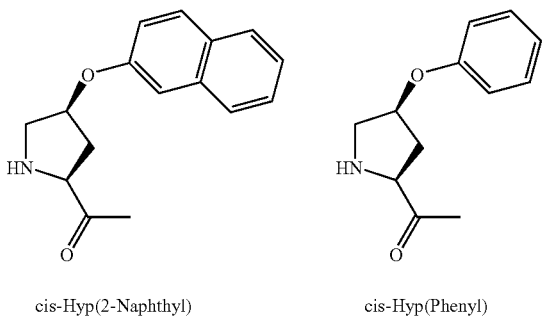

cis-Hyp(2-Naphthyl)   cis-Hyp(Phenyl)

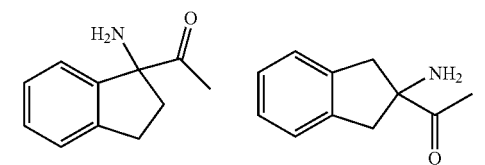

1-Aic   2-Aic

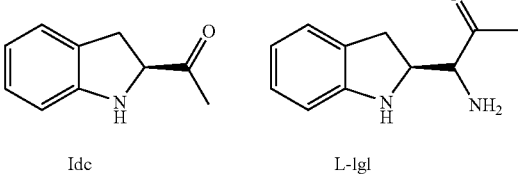

Idc   L-Igl

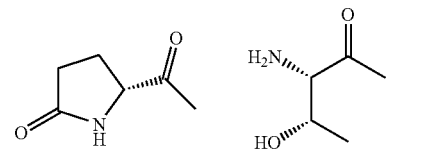

D-Pyr   Allo-Thr

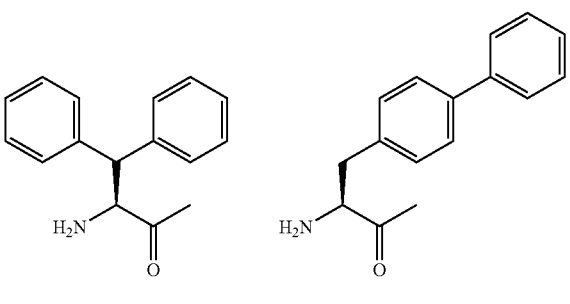

L-Dip   L-Bip

-continued

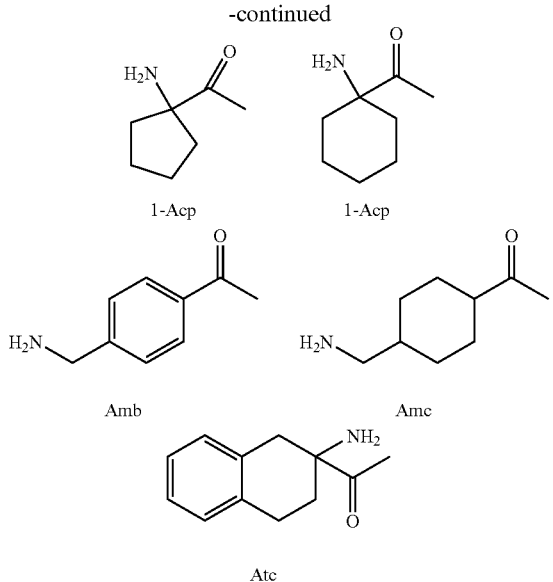

A single amino acid, including stereoisomers and modifications of naturally occurring protein amino acids, non-protein amino acids, post-translationally modified amino acids, enzymatically synthesized amino acids, derivatized amino acids, constructs or structures designed to mimic amino acids, and the like, including all of the foregoing, is sometimes referred to herein as a "residue."

A variety of chemicals and compounds are employed in this invention, and the following abbreviations have the meanings given:

| | |
|---|---|
| Cbz | benzyloxycarbonyl |
| DCM | dichloromethane |
| DEAD | diethyl azodicarboxylate |
| DIC | 1,3-diisopropylcarbodiimide |
| DIEA | N,N-diisopropylethylamine |
| DMF | N,N-dimethylformamide |
| DMSO | dimethyl sulfoxide |
| Fmoc | 9-fluorenylmethoxycarbonyl |
| HOAt | 1-hydroxy-7-azabenzotriazole |
| LAH | lithium aluminum hydride |
| NMM | N-methyl-morpholine |
| NMP | 1-methyl-2-pyrrolidinone |
| TBTU | 2-(1H-Benzotriazole-1-yl)-1,1,3,3-tetramethyluronium tetrafluoroborate |
| TEA | triethylamine |
| TFA | trifluoroacetic acid |
| THF | tetrahydrofuran |
| TIS | triisopropylsilane |
| TPP | triphenylphosphine |

The peptidomimetic compounds disclosed herein can be used for both medical applications and animal husbandry or veterinary applications. Typically, the product is used in humans, but may also be used in other mammals. The term "patient" is intended to denote a mammalian individual, and is so used throughout the specification and in the claims. The primary applications of this invention involve human patients, but this invention may be applied to laboratory, farm, zoo, wildlife, pet, sport or other animals.

In general, the peptidomimetic compounds of this invention may be synthesized by solid-phase synthesis or other synthetic schemes and purified according to methods known in the art. Any of a number of well-known procedures utilizing a variety of resins and reagents may be used to prepare the peptidomimetic compounds of this invention.

The peptidomimetic compounds of this invention may be in the form of any pharmaceutically acceptable salt. Acid addition salts of the peptidomimetic compounds of this invention are prepared in a suitable solvent from the peptidomimetic compound and an excess of an acid, such as hydrochloric, hydrobromic, sulfuric, phosphoric, acetic, trifluoroacetic, maleic, succinic or methanesulfonic. The acetate salt form is especially useful. Where the peptidomimetic compounds of this invention include an acidic moiety, suitable pharmaceutically acceptable salts may include alkali metal salts, such as sodium or potassium salts, or alkaline earth metal salts, such as calcium or magnesium salts.

The invention provides a pharmaceutical composition that includes a peptidomimetic compound of this invention and a pharmaceutically acceptable carrier. The carrier may be a liquid formulation, and is preferably a buffered, isotonic, aqueous solution. Pharmaceutically acceptable carriers also include excipients, such as diluents, carriers and the like, and additives, such as stabilizing agents, preservatives, solubilizing agents, buffers and the like, as hereafter described.

It is known and appreciated that peptides, due in part to their enormous structural flexibility and diversity, make an ideal candidate for rapid drug lead generation. Highly potent peptide leads for almost any biological target can be rapidly generated using synthetic or biological (such as phage display) peptide libraries. However, conversion of these leads to commercially viable molecules remains an arduous, expensive, labor and intellect intensive task, with little assurance of success.

The use of metallopeptide combinatorial libraries and methods of iterative synthesis provides a means to make and identify a metallopeptide binding to a receptor of interest with desired affinity and specificity. These methods are generally disclosed and described in the references cited under the heading "Metallopeptides" in the Background Art section above. In these metallopeptide structures the peptide backbone is conformationally fixed about a metal ion, thereby creating a fixed and novel scaffold, while the side chains of individual amino acids remain flexible, thereby allowing interactions with the biological target. The co-ordination sphere of the complexing metal ion thus primarily defines the metallopeptide structure. A comparison of peptide-metal scaffolds with those of classical secondary peptide structures, such as reverse turn, extended and beta sheet structures, demonstrates that the metallopeptide approach is capable of mimicking the side chain topologies of these classical structural motifs of the peptides. The metallopeptide approach works with many receptors specific for small peptides, and may work with most such receptors, since the biological activity of small peptide specific binding pair members is almost universally a consequence of the folded secondary structure of the small peptide.

In one approach using metallopeptides, a series of metallopeptides are generated from a known peptide or small protein with biological activity by algorithm-driven insertion of a selected amino acid and subsequent complexation of a metal ion to the peptide at selected iterative positions. This method is generally disclosed in International Patent Application Serial No. PCT/US01/50075, entitled Identification of Target-Specific Folding Sites in Peptides and Proteins, filed Dec. 19, 2001. This process rapidly and accurately predicts the biologically relevant site of peptide folding in the otherwise floppy and conformationally unrestrained peptide molecule.

In one embodiment, a metallopeptide is described by the systematic analysis of a known parent polypeptide to determine at least one active sequence or domain in the parent polypeptide that is involved in the interaction, such as binding, with a target substance. As used herein, "parent polypeptide" refers to any sequence of amino acid residues that exhibits interaction, such as binding, to a target substance, and which may thus constitute a peptide, a polypeptide or a protein. The parent polypeptide is generally a peptide or polypeptide, with from about 3 to about 100 amino acid residues, but the phrase parent polypeptide can also include larger constructs, generally considered in the art to be large polypeptides or proteins. To make a metallopeptide, the primary structure, which is to say the sequence, of at least part, and preferably of all, of the parent polypeptide must be known. However, it is not necessary to have any information concerning the secondary or tertiary structure of the parent polypeptide in order to practice the method of the invention.

The parent polypeptide may be any sequence that exhibits binding to a receptor found on, for example, cells, tissues, organs or other biological materials. Examples of parent polypeptides include, without limitation, biologically active peptides, hormones, neurotransmitters, enzymes, antibodies and the like. Such parent polypeptides may transmit signals directly or indirectly as a result of binding to a receptor, and thus a parent polypeptide may be an agonist, an antagonist, or a mixed agonist-antagonist. Examples of suitable parent polypeptides of the invention include melanocortin-receptor specific peptides, urokinase-type tissue plasminogen activator protein, amyloid beta-protein related peptides, prion disease related peptides, vasopressin peptides, oxytocin peptides, angiotensin peptides, calcitonin, calcitonin gene related peptide, opioid peptides, human growth hormone, human prolactin receptor ligands, various interferons, such as alpha-interferon, epidermal growth factor, tumor necrosis factor, and various hypotensive peptides, fibrinolytic peptides, chemotactic peptides, growth promoter peptides, mitogens, immunomodulators and the like.

In general, in order to make a metallopeptide for use in this invention, at least one assay or test to determine binding of the constructs of the invention to a receptor of interest, or optionally a method to determine at least one functional parameter, and preferably to also determine binding of the parent polypeptide to a receptor of interest, must be known. In a preferred embodiment of the invention, a competitive inhibition or similar assay is employed, whereby the binding or functional activity of a construct of the invention can be directly compared to the parent polypeptide, and relative binding or functional activity thus directly determined. In other embodiment other assays or tests may be employed. These assays may, but need not, be functional assays. Examples of assays include any of a variety of competitive inhibition assays, direct binding assays, functional assays, and the like. It is also possible and contemplated to employ assays that determine, for example, whether a construct of the invention is an agonist, antagonist or mixed agonist-antagonist, and further where binding and function can separately be determined, to independently determine both receptor affinity and specificity as well as functional activity. Examples of such assays and tests are well known and well documented in the art, and in general one or more such assays or tests are known for any parent polypeptide.

In a method of the invention, the parent polypeptide is employed for generation of one or more, and preferably of a series, of peptides that are then complexed to a metal ion, resulting in metallopeptides. In general, but not necessarily, the generated peptides are of shorter length than the parent polypeptide. However, it is possible and contemplated for the generated peptide to have a primary structure either as long as or longer than that of the parent polypeptide. The generated peptide, of whatever length, is complexed to a metal ion, thereby forming a metallopeptide. The metallopeptide is then employed in any of a variety of known or new assays or tests, and the binding or function, or both, of the metallopeptide compared to that of the parent polypeptide. Methods for accomplishing the foregoing are described in more detail in International Patent Application Serial No. PCT/US01/50075, entitled Identification of Target-Specific Folding Sites in Peptides and Proteins, filed Dec. 19, 2001, incorporated herein by reference.

The resulting metallopeptide can be employed in the methods of this invention for making a peptidomimetic. In one embodiment of this invention, it is possible to describe and generate high quality 3-D structural information based on bioactive structural characteristics of metallopeptides that does not require use of physical methods such as X-ray, NMR, molecular modeling in silico or other computational studies. As disclosed herein, this invention provides methods and approaches to rationally create small molecules, called a "peptidomimetic compound" or "peptidomimetic" herein, based on convoluted structural information derived from a biologically relevant metallopeptide. In general, a peptidomimetic compound of this invention will have one or more groups corresponding to amino acid side chain moieties or derivatives thereof, and may optionally further include one or more amino acid residues, including non-protein amino acid residues or mimetics or derivatives of amino acid residues.

This invention is based in part on the realization that the rigid structures of a metallopeptide molecule, resulting from complexation of a metal ion to a peptide segment, are predictable. The atomic co-ordinates of various atoms in the metal ion-bound peptide segment of the metallopeptides are well defined by the co-ordination chemistry and co-ordination sphere of the metal ion. This structural information, such as may be derived from the results of a series of biologically active, receptor specific metallopeptides, can be analyzed to define crucial sets of structural parameters resulting in biological activity. Due to the inherent rigidity of the peptide-metal ion scaffold in metallopeptides, the resulting structural data provides better structural information than data from NMR or similar studies on peptides or peptidomimetics. This makes it possible to use data resulting from biologically active, receptor specific metallopeptides for de novo design and development of small molecule-based drugs, such as peptidomimetic compounds and pharmaceutical compositions including peptidomimetic compounds. The invention thus employs a rational drug design paradigm, utilizing metallopeptides as the primary source of structural and conformational information, and resulting in non-metal small molecular scaffolds which are receptor-specific and can be either agonist or antagonist molecules. This provides a significant advantage over other prior art conventional methods of small molecule development, which generally result only in the development of receptor-specific antagonists, and rarely agonists.

The co-ordination sphere of the metal ion results, in a peptide sequence, in the formation of ring structures. Such ring structures are made up of one or more rings. Using a metal ion such as Re typically results in a 5-5-5-membered ring structure, as shown in FIG. 1. However, even with use of Re, other ring structures are possible; for example, a 5-5-6-membered ring structure can result from use of both homoCys and His in the sequence binding Re, and a 6-5-5-membered ring structure can result if Cys is at the N terminal position. The ring structure, and each individual ring forming a part thereof, defines what is called herein a "template space." A template space is a subset of chemical space, and includes at least one or more steric descriptors, such as size, volume, or conformational space. Thus the ring structure has a template space, and each ring, and combination of rings thereof, has a template space.

Biological activity of metallopeptides is due to various constituent parts referred to here as "elements," which elements include one or more amino acid residues, amino acid side chain moieties or derivatives thereof. These elements interact with receptor sites on a receptor, such that recognition of and interaction with the metallopeptide can take place, leading to a biochemical or pharmacological effect. In general, contributing interactions for recognition are electrostatic, hydrogen bonding, van der Waals and hydrophobic in nature.

Elements occupy what is defined herein as a "descriptor space." The descriptor space is a subset of chemical space, and includes one or more steric descriptors and one or more electronic or lipophilicity descriptors. The descriptor space of an element in a metallopeptide includes steric descriptors defining the relationship to the template space of the ring structure and individual rings thereof. Where, for example, the element is an amino acid side chain moiety, such as $R_2$ in the metallopeptide depicted in FIG. 1, the descriptor space of $R_2$ is sterically fixed in relation to the template space, and has specific spatial coordinates relative to the template space of the ring structure and individual rings thereof. However, in other instances the descriptor space of an element does not define a fixed relationship with the template space of the ring structure and individual rings thereof. For example, where $R_1$ is a chain of two or more amino acid residues, and the element is an amino acid side chain moiety of a residue separated by at least one residue from the metallopeptide ring structure, the descriptor space of the element has only a probabilistically determinable relationship with the template space of the ring structure and individual rings thereof, due to the conformational freedom of the element relative to the metallopeptide ring structure. Such a descriptor space of $R_2$ thus includes the probability map of potential physical locations of $R_2$, based on the conformational mobility of the element. The relative conformational energies of different conformations determine, in part, the probabilistically determinable relationship of the element with the template space, including the ring structure and individual rings thereof. The descriptor space further includes electronic or lipophilicity descriptors, such as electrostatic potentials, reactivity indices, liophilicity potentials or the like, which descriptors are relevant to interaction of the metallopeptide with a receptor, such as through electrostatic, hydrogen bonding, van der Waals or hydrophobic interaction. The descriptor space further can include steric descriptors between elements, or between one or more elements and a template space. For example, as between two elements the descriptor space can include molecular geometry considerations, such as distances and angles between key atoms. Other descriptors relevant to descriptor space include solvent accessible surface areas, van der Waals surfaces and electron densities.

Two different elements or groups of elements occupy a "similar descriptor space" when at least some descriptors are common, and the functionality of the elements is preserved. Functionality may be determined by receptor interaction. This may be determined by various means, such as by binding studies, functional studies or the like. The following example summarizes one aspect of the definitions given herein. Consider a metallopeptide of the general structure:

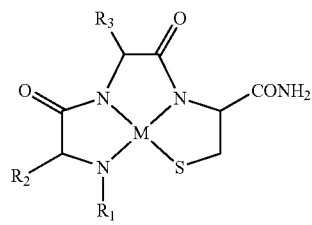

It may be seen that the 5-5-5-membered ring structure and each individual ring thereof defines a template space. Assuming that $R_1$ and $R_2$ are each an amino acid side chain moiety that contributes to biological activity of the metallopeptide, then each of $R_1$ and $R_2$ is an element. Each occupies a descriptor space defined by the amino acid side chain moiety (e.g. charge, lipophilicity and so on) and by the positional relationship of each to the other and to the template space. Consider a peptidomimetic of this invention of the general structure:

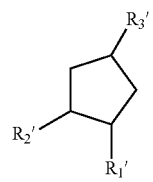

While this ring is depicted as homocyclic, it is to be understood that the ring may include one or more N or S groups, in addition to C groups, and may further include one or more double bonds. This peptidomimetic includes a ring that occupies a template space that is "superimposable" on a template space of a ring of the metallopeptide ring structure, where such superimposability is defined by, in part, the ring structure defining the template space positioning the elements (here $R_1'$ and $R_2'$) in the same or a similar descriptor space. That is, notwithstanding that the rings differ, though both are five-membered, the position and orientation of $R_1'$ relative to $R_2'$ may be functionally the same (occupy the same or a similar descriptor space) as is the position and orientation of $R_1$ relative to $R_2$, and thus the template spaces are superimposable. It may readily be seen that whether one template space is superimposable on another template space is frequently ascertained by empirical means, such as by binding assays, functional assays or the like employing the actual constructs. However, molecular modeling and other methods may also be employed to determine whether one template space is superimposable on another template space. It may further be seen that two different rings may be employed, where the rings are of different size, but nonetheless the rings occupy a template space that is superimposable. For example, consider the following peptidomimetic of this invention:

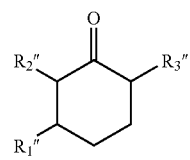

Here too while this ring is depicted as homocyclic, it is to be understood that the ring may include one or more N or S groups, in addition to C groups, and may further include one or more double bonds. Here the number of ring members differs from those of the corresponding ring in the ring structure of the metallopeptide. However, so long as the template space of this 6-membered ring is such that the position and orientation of $R_1''$ relative to $R_2''$ is functionally the same (occupies the same or a similar descriptor space) as is the position and orientation of $R_1$ relative to $R_2$, the template spaces of the 6-membered ring and the corresponding 5-membered ring in the ring structure of the metallopeptide are superimposable. Whether this template space is superimposable on another template space is largely a functional and empiric inquiry, addressing whether the descriptor spaces of elements are such that the resulting peptidomimetic is functional.

In the simplest case, structural identity of an element on the metallopeptide and the corresponding element on the peptidomimetic is a component of similar descriptor space. That is, if for example both $R_1$ and $R_1'$ are the same amino acid side chain moiety, then both definitionally occupy the same descriptor space where other descriptors, such as position and/or orientation relative to some other element or descriptor space, are present. However, $R_1$ and $R_1'$ may be different amino acid side chain moieties and nonetheless occupy a similar descriptor space within the definitions given here. For example, depending on the receptor site of the receptor of interest for which the element $R_1$ is specific, including the nature of the contributing interaction of such receptor site, any of a number of different amino acid side chain moieties may be functional. If a given element has a particular charge density and distribution, which charge density and distribution is complementary to a target receptor site in such a way that recognition of and interaction with the receptor is mediated, then another element with a functionally similar charge density and distribution, assuming correct positioning and orientation, may be employed, and by definition occupies a similar descriptor space. Given that in general receptor sites interact by electrostatic, hydrogen bonding, van der Waals and hydrophobic means, it follows that descriptor space must be constrained by the same interaction means. That is, if an amino acid side chain residue constitutes an element, occupying a descriptor space, where the interaction with the receptor side is by hydrophobic means, then another element which occupies a similar descriptor space on a different molecule will similarly interact by hydrophobic means, even if the elements are not chemically identical. By way of example, depending on the particular receptor site, an indole group may be substitute with a phenyl, a homocyclic ring substituted with a heterocyclic ring, one aliphatic side chain substituted with another aliphatic side chain, different functional groups may be employed, and the like. It is to be appreciated that no global one-to-one substitution table of similar descriptor space is possible, given that descriptor space is necessarily specific to other descriptor space and to template space, as well as to the receptor site for which the descriptor space is relevant.

In one aspect the invention thus provides means and methods to identify, design and develop small molecular scaffolds, such as 5-, 6-, 7-, or 8-membered ring structures; 5-5-, 5-6-, 5-7-, 5-8-, 6-6-, 6-7-, 6-8-, 7-7-, 7-8-, or 8-8-fused bicyclic ring scaffolds, or similar tricyclic fused ring structures that can be placed within the metallopeptide scaffold chemical space, thereby defining a template space, and are then chemically decorated with the key pharmacophore discriminator functional groups or surrogates thereof, all in a sterochemical alignment similar to that of the biologically active metallopeptide, thereby defining a descriptor space.

The invention further provides examples of 5-, 6-, and 8-membered, 5-5-fused, and 5-6-fused bicyclic ring structure scaffolds forming template space and decorated with pharmacophore discriminators identified and deconvoluted from metallopeptides specific for melanotropin receptors, forming relevant descriptor space. The invention further provides methods of synthesis of the desired convoluted ring structure compounds.

The generalized scheme of FIG. 1 illustrates the translation of bioactive pharmacophore descriptors from a metallopeptide to a ring structure, thereby providing a non-metal ion-containing molecular scaffold or template. Thus FIG. 1 depicts a tri-peptide metal ion binding sequence, which includes residues in the L- or D-configuration, or a combination thereof, and which can include modified or unnatural side chains. The metallopeptide can include one or more additional amino acid residues, mimetics or other structures at either or both ends, and any terminal or capping group. As depicted, $R_1$ is conventionally a terminal group and optionally one or more amino acid residues, which may be modified amino acid residues, and $R_2$ and $R_3$ are amino acid side chain moieties or derivatives thereof. Each derivative ring structure shown is designed such that two or more, and preferably all, R groups and other target discriminators, such as terminal groups and the like, occupy the same descriptor space in the ring structure derivatives as is occupied by corresponding elements in the metallopeptide. For example, the relationship of each R group to each other R group, such as in terms of orientation, distance from other R groups, and the like, is the same or substantially similar for both the metallopeptide and the ring structure derivatives. Similarly, the position of each R group relative to the respective ring structures forming a template space, in terms of distances, angles and the like, is the same or substantially similar as between the metallopeptide and the ring structure derivatives. It is to be understood that the peptidomimetics compounds in FIG. 1 are merely illustrative, and that other homocyclic and heterocyclic ring structures, including other atomic constituents and optionally double bonds, are both possible and contemplated. In addition, the ring size may be varied, and any chemically feasible fixed ring structure, including but not limited to bicyclic and tricyclic ring structures, may be employed.

It may further be seen from the foregoing that the selected metallopeptide may be modeled by a derived ring structure by any of a wide variety of parameters, in addition to selection of structurally similar side chains. For example the derived ring structure may have hydrogen bond donors and acceptors, charged centers, aromatic ring centers, hydrophobic centers and the like, each constituting a descriptor space, all modeled on the metallopeptide. In a typical peptide (i.e. a natural or synthetic non-metal polypeptide), there are a wide variety of torsion angles that determine a diverse range of probabilistically-determined secondary and tertiary structures of the peptide. Thus with a typical peptide knowledge of the primary structure does not imply that the secondary or tertiary structure can be determined absent extensive empirical evidence. However, with a metallopeptide the metal ion and metal ion complexing portion of the metallopeptide are conformationally constrained, with a fixed and determined secondary structure resulting in a fixed template space. Because of the metal ion complexation, the torsion angles within and between the residues complexed to the metal ion are fixed and may be determined based upon the type of metal ion employed, including its oxidation state, coordination geometries and the like.

As a result, any metallopeptide, including specifically the portion thereof bound to the metal ion and, to a significant extent, residues adjacent thereto, may be modeled and such information used to perform geometrical shape analysis and to construct a derived ring structure. For example, the location in a three-dimensional construct of hydrogen bond donors and acceptors, positively and negatively charged centers, aromatic ring centers, hydrophobic centers and the like may be determined (including determination of the distance between atoms constituting relevant parts thereof), and such information used to model a derived ring structure. Any of a wide variety of software programs may be employed for such modeling, including programs such as SYBYL (Tripos, Inc.), Alchemy (Tripos, Inc.), Align/Pharmacophore (Accelrys Inc.), Catalyst (Accelrys Inc.), MacroModel (Schrödinger, Inc.), PC-Model (Serena Software), CS ChemOffice (CambridgeSoft Corporation) and other programs known in the field.

The specific stereochemical features of a metallopeptide are due to the stereochemistry of the coordination sphere of the complexing metal ion. The preferred geometry of the coordination sphere of the metal dictates and defines the nature and extent of conformational restriction. In general, most of the metals that may prove useful in this invention have a coordination number of 4 to 6 (and sometimes, but rarely, as high as 8), which implies that there must be residues in the peptide with reactive groups located in a stereocompatible manner establishing a bond with a metal ion of given geometry and coordination sphere. Coordinating groups in the peptide chain include nitrogen atoms of amine, amide, imidazole, or guanidino functionalities; sulfur atoms of thiols or disulfides; and oxygen atoms of hydroxy, phenolic, carbonyl, or carboxyl functionalities. In addition, the peptide chain or individual amino acid residues can be chemically altered to include a coordinating group, such as oxime, hydrazino, sulfhydryl, phosphate, cyano, pyridino, piperidino, or morpholino groups. For a metal with a coordination number of 4, a preferred peptide sequence that binds a metal ion is a three amino acid sequence in which one of the amino acid residues has a side chain with a sulfur-based coordinating group (such as Cys), such residue constituting an $N_1S_1$ ligand. Thus, a three amino acid sequence can provide an $N_3S$, $N_2SO$ or similar ligand, yielding tetradentate coordination of a metal ion utilizing nitrogen and sulfur and, optionally, oxygen atoms.

The choice of metal ion partially determines the structure of the resulting structure. For example, use of a Re ion results in a square pyramidal coordination geometry. Tc (which has substantially similar coordination requirements and chemistries and generally may be substituted for Re in any example herein) similarly results in a square pyramidal coordination geometry. Use of other metal ions, such as Cu, Ni or Zn, results in square planar coordination geometries. Thus while the atomic radius of Re is on the order of 1.37 Å and that of Cu is smaller, on the order of 1.28 Å, the resulting dimensions of the metal coordination group are determined, in large part, by the coordination geometry, and not just by the atomic radius of the metal ion. With metal ions such as Cu, Ni or Zn employing square planar coordination tetradentate geometries, the metal ion and each of the four coordinating atoms (such as S, N or O) are co-planar. However, when employing metal ions such as Re or Tc (which result in square pyramidal coordination tetradentate geometries), the four coordinating atoms (such as S, N or O) are co-planar, but the metal ion is, in the case of Re, about 0.65 Å removed from the plane of the coordinating atoms.

In this invention any of a wide range of metal ions may be employed, but Re and Tc are particularly preferred. Both metals form similar complexes with Cys-containing peptides yielding similar square pyramidal complexes. Re-complexed peptides, however, are chemically more stable than the corresponding Tc-containing peptides. The square planar complexes of Zn and Cu, with the metal ion as well as the four coordinating atoms of the peptide all in one plane, results in a near identical complexation geometry as is obtained with Tc or Re, where the metal ion is projected upwards from the plane of four coordinating atoms of the peptide, notwithstanding the differences in the atomic radius of the metal ions. The net result are metallopeptides that each afford topographic similarities, whether for example Re, Tc, Zn or Cu is employed. The Re-complexed metallopeptides, however, are unique in that the metallopeptides are air and moisture stable, without any need for special or exotic excipients or protecting agents. The Re-complexes can routinely be isolated as solid compounds and are stable as solids and in solutions over a wide pH range, thereby facilitating both analytical characterization and, more importantly, use in both in vitro and in vivo biological experiments over a wide range of conditions. Other metal types, such as Zn-complexes and Cu-complexes, are most conveniently utilized in experiments in a solution form. Zn-complexes and Cu-complexes are extremely easy to form, and essentially are formed in the presence of 1 micromolar to 1 millimolar concentration of the metal ion in an appropriately buffered solution.

The Re- and Tc-complexes are metaloxo complexes, generally and in a preferred embodiment in an oxidation state [V]. The metaloxo core M=O in the metallopeptides may give rise to an isomerism in the core structure. The metal-oxo group may be syn or anti with respect to a chiral amino acid side chain. Since the orientation of the oxo group does not alter the topographic surface created by the amino acid side chains, this isomerism has no effect on the biological activity of the metallopeptides. The metal ion is situated at a location spatially similar to that where turns are stabilized by a hydrogen bond in natural turn structures, and the oxo group thus falls within a space not addressable in natural turn structures. Computer modeling of individual syn- and anti-isomers of metallopeptides have shown that these two structures are completely indistinguishable with respect to each amino acid location, with orientation of the oxo group being the only difference. Thus the template space as between metallopeptides differing only by orientation of the oxo group is generally not functionally distinguishable.

Figure 2:
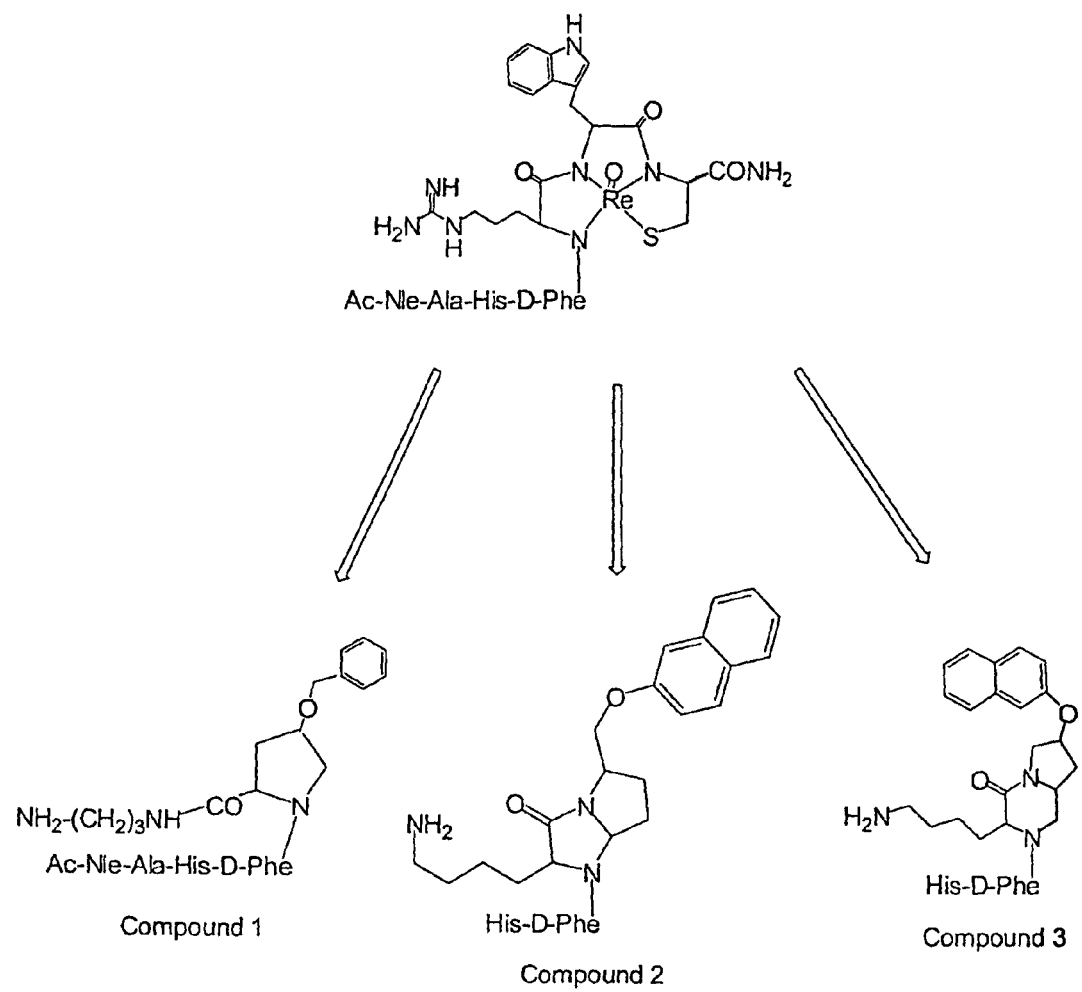
FIG. 2 depicts a scheme of this invention for deriving biologically active peptidomimetics from a metallopeptide specific for a melanocortin receptor, wherein Re depicts a rhenium metal ion.

FIG. 2 depicts information relating to obtaining ring-structure, non-metal small molecules based on melanotropin receptor-specific discriminator elements identified on a potent metallopeptide molecule. The metallopeptide molecule is Re-complexed Ac-Nle-Ala-His-D-Phe-Arg-Trp-Cys-NH$_2$, as shown in FIG. 2, a potent agonist of certain melanotropin receptors identified in International Patent Application Serial No. PCT/US00/16396, Melanocortin Metallopeptide Constructs, Combinatorial Libraries and Applications, filed Jun. 14, 2000, incorporated herein by reference. The key structural information in this metallopeptide is defined by the side chains of Trp, Arg, and D-Phe residues, which are highly constrained on the metal-peptide scaffold. These side chains thus each define a descriptor space, which includes therein the relationship to the template space of the metallopeptide scaffold or ring structure. The rigidity of the structure, therefore, defines the stereochemical relationship of the side chains of Trp, Arg, and D-Phe to one another. Moreover, these discriminating elements are stationed around one of the five-member rings of the tri-cyclic metal-peptide scaffold. This single ring in the metallopeptide thus defines the most relevant template space. Compound 1 of FIG. 2 is a representative derived ring-structure molecule where the identified structural elements defining a descriptor space are decorated on a 5-membered pyrrolidine ring forming a template space, which template space overlaps with and is superimposable on the corresponding 5-membered ring forming a template space in peptide-metal scaffold of ReO complexed Ac-Nle-Ala-His-D-Phe-Arg-Trp-Cys-NH$_2$. During the decoration process, some synthetic compromises can be made to facilitate synthesis of the molecules on small molecular scaffolds. For example, during the development of Compound 1, the indole group was substituted by a phenyl and the arginine side chain was substituted by an aliphatic chain terminating in a primary amino group. As is evident from the biological screening data (see Example 133), Compound 1 is a potent MCR-1 specific compound with full agonistic activity suggesting complete translation of the MCR-1 requirements in the metallopeptide to non-metal containing Compound 1. Similarly the fused 5-5-membered bicyclic scaffold in Compound 2 of FIG. 2 may also be superimposed on two of the three rings on the metal-peptide scaffolds in the metallopeptide. These rings thus define a superimposable template space. A translation of the pharmacophore, with similar synthetic compromises, also resulted in a potent MCR-1 agonist (see Example 180). In Compound 2 there is a 2'-naphthyl group substituting for the indole ring in the metallopeptide. The template in Compound 3 of FIG. 2 is close to that of Compound 2 except that it is a fused 6-5-membered bicyclic system and the 2'-naphthyl group is removed further from the bridge head nitrogen by one more carbon atom. With these differences the translation of same pharmacophore results in an inactive molecule since these differences make this structure non-superimposable on the two relevant rings of the metal-peptide scaffold in the metallopeptide, thereby causing a mismatch in receptor recognition by this molecule. Compound 3 accordingly demonstrated no binding to any melanocortin receptor using the methods of Example 3, and was inactive by the methods of the functional assay of Example 4. On the other hand, successful decoration of the same pharmacophore on a six-membered ring scaffold (see e.g. Examples 11 to 78) shows that it is conceptually possible to use a scaffold fitting in a template space similar to that in the metal and peptide scaffold of the metallopeptide and allow judicious juxtaposition of the descriptor elements in defined descriptor space, thereby leading to potent peptidomimetics based on structural information obtained with use of metallopeptides. These results demonstrate translating receptor-specific molecular descriptors from one rigid scaffold (metal ion-based) to another (non-metal ring-based) utilizing the structural information, stereolocation, and molecular descriptors, including side-chains, based on the metallopeptide.

Clinical Applications. In general, the resulting peptidomimetics of this invention may be employed for any application or use for which the biologically active metallopeptide could be employed. Thus a peptidomimetic of this invention derived from a vasopressin receptor-specific metallopeptide could, for example, be used for treatment of septic shock, hemorrhagic shock, cardiac arrest management such as ventricular fibrillation, and other conditions involving hemodynamics. A peptidomimetic derived from an angiotensin receptor blocker, such as an antagonist, could be used for treatment of high blood pressure, heart failure and the like. A peptidomimetic derived from an oxytocin metallopeptide could be used for inducing labor, treatment of postpartum hemorrhage, modifying emotional behavior and the like.

In the case of melanocortin receptor-specific agents, peptidomimetic compounds of this invention that are MC1-R specific can be used as chemoprevention agents against sun-induced, such as by UV radiation, neoplastic activity in human skin. MC1-R agonist peptidomimetic compounds of this invention may be employed to stimulate epidermal melanocytes to produce melanin as well as to convert pheomelanin to eumelanin. Eumelanin, which is dark brown or black pigmentation, is considered more photo-protective than pheomelanin, which is yellow or red pigmentation. The process of melanogenesis is believed to involve stimulation of MC1-R in epidermal melanocytes, thereby mediating the stimulation of tyrosinase enzymes within these pigment cells, inducing the conversion of tyrosine to dopa and then through dopaquinone to eumelanin. Sun tanning due to direct sun exposure is proposed to result from the same pathway by local production of melanotropic peptide from a POMC gene in the epidermis. Thus stimulation of eumelanin production and conversion of pheomelanin to eumelanin may be a desirable chemoprevention modality in blocking sun- or UV-induced neoplastic activity in skin. A potent, high-affinity and highly selective MC1-R agonist peptidomimetic compound of this invention can accordingly be used as a therapeutic chemoprevention agent for combating harmful sun or UV exposure that induces neoplastic activity in skin melanocytes.

In another embodiment peptidomimetic compounds of this invention that are MC4-R agonists can be used as a therapeutic agent to modify energy metabolism and feeding behavior, including treatment of pathologic obesity and related conditions. Peptidomimetic compounds of this invention that are MC4-R antagonists can also be used as a therapeutic agent in eating disorders, such as treatment of anorexia. Control centers for eating and satiety reside in the hypothalamus. These responses are determined by diverse hormones and soluble factors that signal through specific receptors in the hypothalamus. MC4-R is known to be expressed in the brain, and inactivation of this receptor by gene targeting has resulted in mice with the maturity-onset obesity syndrome that is associated with hyperphagia, hyperinsulinemia and hyperglycemia.

In yet another embodiment, peptidomimetic compounds of this invention may used as therapeutic agents for treatment of sexual dysfunction, including treatment of both male erectile dysfunction and female sexual dysfunction. In yet another embodiment, peptidomimetic compounds of this invention may be used as therapeutic agents for treatment of inflammation, including specifically MC1-R and MC3-R agonist metallopeptides.

In yet another embodiment of the invention, peptidomimetic compounds of this invention that are MC5-R specific can be used as agents to decrease sebum production, and thus may be efficacious in the treatment of acne and related diseases. The peptidomimetic compounds for this application may be conveniently formulated for local administration, as through a gel, lotion, cream or other topical formulation.

The peptidomimetic compounds may be formulated by any means known in the art, including but not limited to tablets, capsules, caplets, suspensions, powders, lyophilized forms and aerosols and may be mixed and formulated with buffers, binders, stabilizers, anti-oxidants and other agents known in the art. The peptidomimetic compounds may be administered by any systemic or partially systemic means known in the art, including but not limited to intravenous injection, subcutaneous injection, administration through mucous membranes, oral administration, dermal administration, skin patches, aerosols and the like.

The invention further provides a pharmaceutical composition that includes a peptidomimetic compound of this invention and a pharmaceutically acceptable carrier. The peptidomimetic compound of this invention may thus be formulated or compounded into pharmaceutical compositions that include at least one peptidomimetic compound of this invention together with one or more pharmaceutically acceptable carriers, including excipients, such as diluents, carriers and the like, and additives, such as stabilizing agents, preservatives, solubilizing agents, buffers and the like, as may be desired. Formulation excipients may include polyvinylpyrrolidone, gelatin, hydroxy cellulose, acacia, polyethylene glycol, mannitol, sodium chloride or sodium citrate. For injection or other liquid administration formulations, water containing at least one or more buffering constituents is suitable, and stabilizing agents, preservatives and solubilizing agents may also be employed. For solid administration formulations, any of a variety of thickening, filler, bulking and carrier additives may be employed, such as starches, sugars, fatty acids and the like. For topical administration formulations, any of a variety of creams, ointments, gels, lotions and the like may be employed. For most pharmaceutical formulations, non-active ingredients will constitute the greater part, by weight or volume, of the preparation. For pharmaceutical formulations, it is also contemplated that any of a variety of measured-release, slow-release or time-release formulations and additives may be employed, so that the dosage may be formulated so as to effect delivery of a peptidomimetic compound of this invention over a period of time.

The peptidomimetic compounds and pharmaceutical compositions of this invention may be administered by injection, which injection may be intravenous, subcutaneous, intramuscular, intraperitoneal or by any other means known in the art. In general, any route of administration by which the peptidomimetic compounds of this invention are introduced across an epidermal layer of cells may be employed. Administration means may include administration through mucous membranes, buccal administration, oral administration, dermal administration, inhalation administration, nasal administration and the like. The dosage for treatment is administration, by any of the foregoing means or any other means known in the art, of an amount sufficient to bring about the desired therapeutic effect.

In general, the actual quantity of peptidomimetic compound of this invention administered to a patient will vary between fairly wide ranges depending upon the mode of administration, the formulation used, and the response desired. This may readily be determined by one of ordinary skill in the art through means such as pharmacokinetic studies, plasma half-life, dose escalation studies, and the like.

The invention is further illustrated by the following non-limiting examples.

EXAMPLE 1

Synthesis and Metal Ion Complexation of Melanocortin Receptor-Specific Metallopeptide The peptide sequence Ac-Nle-Ala-His-D-Phe-Arg-Trp-Cys-NH$_2$ was synthesized using Fmoc chemistry, with side chain functionalities protected using acid labile groups. Rhenium complexation was by treatment with the rhenium transfer agent ReOCl$_3$(PPh$_3$)$_2$ in the presence of a base as generally disclosed in International Patent Application Serial No. PCT/US00/16396. Following rhenium ion complexation, the resulting metallopeptide was tested for melanocortin receptor specificity using the methods of Example 3. It was determined that at 1 μM concentration in a competitive inhibition binding assay that the metallopeptide inhibited binding of 98% of $^{125}$I-NDP-α-MSH to the MC4-R and 91% to the MC1-R. In a cAMP assay as in Example 4 for determination of agonist/antagonist status, it was determined that the metallopeptide was an agonist as to MC1-R, MC4-R and MC-5. The Ki was determined by the method of Example 4, with the following results:

| Ki (nM) | | | |
|---|---|---|---|
| MC1-R | MC3-R | MC4-R | MC5-R |
| 1 | 560 | 28 | 19 |

EXAMPLE 2

Determination of Mass and Nuclear Magnetic Resonance Analysis

The mass values were determined using a Waters Micro-Mass ZQ device utilizing a positive mode. Mass determinations were compared with calculated values and expressed in the form of mass weight plus one (M+1).

Proton NMR data was obtained using a Bruker 300 MHz spectrometer. The spectra were obtained after dissolving compounds in a deuteriated solvent such as chloroform, dimethyl sulfoxide, or methanol as appropriate.

EXAMPLE 3

Determination of Melanocortin Receptor Specificity by Competitive Inhibition

The competitive inhibition binding assay was conducted using membranes prepared from hMC3-R, hMC4-R, hMC5-R, and B-16 mouse melanoma cells (containing MC1-R) using 0.4 nM $^{125}$I-NDP-α-MSH (New England Nuclear, Boston, Mass., USA) in 50 mM HEPES buffer containing 1 mM MgCl$_2$, 2 mM CaCl$_2$, and 5 mM KCl, at pH 7.2. The assay tube also contained a chosen concentration of the test peptidomimetic of this invention, generally 1 μM, for determining its efficacy in inhibiting the binding of $^{125}$I-NDP-α-MSH to its receptor. Non-specific binding was measured by complete inhibition of binding of $^{125}$I-NDP-α-MSH in the assay with the presence of 1 μM α-MSH.

Incubation was for 90 minutes at room temperature, after which the assay mixture was filtered and the membranes washed three times with ice cold buffer. The filter was dried and counted in a gamma counter for remaining radioactivity bound to the membranes. 100% specific binding was defined as the difference in radioactivity (cpm) bound to cell membranes in the absence and presence of 1 μM α-MSH. The cpm obtained in presence of test compounds were normalized with respect to 100% specific binding to determine the percent inhibition of $^{125}$I-NDP-α-MSH binding. Each assay was conducted in triplicate and the actual mean values are described.

EXAMPLE 4

Determination of Agonist/Antagonist Status and Ki

The Ki (nM) of certain peptidomimetics were determined, as was the agonist/antagonist status with respect to MC4-R, Functional evaluation of compounds at melanocortin receptors was performed by measuring the accumulation of intracellular cAMP in HEK-293 cells expressing MC3-R, MC4-R or MC5-R, and in B-16 mouse melanoma cells (containing MC1-R). Antagonistic activity was determined by measuring the inhibition of α-MSH-induced cAMP levels following exposure to the compounds. Cells, suspended in Earle's Balanced Salt Solution containing 10 mM HEPES, pH 7.5, 5 mM $MgCl_2$, 1 mM glutamine, 0.1% albumin and 0.6 mM 3-isobutyl-1-methyl-xanthine, a phosphodiesterase inhibitor, were plated in 96 well plates at a density of $0.5 \times 10^5$ cells per well. Cells were incubated with the test compounds in the presence or absence of α-MSH for 1 hour at 37° C. cAMP levels were measured by EIA (Amersham) in the cell lysates. Data analysis and $EC_{50}$ values were determined using nonlinear regression analysis with Prism Graph-Pad software.

EXAMPLE 5

General Procedure for the Synthesis of Pyrrolidine Type Compounds 1,4-diaminobutane trityl resin (0.1 mmol, Novobiochem) was swollen in DCM for 30 minutes. The solvent was removed and N-Fmoc-O-benzyl-hydroxyproline (0.4 mmol), TBTU (0.4 mmol) and DIEA (0.6 mmol) in NMP was added to the resin. It was agitated under nitrogen for 30 minutes and washed with NMP (2 times) and DCM (2 times). The Fmoc group was removed by treatment of the resin with piperidine (20%) in NMP for 20 minutes. The resin was washed with NMP (3 times) and DCM (3 times). Subsequently, the next desired Fmoc protected amino acid was attached to the resin in the same manner as described above. The capping groups on the N-terminal on carboxylic acids were also coupled in this way. Otherwise, anhydrides were used by agitating the resin with anhydride (6 mmol) in dry pyridine for 1 hour.

After complete assembly of the compound on resin as shown in Scheme 1, the Fmoc group, if present, was removed and the resin washed with NMP (3 times), DCM (3 times), and methanol (3 times). The resin was then thoroughly dried under vacuum. The final compound was removed from the resin by treatment with TIS/TFA/DCM (2 mL; v/v/v=5/50/50) for 1 hour. The organic liquid was evaporated and the residue was purified by HPLC to give the final compound. Mass analysis was conducted to verify the molecular weight of the compound.

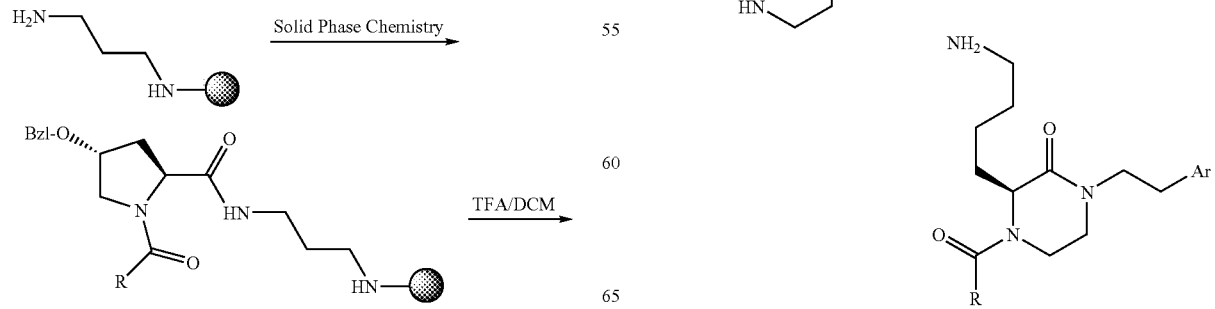

EXAMPLE 6

General Procedures for the Synthesis of piperazin-2-one Compounds

Method A. This method is summarized in Scheme 2. Weinreb AM resin (1.5 mmol, Novobiochem) was swollen in DCM for 1 hour. The Fmoc group was removed by treatment with piperidine (20%) in NMP. The resin was washed with NMP (3 times) and DCM (3 times).

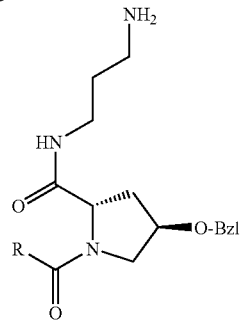

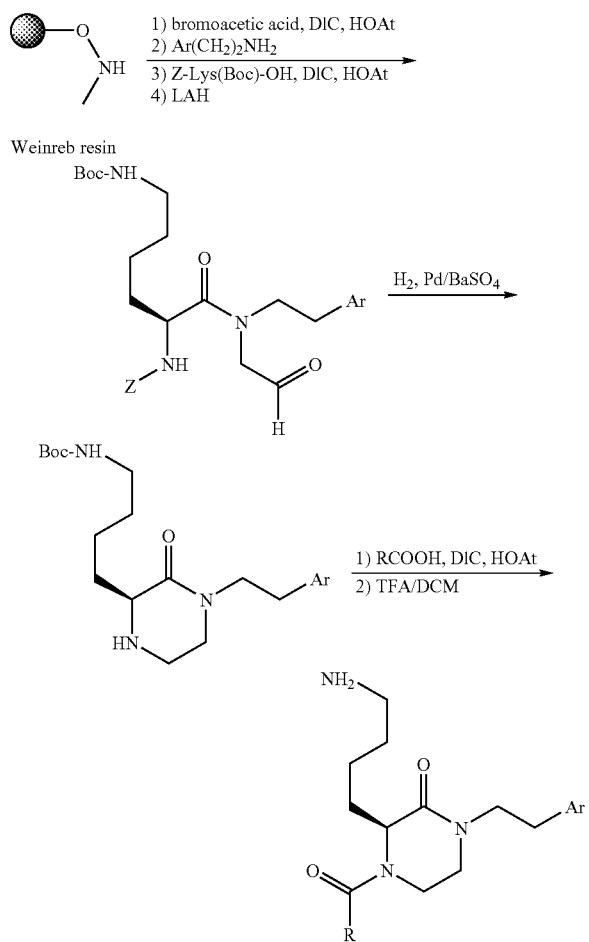

Separately, 2-bromo-acetic acid (7.5 mmol, Aldrich) and HOAt (7.5 mmol, Aldrich) were dissolved in DMF (10 mL) with DIC (7.5 mmol) subsequently added slowly. After stirring for 30 minutes, this solution was added to the prepared resin. The resin mixture was vigorously shaken for 20 hours.

The resin mixture was then washed with DMF (2 times) and DCM (2 times). The desired amine (75 mmol) was then added to this resin in DMSO (16 mL), and the mixture agitated for 24 hours and then washed with DMSO (2 times), DMF (2 times) and DCM (2 times). The secondary amine formed on the resin was coupled with Z-Lys(Boc)-OH (15 mmol) using HOAt (15 mmol) and DIC (15 mmol) in DCM/DMF (25 mL; v/v=4/1) for 24 hours. The resin was washed with DMF (2 times), DCM (2 times), methanol (2 times) and ether, and then dried under vacuum overnight.

The dried resin was swollen in dry THF (20 mL) for 1 hour under nitrogen. To this a solution of LAH, THF (1.875 mmol) was slowly added at 0° C. After stirring for an additional 1 hour, the reaction was quenched with aqueous potassium hydrogen sulfate (1.25 eq). The resin was removed by filtration and washed with DCM (3 times). The combined filtrate was evaporated and re-extracted in ether and washed with brine. The ether layer was dried over sodium sulfate and ether removed to yield a crude aldehyde compound residue that was dried under vacuum and characterized by mass analysis. The crude compound was dissolved in methanol (10 mL) and stirred under hydrogen (1 atm.) over a catalytic amount of palladium (5%) on barium sulfate for 2 days. The reaction was monitored by mass spectrometry to determine complete disappearance of aldehyde and to confirm the presence of the reduced compound, piperazin-2-one. This crude compound was used for the next step without further purification.

The piperazin-2-one was coupled with the appropriate amino acid derivative (2 eq) using HOAt (2 eq) and DIC (2 eq) in DMF overnight at room temperature. Subsequent amino acids were coupled in a similar fashion. Flash chromatography (in ethyl acetate/hexane, v/v=1/2) was used to give the final fully protected product. In appropriate instances, the Fmoc groups were removed by treatment with diethyl amine (20%) in ethyl acetate, and Boc groups were removed by treatment with TFA (30%) in methylene chloride for 1 hour. The final compounds were obtained in pure form after purification by HPLC.

Method B. Method B is summarized in Scheme 3. To a solution of compound A (organic carboxylic acid) and HOAt (1 eq) in dry DMF, 1-(3-dimethylaminopropyl)-3-ethylcarbodiimide hydrochloride (2 eq) was added. The mixture was stirred at room temperature for 30 minutes. Ethanolamine (2 eq) was added and the reaction allowed to proceed for 16 hours. The reaction mixture was poured into water and extracted by ethyl acetate (2 times). The organic layer was washed with 1 N hydrochloric acid (2 times), 1 N sodium hydroxide (2 times), brine and dried over sodium sulfate. After evaporation, the product (B) was purified on a silica gel column with methanol (10%) in methylene chloride.

Acetic acid (5 eq) in dioxane was added slowly to a mixture of Compound B (1 eq) and sodium borohydride (5 eq) also in dioxane. The solution was refluxed for 2 hours and the reaction quenched with water. The product was extracted from ether by 1 N hydrochloric acid. The solution was adjusted to pH 11 with KOH, extracted with ether (3 times), and the organic layer dried over sodium sulfate to obtain compound C used for the next reaction without further purification.

The desired N-protected amino acid (1 eq), was added to HOAt (1 eq) and DIC (1 eq) in DMF and the resulting solution stirred for 30 minutes. Compound C was then added and the mixture stirred overnight. After evaporating solvent, compound D was obtained by silica gel column purification.

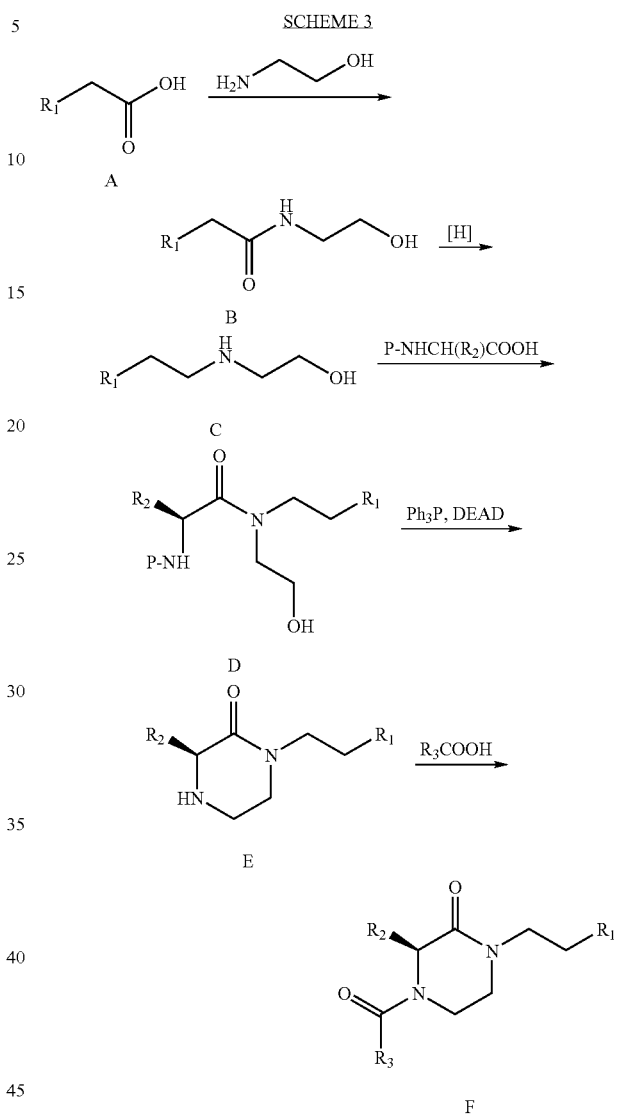

The protecting group P (Fmoc or Cbz) was removed by either diethyl amine (20%) in ethyl acetate or by hydrogen catalyzed with palladium (10%) on carbon. The resulting compound was dissolved in dry THF containing TPP (3 eq). DEAD (3 eq) in THF was slowly added. The reaction was stirred for an additional 12 hours, the solvent evaporated and the product (E) was purified on silica gel column by ethyl acetate/methanol (v/v=4/1).

The final compound F was synthesized as described in Example 6, Method A.

Method C. The reaction scheme is shown in Scheme 4. A mixture of diethanol amine (1 eq) and benzaldehyde (1 eq) in benzene in a round-bottom flask equipped with a Dean-Stark trap was refluxed azeotropically for 4 hours, followed by evaporation of the solvent. The resulting product (B) was obtained as colorless oil, which was used for the next reaction.

Compound B (1 eq), 2-naphthol (1.3 eq) and TPP (1.5 eq) were dissolved in toluene (80 mL). DEAD (1.1 eq) in toluene was added dropwise at 0° C. under nitrogen. The reaction mixture was stirred at room temperature overnight. Completion of the reaction was monitored by TLC. Upon completion of the reaction, concentrated HCl (1 mL) was added to the reaction mixture and stirred at 50° C. for 1 hour. The formed precipitation was collected by filtration and washed twice with DCM. The collected white solid was dissolved in 1 N sodium hydroxide (20 mL) and the solution extracted with ethyl acetate (4×30 mL). The combined organic layers were washed with water (3 times), brine (1 time), dried with magnesium sulfate, and the solvent evaporated in vacuo to yield the product (D) as a white crystal solid. The final compound E was synthesized using Example 6, Methods A and B.

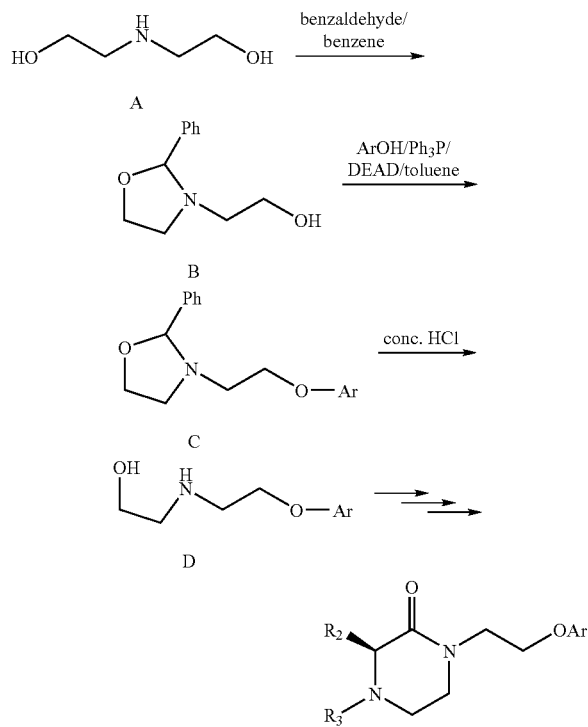

EXAMPLE 7

General Procedure for the Synthesis of hexahydro-pyrrolo[1,2-a]pyrazin-4-one

This method is shown in Scheme 5. To a solution of N-(tert-butoxycarbonyl)-O-benzyl-hydroxyproline in DCM, NMM (1 eq) and iso-butyl chloroformate (1 eq) were added at −15° C. and stirred for 30 minutes. A solution of N,O-dimethylhydroxylamine hydrochloride (1.5 eq) and NMM (1.5 eq) was added to the mixture, and after 30 minutes the mixture was allowed to attain room temperature and stirred overnight. Solvent was evaporated and residue purified on a silica gel column using an ethyl acetate-hexane mixture (v/v=2/1) to yield N-(tert-butoxycarbonyl)-O-benzyl-hydroxyproline dimethylhydroxamide. The O-benzyl group was removed using palladium (10%) on carbon in methanol under hydrogen (1 atm.) for 10 hours. After filtration, the solvent was evaporated and the resulting compound was used for next step reaction after drying under vacuum. The formation of an ether bond was accomplished by either of the following Method A or Method B.

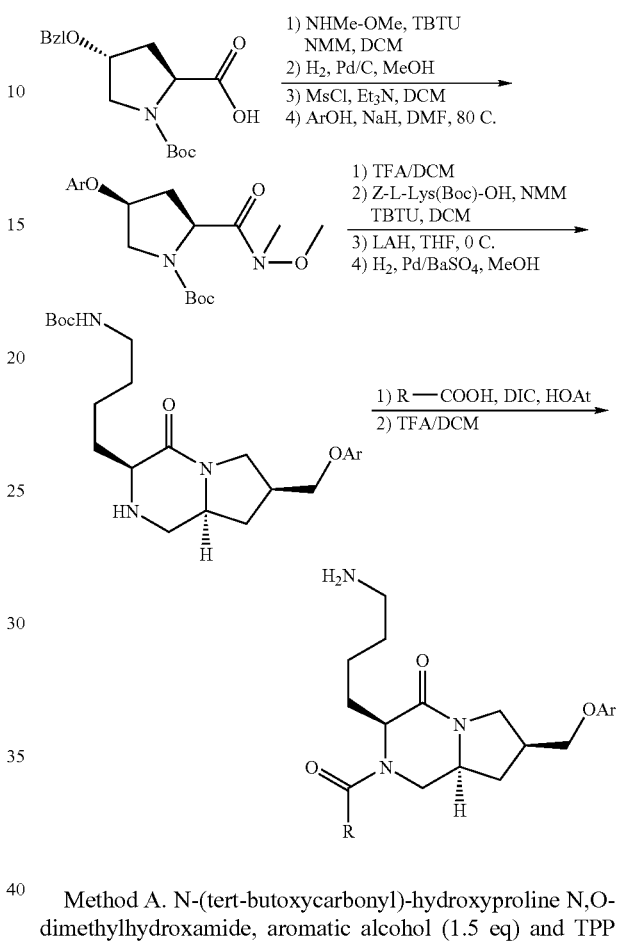

Method A. N-(tert-butoxycarbonyl)-hydroxyproline N,O-dimethylhydroxamide, aromatic alcohol (1.5 eq) and TPP were dissolved in THF. To this solution DEAD (1.5 eq) in THF was added dropwise at 0° C. After 12 hours, the solvent was evaporated, the residue taken in ethyl acetate and washed successively with 1 N sodium hydroxide, water and brine followed by drying over sodium sulfate. Silica gel column chromatography using ethyl acetate and hexane (v/v=2/1) yielded purified O-substituted N-(tert-butoxycarbonyl)-hydroxyproline N,O-dimethylhydroxamide.

Method B. Methanesulfonyl chloride (2 eq) was slowly added at 0° C. to a DCM solution of N-(tert-butoxycarbonyl)-hydroxyproline N,O-dimethylhydroxamide and TEA (2 eq). The reaction mixture was stirred for an additional 10 minutes and allowed to attain room temperature with continued stirring for an additional 45 minutes. The solvent was then evaporated and residue taken in water. It was extracted with ethyl acetate (twice) and the combined organic layer was washed with brine and dried over sodium sulfate. The solvent was evaporated and residue dried under vacuum to give O-mesyl N-(tert-butoxycarbonyl)-hydroxyproline N,O-dimethylhydroxamide. The yield from this reaction approached 100%. To a suspension of sodium hydride (2 eq) in DMF was added an aromatic alcohol (2 eq) taken in DMF under vigorous stirring. After completion of the hydrogen release, the solution was added to the DMF solution of O-mesyl N-(tert-butoxycarbonyl)-hydroxyproline N,O-dimethylhydroxamide and stirred for 16 hours. The reaction temperature then was raised to 90° C. with continued stirring for 24-48 hours. After cooling, the reaction mixture was poured into water and extracted twice with ethyl acetate. The combined organic layer was washed with water (twice), brine (once), and dried over sodium sulfate. The solvent was evaporated and product purified as described in Example 7, Method A.

Following addition of the ether bond using the above methods, the tert-butoxycarbonyl group from O-substituted N-(tert-butoxycarbonyl)-hydroxyproline N,O-dimethylhydroxamide was removed by treatment with TFA (25%) in DCM for 1 hour. After evaporating the solvent, the compound was dissolved in DCM and NMM (1 eq) added. The compound was mixed with a reaction mixture obtained separately by slowly mixing isobutyl chloroformate at −15° C. for 30 minutes with a DCM solution of Z-Lys(Boc)-OH (1 eq) and NMM (1 eq). The combined solution was then stirred at room temperature for an additional 16 hours. After evaporating the solvent, the residue was purified on a silica gel column with ethyl acetate as an eluant.

O-substituted N-(N-benzyloxycarbonyl-N'-tert-butoxycarbonyl-lysyl)-hydroxyproline N,O-dimethylhydroxamide obtained above was dissolved in dry THF and the solution cooled to 0° C. LAH (1.25 eq) in THF was slowly added and the reaction mixture stirred for an additional 30 minutes. The reaction was quenched with aqueous potassium hydrogen sulfate (1.75 eq). The solution was diluted with ether and washed with 1 N hydrogen chloride, saturated sodium hydrogen carbonate, and brine. The organic layer was dried over sodium sulfate and solvent evaporated to dryness. The resulting aldehyde derivative was used without purification in the next reaction.

The product from the preceding step was dissolved in methanol and a catalytic amount of palladium (5%) in barium sulfate was added and the mixture hydrogenated at 1 atm. of hydrogen gas for 3 days. The reaction was monitored by mass analysis. The resulting mixture was filtered and the solvent evaporated to give 2,7-disubstituted hexahydro-pyrrolo[1,2-a]pyrazin-4-one. This compound was used further without purification.

The 2,7-disubstituted hexahydro-pyrrolo[1,2-a]pyrazin-4-one was coupled with desired amino acid residues (2 eq) using HOAt (2 eq) and DIC (2 eq) in DMF overnight at room temperature. Other amino acids derivatives were coupled in a similar fashion. The final fully protected compound was purified by flash chromatography (ethyl acetate/hexane, v/v=1/2). In appropriate instances, the Fmoc group was removed by treatment with diethyl amine (20%) in ethyl acetate while Boc groups were removed by treatment with TFA (30%) in DCM for 1 hour. The final compounds were obtained in pure form after their purification by HPLC.

EXAMPLE 8

General Procedure for the Synthesis of Substituted hexahydro-pyrrolo[1,2-a]imidazol-3-one The general method is shown in Scheme 6. TBTU (1 eq) was added to a solution of N-(tert-butoxycarbonyl)-glutamine benzyl ester and NMM (1 eq) in dry DCM and the mixture stirred at room temperature for 30 minutes. A mixture of N,O-dimethylhydroxyamine hydrochloride (1.5 eq) and NMM (1.5 eq) in DCM was separately stirred for 30 minutes. These two mixtures were combined and stirred at room temperature for 18 hours. The organic solvent was evaporated, the residue was loaded on a flash chromatograph column and eluted with ethyl acetate/hexane (v/v=2/1) to give N-(tert-butoxycarbonyl)-5

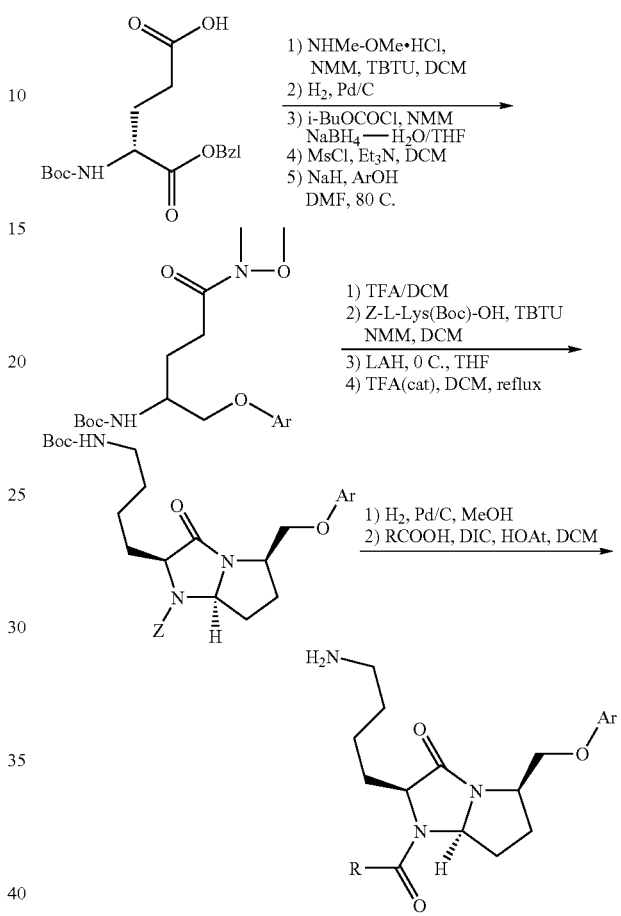

-(N,O-dimethyl-hydroxamide)-glutamine benzyl ester. N-(tert-butoxycarbonyl)-5-(N,O-dimethyl-hydroxyamide)-glutamine benzyl ester and a catalytic amount of palladium (10%) in carbon taken in methanol was stirred under 1 atm. hydrogen overnight at room temperature. After filtration and evaporation of solvent, a clear oily product was obtained which was used as it is in next step.

To a solution of N-(tert-butoxycarbonyl)-5-(N,O-dimethyl-hydroxamide)-glutamine (3.9 g, 13.45 mmol) and NMM (1 eq) in THF at −15° C. was slowly added a THF solution of isobutyl chloroformate (1 eq). The mixture was stirred at this temperature for an additional 30 minutes. A solution of sodium borohydride (1.5 eq) in water was added in portions to the THF solution. After 20 minutes, the temperature was raised to room temperature and stirred for another 1 hour. The organic solvent was evaporated and the residue was purified on a column (10% methanol in DCM) to give N-(tert-butoxycarbonyl)-5-(N,O-dimethyl-hydroxamide)-glutaminol.

To N-(tert-butoxycarbonyl)-5-(N,O-dimethyl-hydroxamide)-glutaminol and TEA (2 eq) in DCM at 0° C. was added methanesulfonyl chloride (2 eq) also in DCM. The solution was stirred at 0° C. for 20 minutes and at room temperature for an additional 45 minutes. The solvent was evaporated and the product extracted from water with ethyl acetate. The organic layer was washed with water and brine and dried over sodium sulfate. After removing solvent, the yield of mesylated product approached 100%.

Sodium hydride (1.5 eq) washed with hexane and taken in dry DMF was mixed slowly with an aromatic alcohol (1.5 eq) at room temperature. The solution was stirred for 1 hour until no hydrogen was released. The mesylated compound in DMF was mixed with the above compound and stirred at room temperature for 24 hours. The solution was subsequently heated at 90° C. for an additional 24 hours. After cooling, the solution was poured into water and extracted twice with ethyl acetate. The combined organic layer was washed with water, brine and dried over sodium sulfate. The organic solvent was removed and the residue was purified on a silica gel column eluted by ethyl acetate/hexane (v/v=2/1) to give O-alkylated N-(tert-butoxycarbonyl)-5-(N,O-dimethyl-hydroxamide)-glutaminol.

The compound synthesized in the preceding step was stirred in TFA/DCM (v/v=1/4) for 1 hour. The solvent was removed and residue dried under vacuum. The residue was mixed with NMM (4 eq) in DCM. Separately, a DCM solution of Z-Lys(Boc)-OH (2 eq) and NMM (2 eq) was mixed with TBTU (2 eq) and stirred for 30 minutes. These two solutions were combined and stirred overnight at room temperature. After evaporating solvent and purification on an ethyl acetate column, O-alkylated N-(N-benzyloxy-N'-tert-butoxycarbonyl-L-lysyl)-5-(N,O-dimethyl-hydroxamide)-glutam inol was obtained in purified form.

O-alkylated N—(N-benzyloxycarbonyl-N'-tert-butoxycarbonyl-L-lysyl)-5-(N,O-dimethyl-hydroxamide)-glutaminol was dissolved in dry THF. The solution was cooled to 0° C. under nitrogen atmosphere. To this solution was slowly added LAH (1 M in THF, 1.25 eq). The solution was stirred at this temperature for 30 minutes and the reaction stopped by adding potassium hydrogen sulfate (1.5 eq) in water. After stirring for 30 minutes the solvent was removed and the residue re-dissolved in ether. The organic phase was washed with 1 N hydrochloric acid, saturated sodium hydrogen carbonate and brine. The ether layer was dried over sodium sulfate. Solvent was removed to yield an aldehyde derivative which was used for the next reaction without further purification.

The aldehyde derivative was dissolved in DCM containing a catalytic amount of TFA and the solution refluxed for 5 hours. After removing solvent, the residue was purified on a column with DCM/acetone (v/v=8/1) to give 2,5-substituted 1-benzyloxycarbonyl-hexahydro-pyrrolo[1,2-a]imidazol-3-one.

2,5-substituted 1-benzyloxycarbonyl-hexahydro-pyrrolo[1,2-a]imidazol-3-one was dissolved in methanol and a catalytic amount of palladium (10%) on carbon was added. The mixture was stirred under hydrogen (1 atm.) overnight. After filtration and evaporation of solvent, the residue was dried under vacuum to give 2,5-substituted hexahydro-pyrrolo[1,2-a]imidazol-3-one. A DMF solution containing a desired Fmoc protected amino acid (2 eq) and HOAt (2 eq) was mixed with DIC (2 eq), stirred for 10 minutes and added to the 2,5-substituted hexahydro-pyrrolo[1,2-a]imidazol-3-one. After 24 hours at room temperature, DMF was removed and the residue was purified on a silica gel column to give 2,5-substituted hexahydro-pyrrolo[1,2-a]imidazol-3-one coupled at 1-position with the Fmoc protected amino acid. The Fmoc group was removed by stirring the compound in diethyl amine/ethyl acetate (v/v=1/4) at room temperature for 12 hours. The solvent was removed under vacuum to yield a residue that was used without further purification. It was mixed with a reaction mixture obtained separately by treating a desired substituted acid (2 eq) and NMM (2 eq) with TBTU (2 eq) in DMF for 10 minutes. The combined reaction mixture was stirred for an additional 24 hours. The solvent was removed and the final fully protected compound was purified by flash chromatography. In appropriate instances, Fmoc groups were removed by treatment with 20% diethyl amine in ethyl acetate while Boc groups were removed by treatment with 30% TFA in DCM for 1 hour. The final compounds were obtained in pure form after purification by HPLC.

EXAMPLE 9

Synthesis of 1,4-benzodiazepine Compounds

The synthesis of 1,4-benzodiazepine compounds were mainly based on the methods described by Jonathan A. Ellman et al (*J Am. Chem. Soc.*, 1995, 117, 3306-3307). Modifications were made at certain steps in order to obtain the desired groups as shown in Scheme 7.

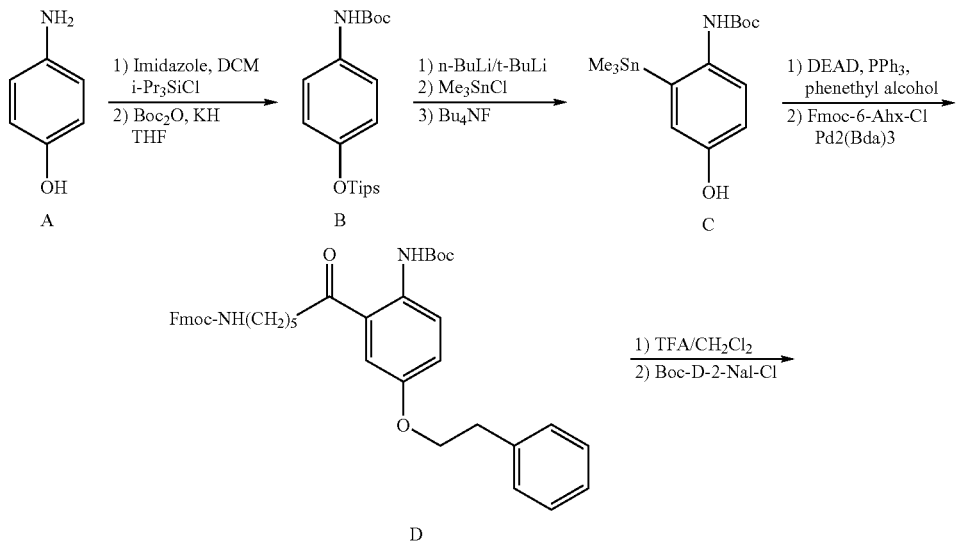

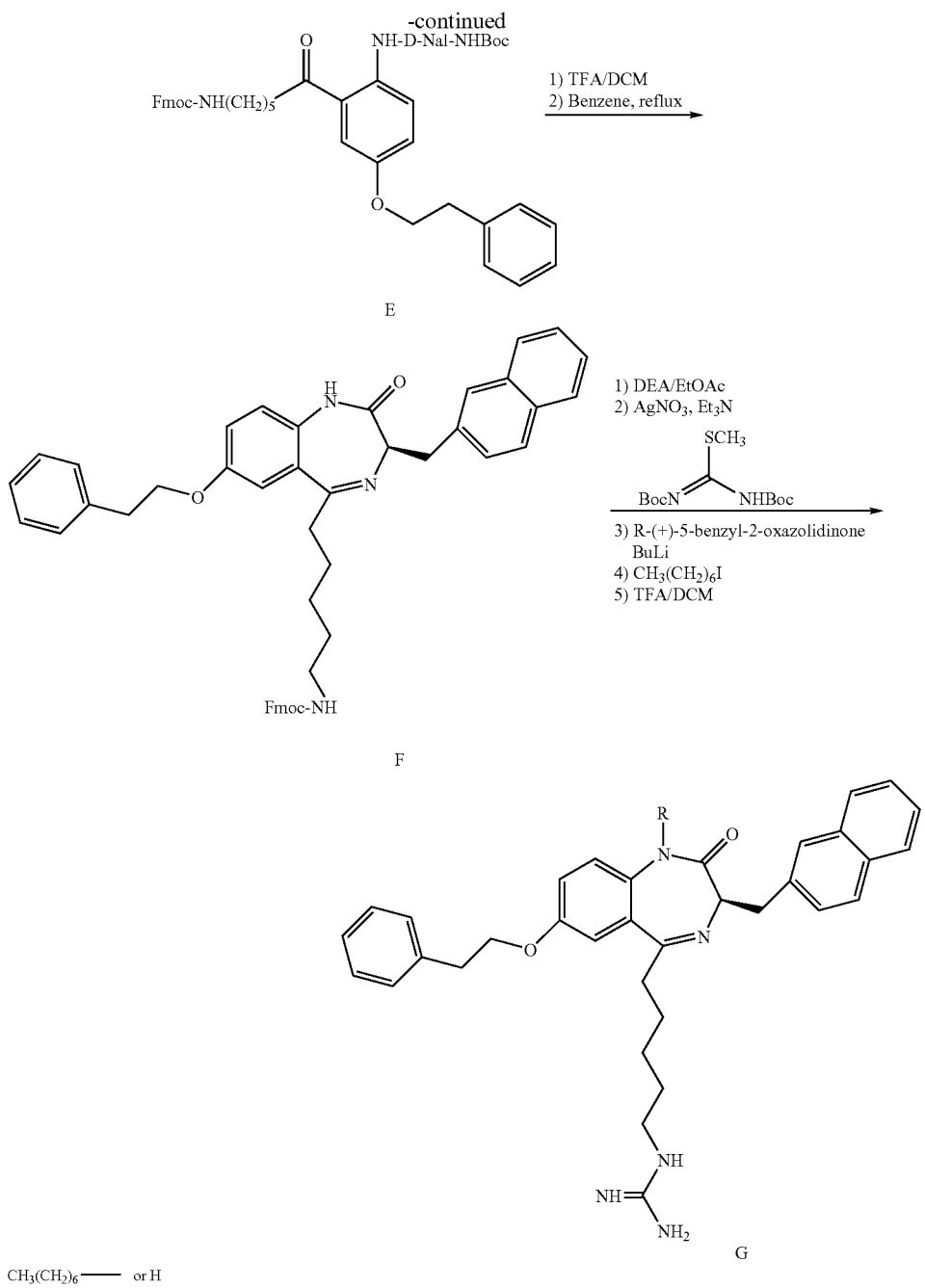

R = CH₃(CH₂)₆— or H

To a mixture of 4-aminophenol (A) (1 eq), imidazole (2 eq) in methylene chloride was added triisopropylsilyl chloride (2.6 eq) at 0° C. The solution was stirred for 1 hour, diluted with methylene chloride, washed with water and brine, and dried over magnesium sulfate. The solvent was evaporated and the product was purified on a silica gel column.

To the resulting product (1 eq) and di-t-butyl dicarbonate (1 eq) in THF was added potassium hydride in portions (2.3 eq) at 0° C. The mixture was stirred 30 minutes at 0° C. and 4 hours at room temperature. Ethyl acetate (100 mL) was added to the mixture and the reaction quenched with water. The mixture was extracted with water, washed with brine, dried over magnesium sulfate, and subjected to evaporation resulting in Product B which was purified by flash chromatography.

To a solution of B in dry THF (1 eq) at −78° C. was added n-butyl lithium (1.1 eq), and then t-butyl lithium (1.3 eq) was added slowly. The temperature was raised to −10° C., stirred for 2 hours and cooled to −78° C. again. Trimethytin chloride (1.6 eq) was added and the mixture stirred at room temperature for 1 hour. The reaction solution was diluted with ethyl acetate and washed with water, brine and dried over magnesium sulfate. After evaporation of solvent the product was purified by flash chromatography.

To the product (1 eq) in THF was added tetrabutylammonium fluoride (1.25 eq). The reaction completed immediately and was quenched with ethyl acetate. The solution was washed with water, brine and dried over magnesium sulfate. After evaporation of solvent the resulting product C was used for the next reaction without further purification.

To a solution of compound C (1 eq), phenethyl alcohol (1.2 eq) and TPP (1.2 eq) was added diethyl azodicarboxylate (1.2 eq) slowly at 0° C. The mixture was stirred overnight at room temperature. After evaporation of solvent the product was purified on a silica gel column.

To a solution of fluorenylmethoxycarbonyl-N-6-aminohexanoic acid (1 eq) in benzene was added oxalyl chloride (1.8 eq) and 1 drop of DMF. The mixture was stirred overnight and evaporated the next day with benzene. The procedure was repeated and dried under vacuum to give a yellow solid, Fluorenylmethoxycarbonyl-N-6-aminohexanoyl chloride, which was used for the next reaction.

To a solution of this compound (1 eq) tris(dibenzylidineacetone)dipalladium (7% eq) in dry THF was added fluorenylmethoxycarbonyl-N-6-aminohexanoyl chloride in THF slowly. The color of reaction turned dark and the reaction was stirred overnight. Precipated palladium was removed by filtration through CELITE® filter media (Celite Corporation). Column purification gave compound D.

Compound D was dissolved in methylene chloride and TFA (v/v=1/1), the reaction allowed to continue for 1 hour, and the solvent removed. The resulting residue was thoroughly dried under vacuum. To a methylene chloride solution of Boc-D-2-naphthylalanine (4 eq) and triethylamine (4 eq) was added cyanuric chloride (2 eq). The mixture was stirred for 3 hours to form acid chloride. To a solution of the dried residue and 2,6-di-t-butyl-4-methylpridine the acid chloride solution was slowly added. Additional stirring for 2 days and subsequent work-up and purification on column gave the desired product E.

Compound E was dissolved in methylene chloride and TFA (v/v=1/1) for 1 hour and the solvent removed. Benzene was added and the mixture was refluxed for 2 hours. After cooling and evaporation of solvent, the resulting compound F was used for the next reaction without purification. The fluorenylmethoxycarbonyl group on compound F was removed by diethylamine (20%) in ethyl acetate, with the reaction monitored by TLC. Upon completion of the reaction the solvent was evaporated and the residue dried under vacuum. The residue was dissolved in acetonitrile and TFA (1.5 eq), 1,3-bis(t-butoxycarbonyl)-2-methyl-2-thiopseudourea (1 eq) and silver nitrate (1.5 eq) were added. The mixture was stirred overnight, solvent evaporated the next day and purified by flash chromatography.

To this purified compound in dry THF at 0° C. was added pre-made lithiated 5-benzyl-2-oxazolidinone (4 eq) in THF. The solution was stirred for 1 hour. Iodoheptane (4 eq) was then added, the reaction temperature raised to room temperature and the mixture stirred overnight. After evaporation of solvent the product was purified by flash chromatography. The compound was stirred in methylene chloride and TFA (v/v=1/1) for 1 hour. Evaporation of solvent resulted in product G.

EXAMPLE 10

Synthesis of Piperazine Type Compounds

The general method is shown in Scheme 8.

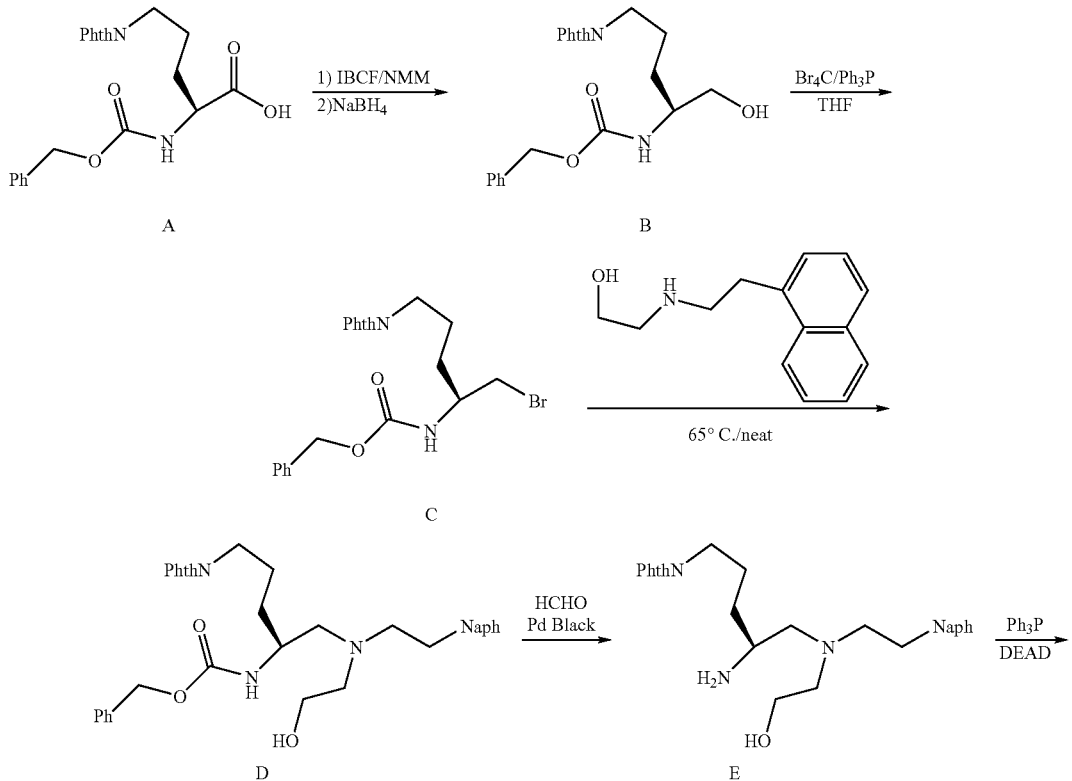

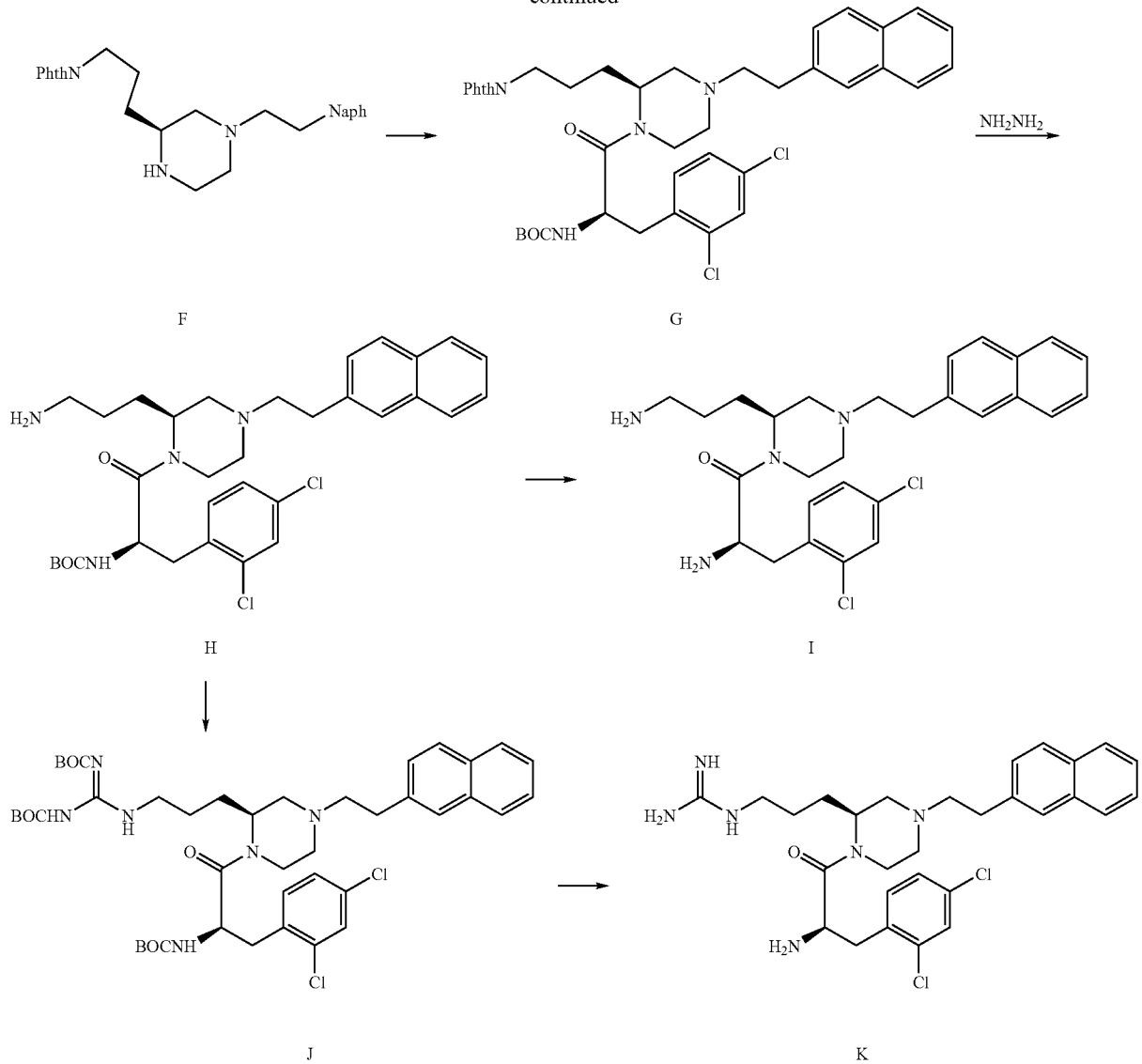

2-Benzyloxycarbonylamino-5-phthalimido-pentanoic acid (A) was made of a mixture of Z-ornithine (1.33 g, 5.0 mmol), N-carethoxy-phthalimide (1.10 g, 5.0 mmol), and triethylamine (1.0 mL, 6.0 mmol) in 10 mL of dry THF refluxed overnight, with the solvent was evaporated in vacuo. The residue was dissolved in ethyl acetate, and washed successively with 1 N HCl, water, and saturated NaCl solution, then dried (MgSO$_4$) and evaporated in vacuo to afford the crude product (2.2 g), which was used as a starting material for the next reaction without further purification.

The crude product (A) was dissolved in 5 mL of THF and to the solution was added NMM (0.44 mL). The solution was cooled down to −15° C. with a salt-ice bath, and isobutyl chloroformate (0.52 mL, 1 eq) was added. After 10 minutes, the reaction mixture was filtered to remove formed salt solid. The solid was washed twice with adequate amounts of THF. The filtrate was cooled down to −10° C. and to it was added NaBH$_4$ (0.23 g, 1.50 eq) in 2 mL of water. The reaction mixture was stirred for another 15 minutes, and then concentrated in vacuo. The residue was dissolved in ethyl acetate and washed successively with 10% citric acid, saturated NaHCO$_3$, H$_2$O and saturated NaCl, and then dried (MgSO$_4$) and concentrated in vacuo. The crude product was purified with column chromatography eluted with EtOAc:hexanes=1:1. The purified product [4-Phthalimido-1-hydroxymethyl-butyl]-carbamic acid benzyl ester (B) was obtained as a white solid, 1.1 g (58%).

At −20° C. under N$_2$ to the suspension of B (253 mg, 0.66 mmol) and triphenylphosphine (260 mg, 1.5 eq) in toluene was added tetrabromocarbon (242 mg, 1.1 eq). The ice bath was let expire and the reaction mixture was stirred at room temperature overnight. The reaction mixture was concentrated in vacuo and the crude product was purified with column chromatography eluted with hexanes: EtOAc=2:1. The purified product [1-Bromomethyl-4-phthalimido-butyl]-carbamic acid benzyl ester (C) was obtained as a white solid, 263 mg (99%).

A mixture of C (400 mg, 0.90 mmol) and the amine (400 mg, 1.86 mmol) in 2 mL of dichloromethane was stirred at 65° C. The solvent was let evaporate and the dried reaction mixture was heated at 65° C. for 2 hours. The formed crude product was purified with column chromatography (eluted with hexanes:ethyl acetate=1:2). The product (4-Phthalimido-1-{[(2-hydroxy-ethyl)-(2-naphthalen-2-yl-ethyl)-amino]-methyl}-butyl)-carbamic acid benzyl ester (D) was obtained as a white solid, 260 mg (50%).

At room temperature under nitrogen a mixture of D (240 mg, 0.41 mmol) and palladium black (80 mg) in 21 mL of 4% HCHO in methanol was stirred vigorously for one hour. The reaction mixture was filtered and the filtrate was neutralized with saturated NaHCO$_3$. The methanol was evaporated and the residue was dissolved in ethyl acetate and washed successively with saturated NaHCO$_3$, water and saturated NaCl, then dried (MgSO$_4$) and evaporated. The product, 2-{4-Amino-5-[(2-hydroxy-ethyl)-(2-naphthalen-2-yl-ethyl)-amino]-pentyl}-isoindole-1,3-dione (E) was collected as a white solid, 160 mg (88%).

At 0° C. under nitrogen to the mixture of E (150 mg, 0.34 mmol) and triphenylphosphine (133 mg, 1.5 eq) in 10 mL of anhydrous THF was added diethyl azodicarbonate (65 mg, 1.1 eq) in 1 mL of anhydrous THF. After stirring at room temperature for 4 hours, the reaction mixture was evaporated in vacuo and the crude was purified with column chromatography. The product, 2-{3-[4-(2-Naphthalen-2-yl-ethyl)-piperazin-2-yl]-propyl}-isoindole-1,3-dione (F), was obtained as a yellowish solid, 42 mg (29%).

To a mixture of F (42 mg, 0.10 mmol) and BOC-D-2,4-dichlorophenylalanine (66 mg, 2 eq) in 0.4 mL of 0.5 M HOAt in DMF and 0.5 mL of anhydrous DMF was added diisopropylcarboimide (24 mg, 2 eq). The reaction mixture was stirred at room temperature overnight. The solvent was evaporated in vacuo and the crude was purified with column chromatography (eluted with hexanes:ethyl acetate=1:2). The purified product, {1-(2,4-Dichloro-benzyl)-2-[2-[3-phthalimido-propyl]-4-(2-naphthalen-2-yl-ethyl)-piperazin-1-yl]-2-oxo-ethyl}-carbamic acid tert-butyl ester (G) was obtained as white solid, 30 mg (40%).

A solution of G (30 mg) in 10 mL of 0.2 M hydrazine in methanol was stirred at room temperature for 19 hours. MS showed no starting material left in the reaction mixture. The reaction mixture was evaporated and co-evaporated with methanol three times and ethyl acetate once, then dried under high vacuum for 2 days. The crude product, [2-[2-(3-Amino-propyl)-4-(2-naphthalen-2-yl-ethyl)-piperazin-1-yl]-1-(2,4-dichloro-benzyl)-2-oxo-ethyl]-carbamic acid tert-butyl ester (H), (~30 mg) was used for the next reaction without further purification.

10 mg of the crude product H was treated with 3 mL of 33% TFA in dichloromethane at room temperature for 2.5 hours. The solvents were removed by evaporation and the crude product was purified by HPLC (10-90-60, in an acetonitrile-water gradient flow). After lyophilization of the collected fractions, the product 2-Amino-1-[2-(3-amino-propyl)-4-(2-naphthalen-2-yl-ethyl)-piperazin-1-yl]-3-(2,4-dichloro-phenyl)-propan-1-one (I) was obtained as white solid, 2.1 mg (purity>90% by HPLC).

Alternatively, 20 mg (0.033 mmol) of the crude product H was reacted with 1,3-bis(tert-butoxycarbonyl)-2-methyl-2-thiopseudourea (10 mg, 1.1 eq) and silver nitrate (6 mg, 1.1 eq) and NMM (2.2 eq) in 5 mL of acetonitrile at room temperature for 24 hrs, followed by evaporation to remove the solvent and column chromatography purification to afford 4.5 mg of the product [2-[2-[3-(N', N''-Di-tert-butoxycarbonyl-guanidino)-propyl]-4-(2-naphthalen-2-yl-ethyl)-piperazin-1-yl]-1-(2,4-dichloro-benzyl)-2-oxo-ethyl]-carbamic acid tert-butyl ester (J). Product J (4.5 mg) was treated with 33% TFA in DCM at room temperature for 2 hours and the reaction mixture was concentrated and purified with HPLC to give 1.05 mg {1-(2,4-Dichloro-benzyl)-2-[2-(3-guanidino-propyl)-4-(2-naphthalen-2-yl-ethyl)-piperazin-1-yl]-2-oxo-ethyl}-carbamic acid tert-butyl ester (K).

EXAMPLE 11

A compound of the following structure:

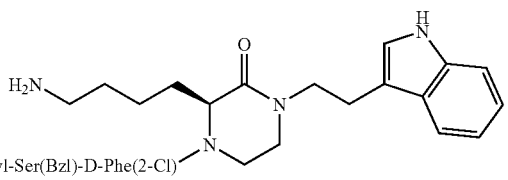

Heptanoyl-Ser(Bzl)-D-Phe(2-Cl)

was synthesized by the general method of scheme 2 as set forth in Example 6. The molecular weight was determined to be 785.0 ESI-MS (M+1) by the method of Example 2. ($^1$H NMR, CD$_3$OD) δ: 0.8-1.9 (m, 17H), 2.25 (m, 2H), 2.75-3.25 (m, 8H), 3.35-4.05 (m, 6H), 4.55 (m, 3H), 4.9 (m, 1H), 5.3 (m, 1H), 6.9-7.6 (m, 14H). Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 96% | 51% | 99% | 82% |

EXAMPLE 12

A compound of the following structure:

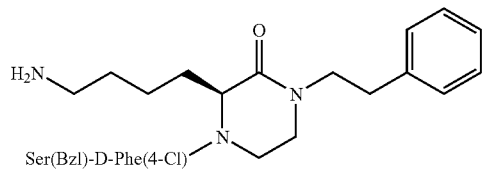

Ser(Bzl)-D-Phe(4-Cl)

was synthesized by the general method of scheme 2 as set forth in Example 6. The molecular weight was determined to be 634.5 ESI-MS (M+1) by the method of Example 2. ($^1$H NMR, CD$_3$OD) δ: 1.2 (m, 2H), 1.55-1.75 (m, 4H), 2.75-3.25 (m, 8H), 3.5 (m, 1H), 3.65 (m, 1H), 3.55-4.15 (m, 5H), 4.55 (m 2H), 4.75 (m, 1H), 5.15 (m, 1H), 7.15-7.45 (m, 14H). Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 46% | 39% | 40% | 14% |

EXAMPLE 13

A compound of the following structure:

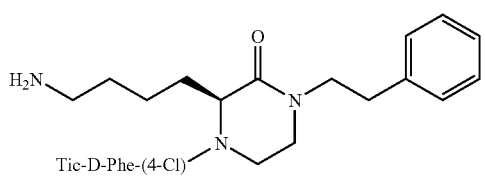

was synthesized by the general method of scheme 2 as set forth in Example 6. The molecular weight was determined to be 616.3 ESI-MS (M+1) by the method of Example 2. ($^1$H NMR, CD$_3$OD) δ: 1.2 (m, 2H), 1.55-1.85 (m, 4H), 2.8-3.25 (m, 10H), 3.55-4.25 (m, 5H), 4.4 (m, 2H), 4.8 (m, 1H), 5.2 (m, 1H), 7.15-7.45 (m, 13H). Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 68% | 21% | 66% | 16% |

EXAMPLE 14

A compound of the following structure:

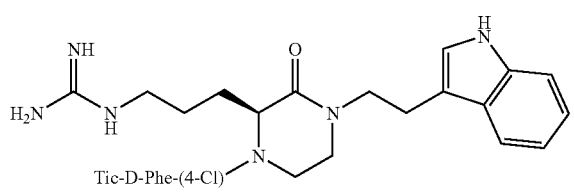

was synthesized by the general method of scheme 2 as set forth in Example 6. The molecular weight was determined to be 683.6 ESI-MS (M+1) by the method of Example 2. ($^1$H NMR, d$_6$-DMSO) δ: 1.4 (m, 2H), 1.65 (m, 1H), 1.85 (m, 1H), 2.8-3.5 (m, 10H), 3.7 (m, 2H), 4.05-4.4 (m, 5H), 4.75 (m, 1H), 5.15 (m, 1H), 7.15-7.45 (m, 13H). Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 96% | 88% | 99% | 89% |

The Ki was determined by the method of Example 4, with the following results:

| Ki (nM) | | | |
|---|---|---|---|
| MC1-R | MC3-R | MC4-R | MC5-R |
| 3 | 77 | 2 | 52 |

EXAMPLE 15

A compound of the following structure:

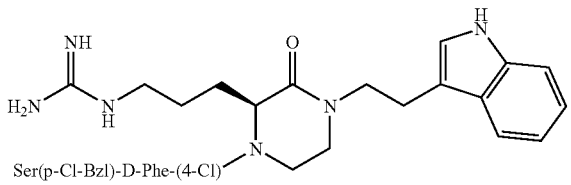

was synthesized by the general method of scheme 2 as set forth in Example 6. The molecular weight was determined to be 735.6 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 81% | 64% | 94% | 90% |

EXAMPLE 16

A compound of the following structure:

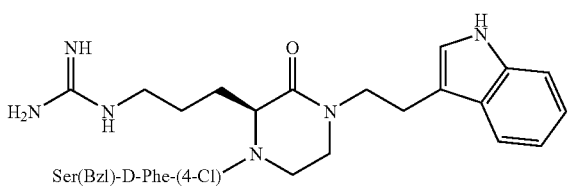

was synthesized by the general method of scheme 2 as set forth in Example 6. The molecular weight was determined to be 701.8 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 86% | 55% | 96% | 81% |

EXAMPLE 17

A compound of the following structure:

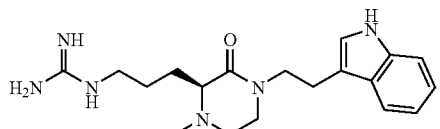

7'amino-heptanoyl-Ser(Bzl)-D-Phe(4-Cl)

was synthesized by the general method of scheme 2 as set forth in Example 6. The molecular weight was determined to be 829.0 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 96% | 97% | 99% | 94% |

The Ki was determined by the method of Example 4, with the following results:

| Ki (nM) | | | |
|---|---|---|---|
| MC1-R | MC3-R | MC4-R | MC5-R |
| 4 | 17 | 2 | 32 |

EXAMPLE 18

A compound of the following structure:

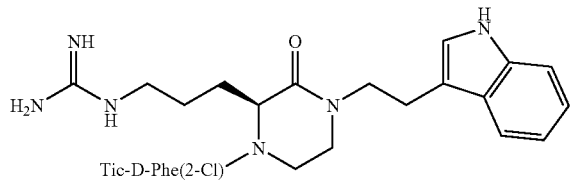

Tic-D-Phe(2-Cl)

was synthesized by the general method of scheme 2 as set forth in Example 6. The molecular weight was determined to be 684.1 ESI-MS (M+1) by the method of Example 2. ($^1$H NMR, CD$_3$OD) δ: 1.4-1.9 (m, 4H), 2.7-3.3 (m, 10H), 3.45 (m, 1H), 3.55 (m, 1H), 3.8-4.2 (m, 3H), 4.4 (m, 2H), 4.8-5.45 (m, 2H), 6.9-7.6 (m, 13H). Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 95% | 50% | 99% | 62% |

EXAMPLE 19

A compound of the following structure:

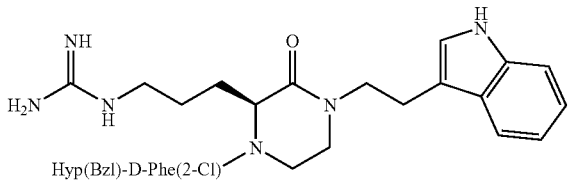

Hyp(Bzl)-D-Phe(2-Cl)

was synthesized by the general method of scheme 2 as set forth in Example 6. The molecular weight was determined to be 728.3 ESI-MS (M+1) by the method of Example 2. ($^1$H NMR, CD$_3$OD) δ: 1.4-1.9 (m, 4H), 2.6 (m, 2H), 2.95-3.25 (m, 10H), 3.4-3.55 (m, 4H), 3.7-4.2 (m, 2H), 4.3-4.45 (m, 2H), 4.55 (m, 2H), 4.8-5.45 (m, 2H), 6.9-7.6 (m, 14H). Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 91% | 59% | 99% | 85% |

EXAMPLE 20

A compound of the following structure:

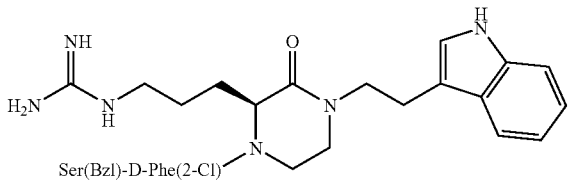

Ser(Bzl)-D-Phe(2-Cl)

was synthesized by the general method of scheme 2 as set forth in Example 6. The molecular weight was determined to be 702.2 ESI-MS (M+1) by the method of Example 2. ($^1$H NMR, CD$_3$OD) δ: 1.4-1.9 (m, 4H), 2.85-3.25 (m, 8H), 3.35-3.7 (m, 4H), 3.75-4.15 (m, 3H), 4.5 (m, 2H), 4.8-5.35 (m, 2H), 6.9-7.6 (m, 14H). Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 87% | 40% | 98% | 71% |

EXAMPLE 21

A compound of the following structure:

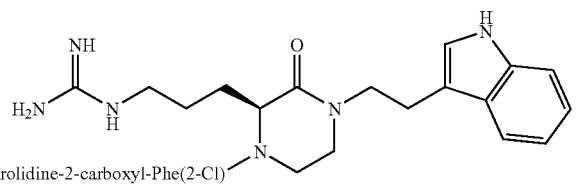

(2S,5R)-5-Phenylpyrrolidine-2-carboxyl-Phe(2-Cl)

was synthesized by the general method of scheme 2 as set forth in Example 6. The molecular weight was determined to be 698.1 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 62% | 22% | 83% | 19% |

EXAMPLE 22

A compound of the following structure:

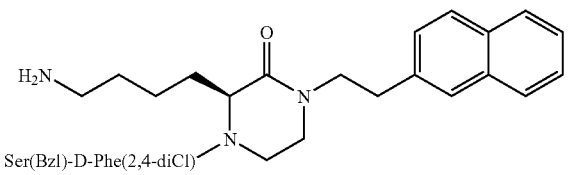

Ser(Bzl)-D-Phe(2,4-diCl)

was synthesized by the general method of scheme 3 as set forth in Example 6. The molecular weight was determined to be 718.5 ESI-MS (M+1) by the method of Example 2. ($^1$H NMR, CD$_3$OD) δ: 1.0-1.9 (m, 6H), 2.5-3.3 (m, 8H), 3.53-3.8 (m, 4H), 4.1 (m, 3H), 4.5 (m, 2H), 4.7-5.3 (m, 2H), 7.0-7.9 (m, 15H). Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 40% | 47% | 98% | 76% |

In a cAMP assay as in Example 4 for determination of agonist/antagonist status, it was determined that the compound was an agonist as to MC1-R, MC4-R and MC5-R.

EXAMPLE 23

A compound of the following structure:

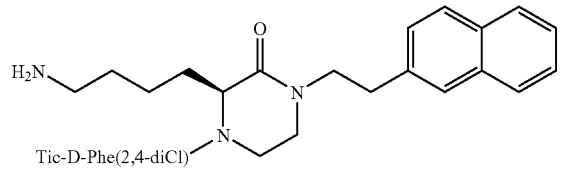

Tic-D-Phe(2,4-diCl)

was synthesized by the general method of scheme 3 as set forth in Example 6. The molecular weight was determined to be 700.3 ESI-MS (M+1) by the method of Example 2. ($^1$H NMR, CD$_3$OD) δ: 1.0-1.9 (m, 6H), 2.6-3.3 (m, 10H), 3.4-4.7 (m, 5H), 4.4 (m, 2H), 4.7-5.4 (m, 2H), 7.0-7.9 (m, 14H). Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 63% | 62% | 100% | 80% |

In a cAMP assay as in Example 4 for determination of agonist/antagonist status, it was determined that the compound was an agonist as to MC1-R, MC4-R and MC5-R.

EXAMPLE 24

A compound of the following structure:

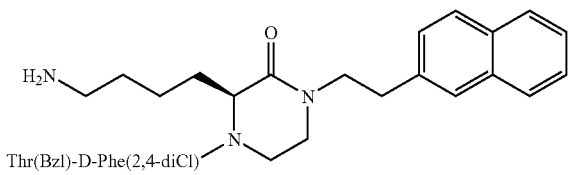

Thr(Bzl)-D-Phe(2,4-diCl)

was synthesized by the general method of scheme 3 as set forth in Example 6. The molecular weight was determined to be 732.4 ESI-MS (M+1) by the method of Example 2. ($^1$H NMR, CD$_3$OD) δ: 1.0-1.9 (m, 9H), 2.5-3.25 (m, 8H), 3.4-3.9 (m, 4H), 4.05 (m, 1H), 4.15 (m, 1H) 4.25 (m, 1H), 4.5 (m, 1H), 4.7-5.3 (m, 2H), 7.0-7.9 (m, 15H). Competitive inhibition testing of the compound following the methods of Example 3 yielded the following results (average of triplicates with actual mean values described; experimental results less than 0% reported as 0%):

| Inhibition at 1 µM | | | |
|---|---|---|---|
| MC1-R | MC3-R | MC4-R | MC5-R |
| 30% | 34% | 99% | 78% |

In a cAMP assay as in Example 4 for determination of agonist/antagonist status, it was determined that the compound was an agonist as to MC1-R, MC4-R and MC5-R.

EXAMPLE 25

A compound of the following structure:

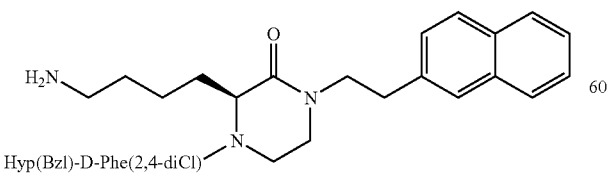

Hyp(Bzl)-D-Phe(2,4-diCl)

was synthesized by the general method of scheme 3 as set forth in Example 6. The molecular weight was determined to be 744.5 ESI-MS (M+1) by the method of Example 2. ($^1$H NMR, CD$_3$OD) δ: 1.0-1.9 (m, 6H), 2.55-3.3 (m, 10H), 3.4-4.15 (m, 7H), 4.4 (m, 2H), 4.6 (m, 2H), 4.7-5.4 (m, 2H), 7.1-7.9 (m, 15H). Competitive inhibition testing of the compound following the methods of Example 3 yielded the following results (average of triplicates with actual mean values described; experimental results less than 0% reported as 0%):

| Inhibition at 1 µM | | | |
|---|---|---|---|
| MC1-R | MC3-R | MC4-R | MC5-R |
| 21% | 61% | 100% | 83% |

In a cAMP assay as in Example 4 for determination of agonist/antagonist status, it was determined that the compound was an agonist as to MC1-R, MC4-R and MC5-R.

EXAMPLE 26

A compound of the following structure:

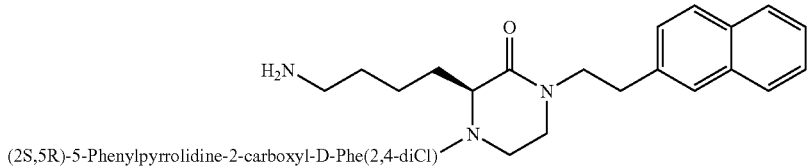

(2S,5R)-5-Phenylpyrrolidine-2-carboxyl-D-Phe(2,4-diCl)

was synthesized by the general method of scheme 3 as set forth in Example 6. The molecular weight was determined to be 714.5 ESI-MS (M+1) by the method of Example 2. ($^1$H NMR, CD$_3$OD) δ: 1.0-1.9 (m, 6H), 2.1-3.25 (m, 10H), 3.4-4.15 (m, 4H), 4.4 (m, 1H), 4.65 (m, 1H), 4.7-5.3 (m, 2H), 7.1-7.9 (m, 15H). Competitive inhibition testing of the compound following the methods of Example 3 yielded the following results (average of triplicates with actual mean values described; experimental results less than 0% reported as 0%):

| Inhibition at 1 µM | | | |
|---|---|---|---|
| MC1-R | MC3-R | MC4-R | MC5-R |
| 0% | 18% | 92% | 51% |

In a cAMP assay as in Example 4 for determination of agonist/antagonist status, it was determined that the compound was an agonist as to MC1-R, MC4-R and MC5-R. The Ki was determined by the method of Example 4, with the following results:

| Ki (nM) | | | |
|---|---|---|---|
| MC1-R | MC3-R | MC4-R | MC5-R |
| >1 µM | >1 µM | 50 | 789 |

EXAMPLE 27

A compound of the following structure:

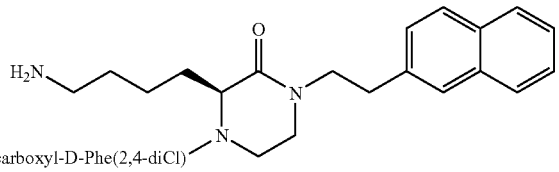

(2R,5S)-5-Phenylpyrrolidine-2-carboxyl-D-Phe(2,4-diCl)

was synthesized by the general method of scheme 3 as set forth in Example 6. The molecular weight was determined to be 714.5 ESI-MS (M+1) by the method of Example 2. ($^1$H NMR, $CD_3OD$) δ: 1.0-1.9 (m, 6H), 2.1-3.3 (m, 10H), 3.45-4.1 (m, 4H), 4.45 (m, 1H), 4.7 (m, 1H), 4.75-5.3 (m, 2H), 7.1-7.9 (m, 15H). Competitive inhibition testing of the compound following the methods of Example 3 yielded the following results (average of triplicates with actual mean values described; experimental results less than 0% reported as 0%):

| Inhibition at 1 µM | | | |
|---|---|---|---|
| MC1-R | MC3-R | MC4-R | MC5-R |
| 0% | 9% | 71% | 46% |

In a cAMP assay as in Example 4 for determination of agonist/antagonist status, it was determined that the compound was an agonist as to MC1-R MC4-R and MC5-R.

EXAMPLE 28

A compound of the following structure:

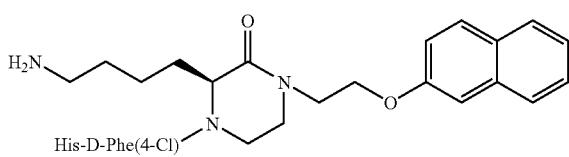

His-D-Phe(4-Cl)

was synthesized by the general method of scheme 4 as set forth in Example 6. The molecular weight was determined to be 660.6 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 µM | | | |
|---|---|---|---|
| MC1-R | MC3-R | MC4-R | MC5-R |
| 97% | 26% | 56% | 21% |

EXAMPLE 29

A compound of the following structure:

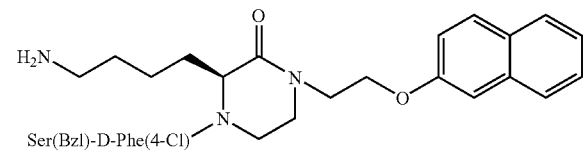

Ser(Bzl)-D-Phe(4-Cl)

was synthesized by the general method of scheme 4 as set forth in Example 6. The molecular weight was determined to be 700.4 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 µM | | | |
|---|---|---|---|
| MC1-R | MC3-R | MC4-R | MC5-R |
| 64% | 21% | 64% | 72% |

EXAMPLE 30

A compound of the following structure:

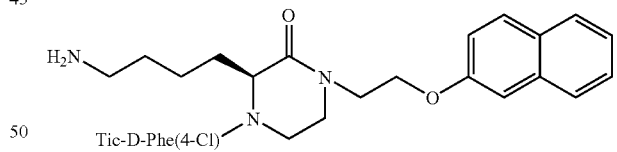

Tic-D-Phe(4-Cl)

was synthesized by the general method of scheme 4 as set forth in Example 6. The molecular weight was determined to be 682.5 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 µM | | | |
|---|---|---|---|
| MC1-R | MC3-R | MC4-R | MC5-R |
| 88% | 35% | 88% | 65% |

EXAMPLE 31

A compound of the following structure:

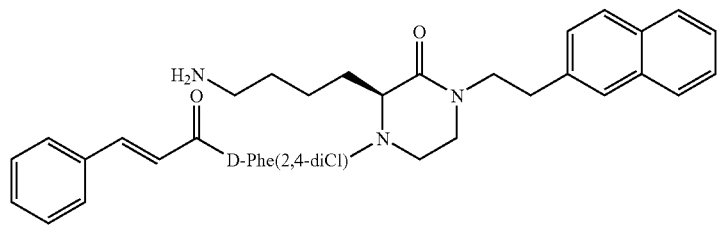

was synthesized by the general method of scheme 3 as set forth in Example 6. The molecular weight was determined to be 671.2 ESI-MS (M+1) by the method of Example 2. ($^1$H NMR, CD$_3$OD) δ: 1.0-1.9 (m, 6H), 2.7-3.25 (m, 8H), 3.45-4.15 (m, 4H), 4.35-5.3 (m, 2H), 6.55-6.75 (m, 2H), 7.1-7.9 (m, 15H). Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 30% | 46% | 96% | 60% |

In a cAMP assay as in Example 4 for determination of agonist/antagonist status, it was determined that the compound was an antagonist as to MC1-R and MC4-R and an agonist as to MC5-R. The Ki was determined by the method of Example 4, with the following results:

| Ki (nM) | | | |
|---|---|---|---|
| MC1-R | MC3-R | MC4-R | MC5-R |
| >1 μM | >1 μM | 13 | 410 |

EXAMPLE 32

A compound of the following structure:

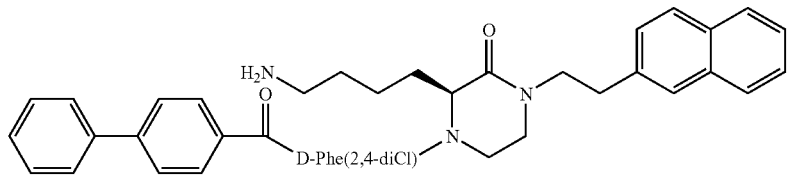

was synthesized by the general method of scheme 3 as set forth in Example 6. The molecular weight was determined to be 735.3 ESI-MS (M+1) by the method of Example 2. ($^1$H NMR, CD$_3$OD) δ: 1.0-1.9 (m, 6H), 2.6-3.25 (m, 8H), 3.4-4.15 (m, 4H), 4.35-5.3 (m, 2H), 7.1-7.9 (m, 19H). Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 0% | 4% | 72% | 54% |

EXAMPLE 33

A compound of the following structure:

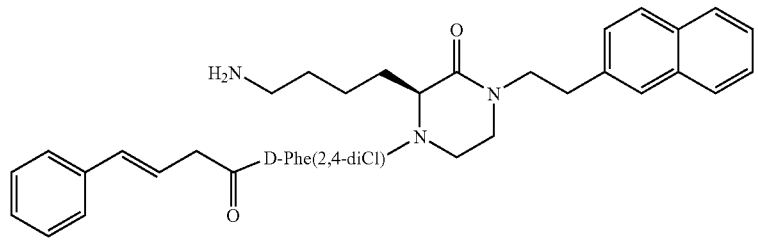

was synthesized by the general method of scheme 3 as set forth in Example 6. The molecular weight was determined to be 685.2 ESI-MS (M+1) by the method of Example 2. ($^1$H NMR, CD$_3$OD) δ: 1.0-1.9 (m, 6H), 2.6-3.25 (m, 10H), 3.4-4.1 (m, 4H), 4.35-5.3 (m, 2H), 6.15 (m, 1H), 6.45 (m, 1H), 7.1-7.9 (m, 15H). Competitive inhibition testing of the compound following the methods of Example 3 yielded the following results (average of triplicates with actual mean values described; experimental results less than 0% reported as 0%):

| Inhibition at 1 µM | | | |
|---|---|---|---|
| MC1-R | MC3-R | MC4-R | MC5-R |
| 14% | 25% | 91% | 61% |

In a cAMP assay as in Example 4 for determination of agonist/antagonist status, it was determined that the compound was an antagonist as to MC1-R and MC4-R and an agonist as to MC5-R.

EXAMPLE 34

A compound of the following structure:

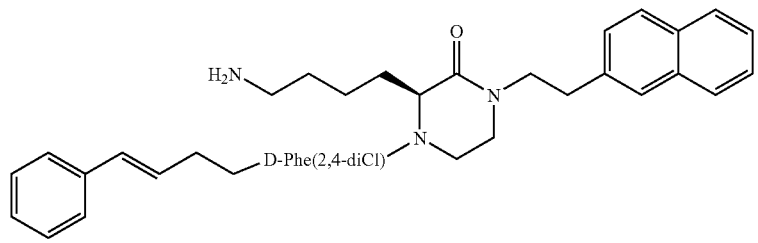

was synthesized by the general method of scheme 3 as set forth in Example 6. The molecular weight was determined to be 657.1 ESI-MS (M+1) by the method of Example 2. ($^1$H NMR, CD$_3$OD) δ: 0.85-1.7 (m, 6H), 2.6-3.3 (m, 10H), 3.4-4.1 (m, 4H), 4.4-4.8 (m, 2H), 6.15 (m, 1H), 6.8 (m, 1H), 7.2-7.9 (m, 15H). Competitive inhibition testing of the compound following the methods of Example 3 yielded the following results (average of triplicates with actual mean values described; experimental results less than 0% reported as 0%):

| Inhibition at 1 µM | | | |
|---|---|---|---|
| MC1-R | MC3-R | MC4-R | MC5-R |
| 7% | 34% | 92% | 30% |

In a cAMP assay as in Example 4 for determination of agonist/antagonist status, it was determined that the compound was an agonist as to MC1-R, MC4-R and MC5-R.

EXAMPLE 35

A compound of the following structure:

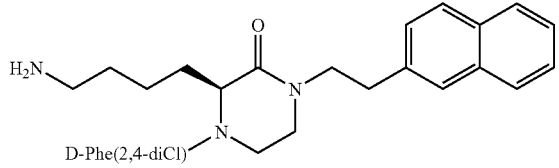

was synthesized by the general method of scheme 3 as set forth in Example 6. The molecular weight was determined to be 541.4 ESI-MS (M+1) by the method of Example 2. ($^1$H NMR, CD$_3$OD) δ: 1.0-1.8 (m, 6H), 2.6-3.3 (m, 8H), 3.4-4.1 (m, 4H), 4.4-4.7 (m, 2H), 7.1-8.0 (m, 10H). Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 9% | 3% | 62% | 4% |

EXAMPLE 36

A compound of the following structure:

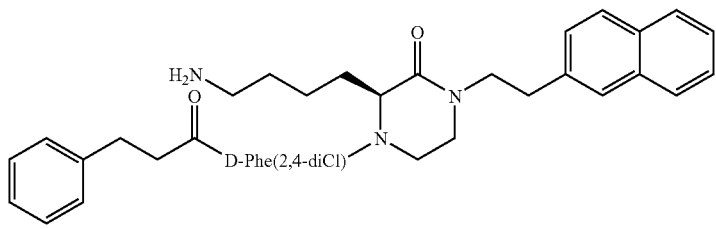

was synthesized by the general method of scheme 3 as set forth in Example 6. The molecular weight was determined to be 673.2 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 72% | 22% | 92% | 34% |

In a cAMP assay as in Example 4 for determination of agonist/antagonist status, it was determined that the compound was an agonist as to MC1-R and MC5-R and antagonist as to MC4-R.

EXAMPLE 37

A compound of the following structure:

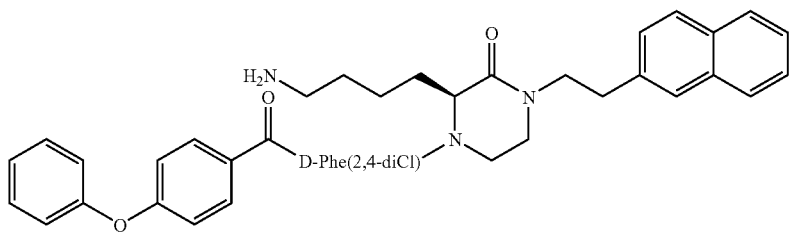

was synthesized by the general method of scheme 3 as set forth in Example 6. The molecular weight was determined to be 737.2 ESI-MS (M+1) by the method of Example 2. ($^1$H NMR, $CD_3OD$) δ: 1.0-2.0 (m, 6H), 2.7-3.3 (m, 8H), 3.4-4.15 (m, 4H), 4.4-5.3 (m, 2H), 7.0-8.0 (m, 19H). Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 35% | 51% | 99% | 51% |

In a cAMP assay as in Example 4 for determination of agonist/antagonist status, it was determined that the compound was an antagonist as to MC1-R and MC4-R and an agonist as to MC5-R.

EXAMPLE 38

A compound of the following structure:

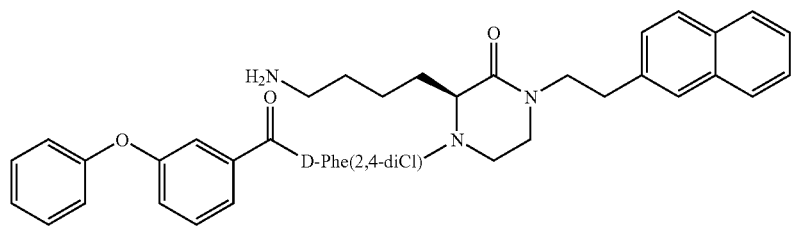

was synthesized by the general method of scheme 3 as set forth in Example 6. The molecular weight was determined to be 737.2 ESI-MS (M+1) by the method of Example 2. ($^1$H NMR, CD$_3$OD) δ: 1.0-2.0 (m, 6H), 2.7-3.3 (m, 8H), 3.4-4.15 (m, 4H), 4.4-5.3 (m, 2H), 7.0-8.0 (m, 19H). Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 3% | 21% | 97% | 61% |

In a cAMP assay as in Example 4 for determination of agonist/antagonist status, it was determined that the compound was an antagonist as to MC1-R and MC4-R and an agonist as to MC5-R.

EXAMPLE 39

A compound of the following structure:

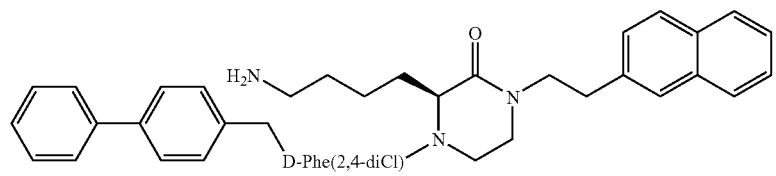

was synthesized by the general method of scheme 3 as set forth in Example 6. The molecular weight was determined to be 707.1 ESI-MS (M+1) by the method of Example 2. ($^1$H NMR, CD$_3$OD) δ: 0.9-1.7 (m, 6H), 2.6-3.3 (m, 8H), 3.4-4.1 (m, 4H), 4.4-5.1 (m, 4H), 7.2-7.9 (m, 19H). Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 0% | 4% | 85% | 9% |

In a cAMP assay as in Example 4 for determination of agonist/antagonist status, it was determined that the compound was an antagonist as to MC1-R and MC4-R and an agonist as to MC5-R.

EXAMPLE 40

A compound of the following structure:

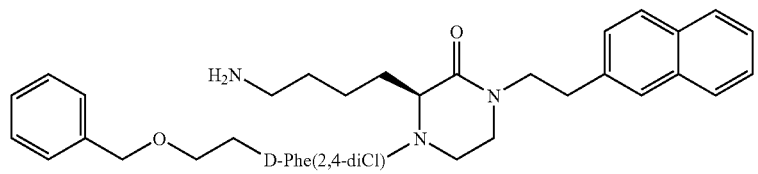

was synthesized by the general method of scheme 3 as set forth in Example 6. The molecular weight was determined to be 675.3 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 27% | 17% | 91% | 30% |

In a cAMP assay as in Example 4 for determination of agonist/antagonist status, it was determined that the compound was an antagonist as to MC1-R and MC4-R and an agonist as to MC5-R.

EXAMPLE 41

A compound of the following structure:

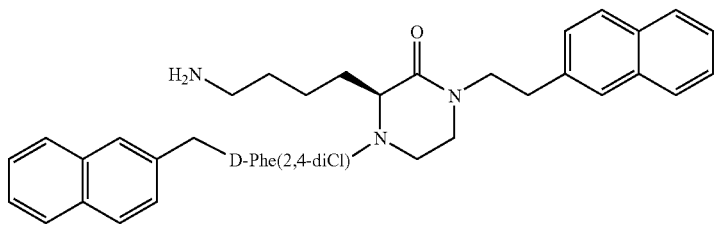

was synthesized by the general method of scheme 3 as set forth in Example 6. The molecular weight was determined to be 681.2 ESI-MS (M+1) by the method of Example 2. ($^1$H NMR, CD$_3$OD) δ: 0.9-1.7 (m, 6H), 2.6-3.3 (m, 8H), 3.4-4.1 (m, 4H), 4.4-5.1 (m, 4H), 7.2-8.0 (m, 19H). Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 4% | 4% | 84% | 2% |

In a cAMP assay as in Example 4 for determination of agonist/antagonist status, it was determined that the compound was an antagonist as to MC1-R and MC4-R and an agonist as to MC5-R.

EXAMPLE 42

A compound of the following structure:

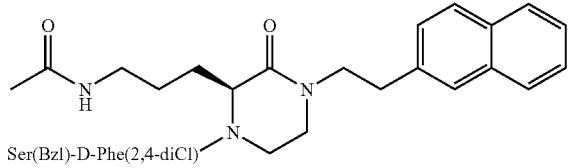

was synthesized by the general method of scheme 3 as set forth in Example 6. The molecular weight was determined to be 746.4 ESI-MS (M+1) by the method of Example 2. ($^1$H NMR, CD$_3$OD) δ: 1.25-1.85 (m, 4H), 1.95 (d, 3H), 2.5-3.25 (m, 8H), 3.3-4.1 (m, 7H), 4.35-5.3 (m, 4H), 7.1-7.9 (m, 15H). Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 13% | 10% | 61% | 30% |

EXAMPLE 43

A compound of the following structure:

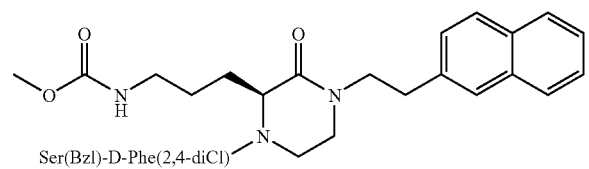

was synthesized by the general method of scheme 3 as set forth in Example 6. The molecular weight was determined to be 762.3 ESI-MS (M+1) by the method of Example 2. ($^1$H NMR, CD$_3$OD) δ: 1.25-1.85 (m, 4H), 2.5-3.25 (m, 8H), 3.3-4.1 (m, 10H), 4.35-5.3 (m, 4H), 7.1-7.9 (m, 15H). Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 1% | 0% | 43% | 20% |

EXAMPLE 44

A compound of the following structure:

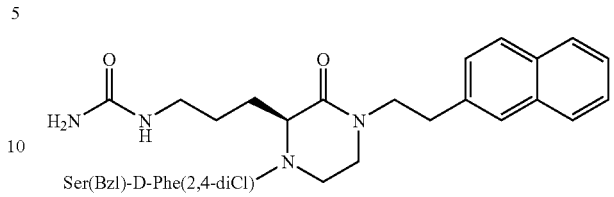

was synthesized by the general method of scheme 3 as set forth in Example 6. The molecular weight was determined to be 747.3 ESI-MS (M+1) by the method of Example 2. ($^1$H NMR, CD$_3$OD) δ: 1.25-1.85 (m, 4H), 2.5-3.25 (m, 8H), 3.3-4.1 (m, 7H), 4.35-5.3 (m, 4H), 7.1-7.9 (m, 15H). Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 8% | 43% | 94% | 66% |

In a cAMP assay as in Example 4 for determination of agonist/antagonist status, it was determined that the compound was an agonist as to MC1-R, MC4-R and MC5-R.

EXAMPLE 45

A compound of the following structure:

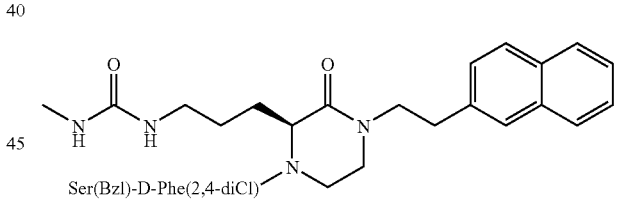

was synthesized by the general method of scheme 3 as set forth in Example 6. The molecular weight was determined to be 761.4 ESI-MS (M+1) by the method of Example 2. ($^1$H NMR, CD$_3$OD) δ: 1.25-1.85 (m, 4H), 2.5-3.25 (m, 11H), 3.3-4.1 (m, 6H), 4.35-5.3 (m, 4H), 7.1-7.9 (m, 15H). Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 5% | 11% | 72% | 31% |

EXAMPLE 46

A compound of the following structure:

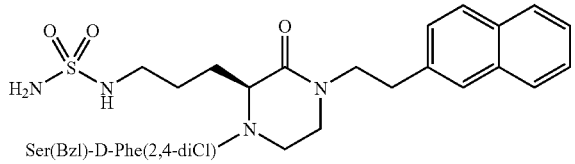

was synthesized by the general method of scheme 3 as set forth in Example 6. The molecular weight was determined to be 783.2 ESI-MS (M+1) by the method of Example 2. ($^1$H NMR, CD$_3$OD) δ: 1.25-1.85 (m, 4H), 2.5-3.25 (m, 8H), 3.3-4.1 (m, 6H), 4.35-5.3 (m, 4H), 7.1-7.9 (m, 15H). Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 0% | 12% | 60% | 25% |

EXAMPLE 47

A compound of the following structure:

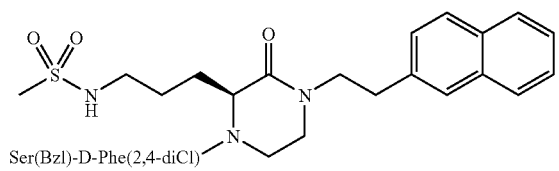

was synthesized by the general method of scheme 3 as set forth in Example 6. The molecular weight was determined to be 782.3 ESI-MS (M+1) by the method of Example 2. ($^1$H NMR, CD$_3$OD) δ: 1.25-1.85 (m, 4H), 2.5-3.25 (m, 8H), 3.3-4.1 (m, 10H), 4.35-5.3 (m, 4H), 7.1-7.9 (m, 15H). Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 0% | 9% | 40% | 14% |

EXAMPLE 48

A compound of the following structure:

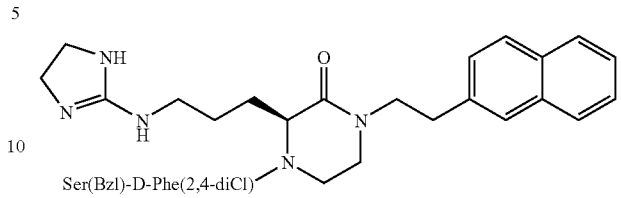

was synthesized by the general method of scheme 3 as set forth in Example 6. The molecular weight was determined to be 772.4 ESI-MS (M+1) by the method of Example 2. ($^1$H NMR, CD$_3$OD) δ: 1.0-1.8 (m, 6H), 2.4-3.3 (m, 12H), 3.4-4.1 (m, 4H), 4.3-5.3 (m, 2H), 7.1-8.0 (m, 15H). Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 63% | 60% | 99% | 75% |

In a cAMP assay as in Example 4 for determination of agonist/antagonist status, it was determined that the compound was an agonist as to MC1-R, MC4-R and MC5-R. The Ki was determined by the method of Example 4, with the following results:

| Ki (nM) | | | |
|---|---|---|---|
| MC1-R | MC3-R | MC4-R | MC5-R |
| >1 μM | >1 μM | 4 | 104 |

EXAMPLE 49

A compound of the following structure:

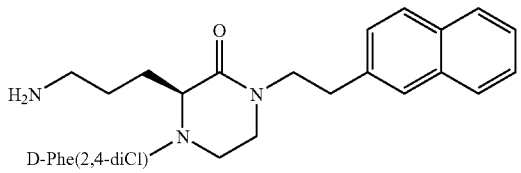

was synthesized by the general method of scheme 3 as set forth in Example 6. The molecular weight was determined to be 527.2 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 2% | 0% | 43% | 1% |

EXAMPLE 50

A compound of the following structure:

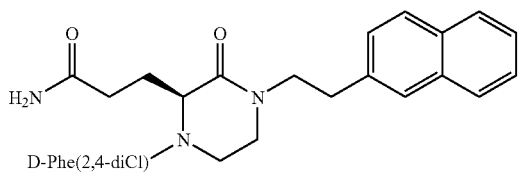

D-Phe(2,4-diCl)

was synthesized by the general method of scheme 3 as set forth in Example 6. The molecular weight was determined to be 541.2 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 0% | 0% | 0% | 0% |

EXAMPLE 51

A compound of the following structure:

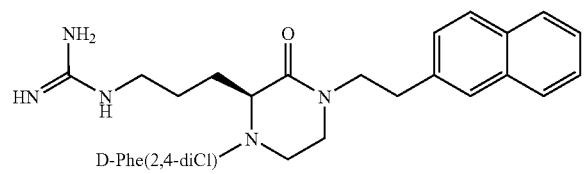

was synthesized by the general method of scheme 3 as set forth in Example 6. The molecular weight was determined to be 568.9 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 22% | 47% | 95% | 35% |

In a cAMP assay as in Example 4 for determination of agonist/antagonist status, it was determined that the compound was an antagonist as to MC1-R and an agonist as to MC4-R and MC5-R.

EXAMPLE 52

A compound of the following structure:

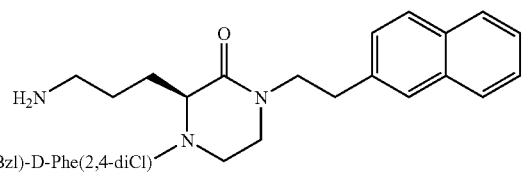

was synthesized by the general method of scheme 3 as set forth in Example 6. The molecular weight was determined to be 704.1 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 36% | 25% | 94% | 63% |

In a cAMP assay as in Example 4 for determination of agonist/antagonist status, it was determined that the compound was an agonist as to MC1-R, MC4-R and MC5-R.

EXAMPLE 53

A compound of the following structure:

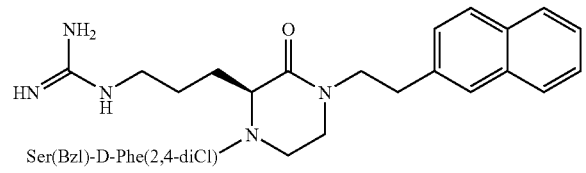

was synthesized by the general method of scheme 3 as set forth in Example 6. The molecular weight was determined to be 746.1 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 81% | 93% | 99% | 96% |

In a cAMP assay as in Example 4 for determination of agonist/antagonist status, it was determined that the compound was an agonist as to MC1-R, MC4-R and MC5-R.

EXAMPLE 54

A compound of the following structure:

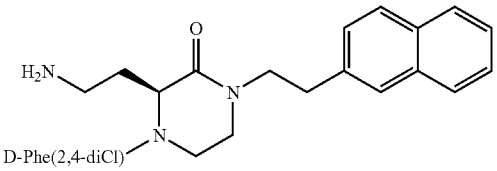

was synthesized by the general method of scheme 3 as set forth in Example 6. The molecular weight was determined to be 512.8 ESI-MS (M+1) by the method of Example 2. ($^1$H NMR, CD$_3$OD) δ: 1.9 (m, 2H), 2.9-3.3 (m, 8H), 3.5-4.0 (m, 4H), 4.4-5.0 (m, 2H), 7.2-7.9 (m, 10H), Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 28% | 11% | 55% | 23% |

EXAMPLE 55

A compound of the following structure:

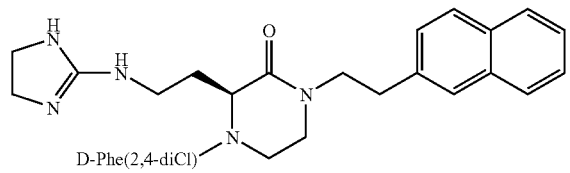

was synthesized by the general method of scheme 3 as set forth in Example 6. The molecular weight was determined to be 580.9 ESI-MS (M+1) by the method of Example 2. ($^1$H NMR, CD$_3$OD) δ: 1.75 (m, 2H), 2.9-3.3 (m, 8H), 3.4-4.1 (m, 8H), 4.4-5.0 (m, 2H), 7.2-7.9 (m, 10H), Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 24% | 14% | 68% | 27% |

EXAMPLE 56

A compound of the following structure:

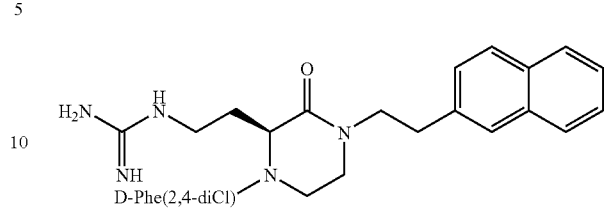

was synthesized by the general method of scheme 3 as set forth in Example 6. The molecular weight was determined to be 554.7 ESI-MS (M+1) by the method of Example 2. ($^1$H NMR, CD$_3$OD) δ: 1.9 (m, 2H), 2.9-3.3 (m, 8H), 3.4-4.1 (m, 4H), 4.3-5.0 (m, 2H), 7.2-7.9 (m, 10H), Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 21% | 13% | 81% | 24% |

EXAMPLE 57

A compound of the following structure:

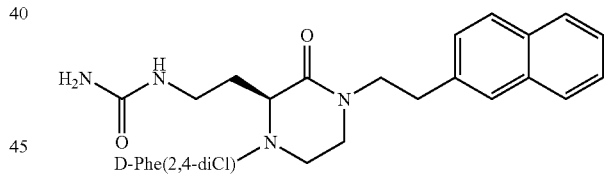

was synthesized by the general method of scheme 3 as set forth in Example 6. The molecular weight was determined to be 555.8 ESI-MS (M+1) by the method of Example 2. ($^1$H NMR, CD$_3$OD) δ: 1.8 (m, 2H), 2.9-3.3 (m, 8H), 3.4-4.05 (m, 4H), 4.4-5.0 (m, 2H), 7.1-7.9 (m, 10H), Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 11% | 0% | 9% | 5% |

EXAMPLE 58

A compound of the following structure:

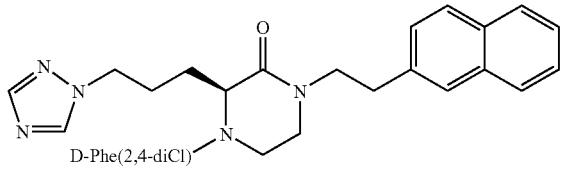

was synthesized by the general method of scheme 3 as set forth in Example 6. The molecular weight was determined to be 579.2 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 µM | | | |
|---|---|---|---|
| MC1-R | MC3-R | MC4-R | MC5-R |
| 7% | 0% | 0% | 3% |

EXAMPLE 59

A compound of the following structure:

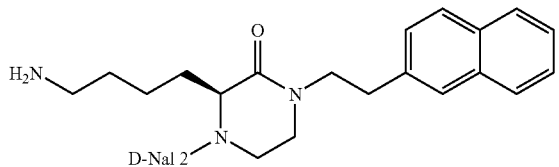

was synthesized by the general method of scheme 3 as set forth in Example 6. The molecular weight was determined to be 523.2 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 µM | | | |
|---|---|---|---|
| MC1-R | MC3-R | MC4-R | MC5-R |
| 26% | 14% | 72% | 30% |

EXAMPLE 60

A compound of the following structure:

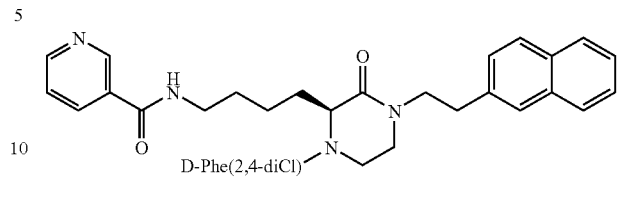

was synthesized by the general method of scheme 3 as set forth in Example 6. The molecular weight was determined to be 645.9 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 µM | | | |
|---|---|---|---|
| MC1-R | MC3-R | MC4-R | MC5-R |
| 4% | 6% | 23% | 13% |

EXAMPLE 61

A compound of the following structure:

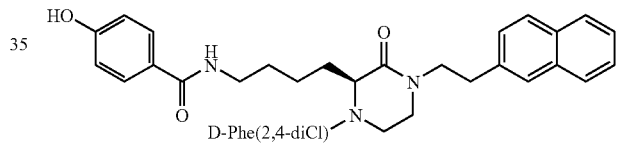

was synthesized by the general method of scheme 3 as set forth in Example 6. The molecular weight was determined to be 660.8 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 µM | | | |
|---|---|---|---|
| MC1-R | MC3-R | MC4-R | MC5-R |
| 3% | 6% | 12% | 26% |

EXAMPLE 62

A compound of the following structure:

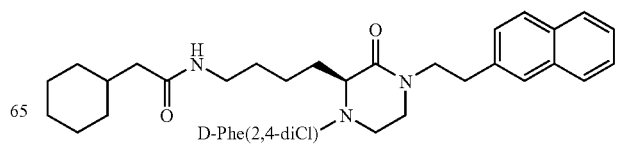

was synthesized by the general method of scheme 3 as set forth in Example 6. The molecular weight was determined to be 664.9 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 0% | 4% | 6% | 2% |

EXAMPLE 63

A compound of the following structure:

D-Phe(2,4-diCl)

was synthesized by the general method of scheme 3 as set forth in Example 6. The molecular weight was determined to be 664.9 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 3% | 6% | 14% | 6% |

EXAMPLE 64

A compound of the following structure:

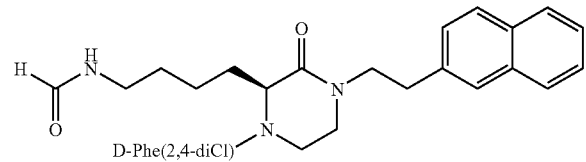

D-Phe(2,4-diCl)

was synthesized by the general method of scheme 3 as set forth in Example 6. The molecular weight was determined to be 568.9 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 8% | 0% | 30% | 6% |

EXAMPLE 65

A compound of the following structure:

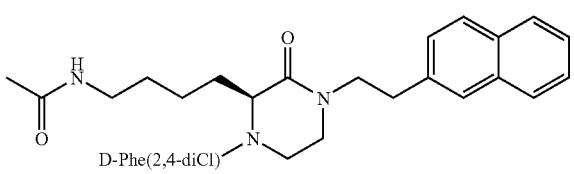

D-Phe(2,4-diCl)

was synthesized by the general method of scheme 3 as set forth in Example 6. The molecular weight was determined to be 582.9 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 17% | 3% | 26% | 0% |

EXAMPLE 66

A compound of the following structure:

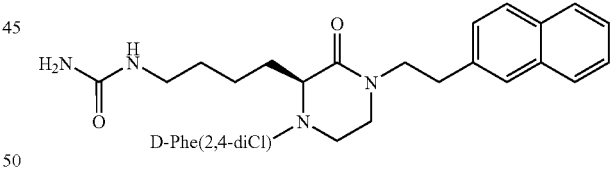

D-Phe(2,4-diCl)

was synthesized by the general method of scheme 3 as set forth in Example 6. The molecular weight was determined to be 583.9 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 43% | 15% | 49% | 14% |

EXAMPLE 67

A compound of the following structure:

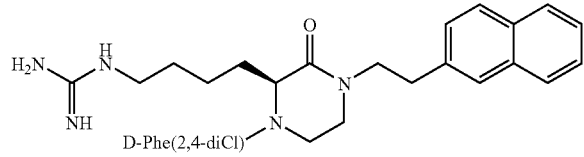

was synthesized by the general method of scheme 3 as set forth in Example 6. The molecular weight was determined to be 582.9 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 µM | | | |
|---|---|---|---|
| MC1-R | MC3-R | MC4-R | MC5-R |
| 66% | 68% | 96% | 42% |

EXAMPLE 68

A compound of the following structure:

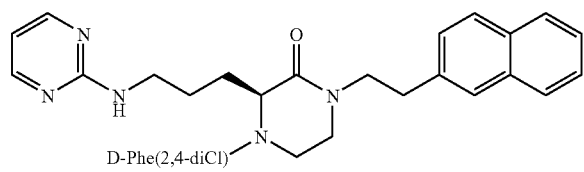

was synthesized by the general method of scheme 3 as set forth in Example 6. The molecular weight was determined to be 605.8 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 µM | | | |
|---|---|---|---|
| MC1-R | MC3-R | MC4-R | MC5-R |
| 3% | 9% | 12% | 19% |

EXAMPLE 69

A compound of the following structure:

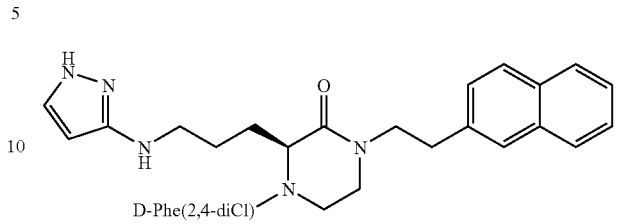

was synthesized by the general method of scheme 3 as set forth in Example 6. The molecular weight was determined to be 593.1 ESI-MS (M+1) by the method of Example 2. ($^1$H NMR, CD$_3$OD) δ: 1.7 (m, 2H), 2.9-3.3 (m, 8H), 3.4-4.1 (m, 4H), 4.4-5.0 (m, 2H), 7.2-7.9 (m, 12H), Competitive inhibition testing of the compound following the methods of Example 3 yielded the following results (average of triplicates with actual mean values described; experimental results less than 0% reported as 0%):

| Inhibition at 1 µM | | | |
|---|---|---|---|
| MC1-R | MC3-R | MC4-R | MC5-R |
| 20% | 8% | 3% | 12% |

EXAMPLE 70

A compound of the following structure:

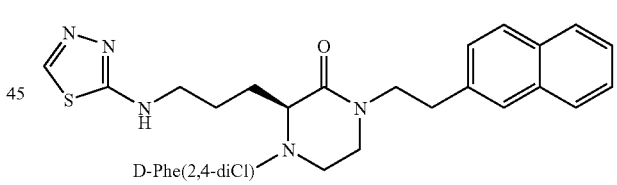

was synthesized by the general method of scheme 3 as set forth in Example 6. The molecular weight was determined to be 611.0 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 µM | | | |
|---|---|---|---|
| MC1-R | MC3-R | MC4-R | MC5-R |
| 28% | 31% | 70% | 32% |

EXAMPLE 71

A compound of the following structure:

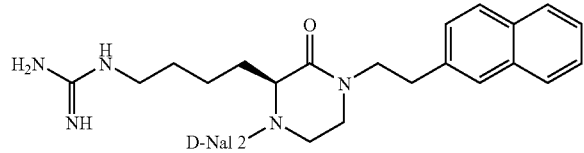

was synthesized by the general method of scheme 3 as set forth in Example 6. The molecular weight was determined to be 565.3 ESI-MS (M+1) by the method of Example 2. Competitive inhibition testing of the compound following the methods of Example 3 yielded the following results (average of triplicates with actual mean values described; experimental results less than 0% reported as 0%):

| | Inhibition at 1 μM | | |
|---|---|---|---|
| MC1-R | MC3-R | MC4-R | MC5-R |
| 60% | 73% | 97% | 57% |

EXAMPLE 72

A compound of the following structure:

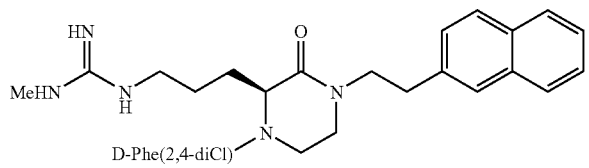

was synthesized by the general method of scheme 3 as set forth in Example 6. The molecular weight was determined to be 582.6 ESI-MS (M+1) by the method of Example 2. ($^1$H NMR, CD$_3$OD) δ: 1.1-1.8 (m, 4H), 2.85 (s, 1H), 2.9-3.3 (m, 8H), 3.35-4.1 (m, 4H), 4.4-5.0 (m, 2H), 7.1-7.9 (m, 10H). Competitive inhibition testing of the compound following the methods of Example 3 yielded the following results (average of triplicates with actual mean values described; experimental results less than 0% reported as 0%):

| | Inhibition at 1 μM | | |
|---|---|---|---|
| MC1-R | MC3-R | MC4-R | MC5-R |
| 19% | 43% | 93% | 27% |

EXAMPLE 73

A compound of the following structure:

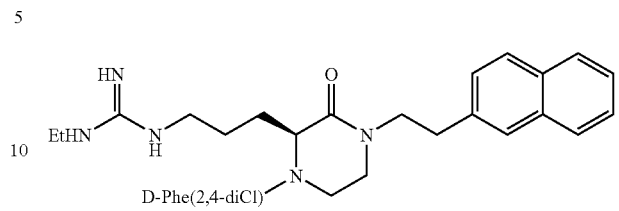

was synthesized by the general method of scheme 3 as set forth in Example 6. The molecular weight was determined to be 596.6 ESI-MS (M+1) by the method of Example 2. Competitive inhibition testing of the compound following the methods of Example 3 yielded the following results (average of triplicates with actual mean values described; experimental results less than 0% reported as 0%):

| | Inhibition at 1 μM | | |
|---|---|---|---|
| MC1-R | MC3-R | MC4-R | MC5-R |
| 14% | 35% | 91% | 24% |

EXAMPLE 74

A compound of the following structure:

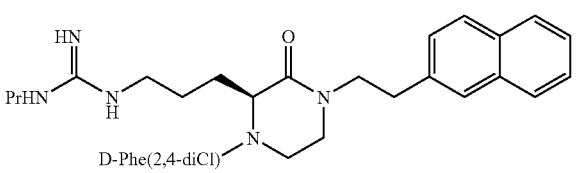

was synthesized by the general method of scheme 3 as set forth in Example 6. The molecular weight was determined to be 610.6 ESI-MS (M+1) by the method of Example 2. Competitive inhibition testing of the compound following the methods of Example 3 yielded the following results (average of triplicates with actual mean values described; experimental results less than 0% reported as 0%):

| | Inhibition at 1 μM | | |
|---|---|---|---|
| MC1-R | MC3-R | MC4-R | MC5-R |
| 13% | 34% | 88% | 26% |

EXAMPLE 75

A compound of the following structure:

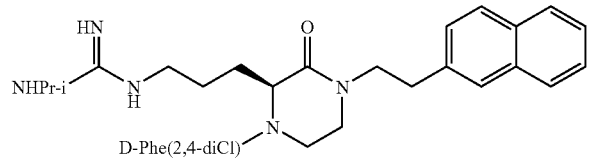

was synthesized by the general method of scheme 3 as set forth in Example 6. The molecular weight was determined to be 610.6 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 37% | 40% | 85% | 28% |

EXAMPLE 76

A compound of the following structure:

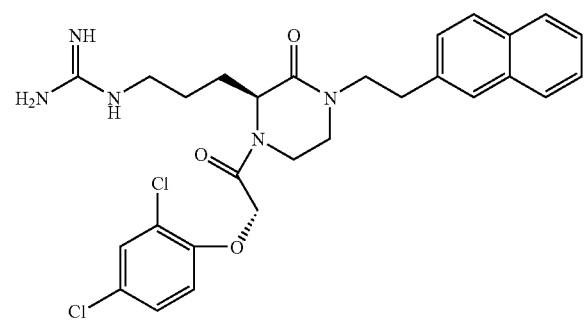

was synthesized by the general method of scheme 3 as set forth in Example 6. The molecular weight was determined to be 569.5 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 38% | 24% | 41% | 21% |

EXAMPLE 77

A compound of the following structure:

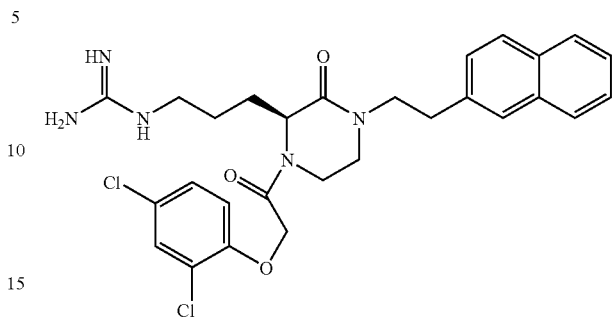

was synthesized by the general method of scheme 3 as set forth in Example 6. The molecular weight was determined to be 555.6 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 15% | 0% | 24% | 20% |

EXAMPLE 78

A compound of the following structure:

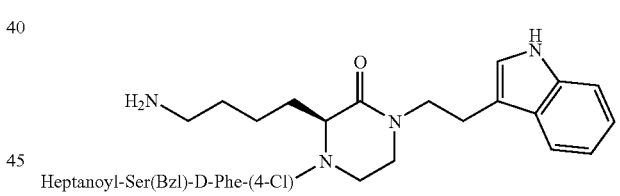

was synthesized by the general method of scheme 2 as set forth in Example 6. The molecular weight was determined to be 785.3 ESI-MS (M+1) by the method of Example 2. ($^1$H NMR, CD$_3$OD) δ: 0.8-1.9 (m, 17H), 2.25 (m, 2H), 2.75-3.25 (m, 8H), 3.35-4.05 (m, 6H), 4.55 (m, 3H), 4.9 (m, 1H), 5.3 (m, 1H), 6.9-7.6 (m, 14H). Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 96% | 72% | 99% | 99% |

EXAMPLE 79

A compound of the following structure:

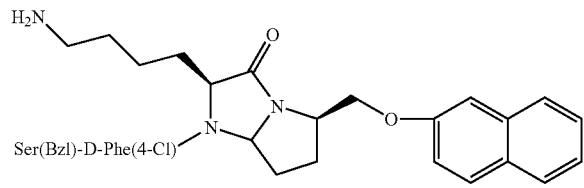

was synthesized by the general method of scheme 6 as set forth in Example 8. The molecular weight was determined to be 712.3 ESI-MS (M+1) by the method of Example 2. ($^1$H NMR, CD$_3$OD) δ: 1.0-1.8 (m, 6H), 2.2 (m, 2H), 2.5 (m, 2H), 2.7 (m, 2H), 3.0 (m, 2H), 3.7 (m, 2H), 4.1 (m, 2H) 4.3-4.5 (m, 3H), 4.6 (m, 2H), 5.1 (m, H), 5.3 (m, H), 7.1-7.9 (m, 16H). Competitive inhibition testing of compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 90% | 14% | 81% | 86% |

EXAMPLE 80

A compound of the following structure:

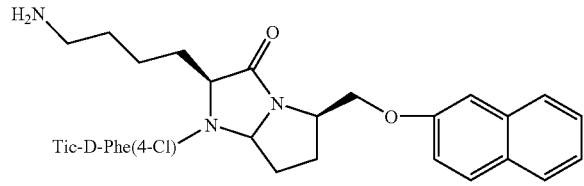

was synthesized by the general method of scheme 6 as set forth in Example 8. The molecular weight was determined to be 694.0 ESI-MS (M+1) bythe method of Example 2. ($^1$H NMR, CD$_3$OD) δ: 1.0-1.8 (m, 6H), 2.2 (m, 2H), 2.5 (m, 2H), 2.7 (m, 2H), 2.9 (m, 2H), 3.2 (m, 2H), 4.2 (m, 2H), 4.2-4.4 (m, 3H), 4.4 (m, 2H), 5.1 (m, H), 5.4 (m, H), 7.1-7.9 (m, 15H). Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 95% | 24% | 94% | 73% |

In a cAMP assay as in Example 4 for determination of agonist/antagonist status, it was determined that the compound was an agonist as to MC4-R. The Ki was determined by the method of Example 4, with the following results:

| Ki (nM) | | | |
|---|---|---|---|
| MC1-R | MC3-R | MC4-R | MC5-R |
| 10 | >1 μM | 24 | 398 |

EXAMPLE 81

A compound of the following structure:

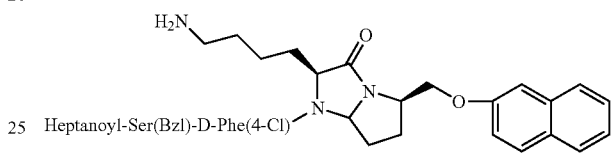

was synthesized by the general method of scheme 6 as set forth in Example 8. The molecular weight was determined to be 824.2 ESI-MS (M+1) bythe method of Example 2. ($^1$H NMR, CD$_3$OD) δ: 0.9 (m, 3H), 1.1-1.8 (m, 14H), 2.1 (m, 2H), 2.2 (m, 2H), 2.5 (m, 2H), 2.7 (m, 2H), 3.0 (m, 2H), 3.7 (m, 2H), 4.2 (m, 2H), 4.3-4.5 (m, 3H), 4.6 (m, 2H), 5.1 (m, H), 5.3 (m, H), 7.1-7.9 (m, 16H). Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 98% | 75% | 98% | 95% |

In a cAMP assay as in Example 4 for determination of agonist/antagonist status, it was determined that the compound was an antagonist as to MC4-R. The Ki was determined by the method of Example 4, with the following results:

| Ki (nM) | | | |
|---|---|---|---|
| MC1-R | MC3-R | MC4-R | MC5-R |
| 13 | 209 | 23 | 134 |

EXAMPLE 82

A compound of the following structure:

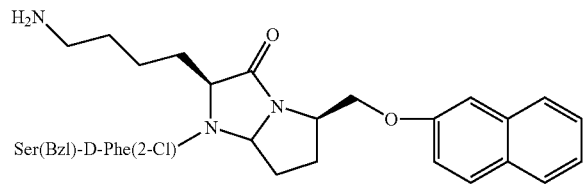

was synthesized by the general method of scheme 6 as set forth in Example 8. The molecular weight was determined to be 711.9 ESI-MS (M+1) by the method of Example 2. ($^1$H NMR, CD$_3$OD) δ: 1.0-1.8 (m, 6H), 2.1 (m, 2H), 2.4 (m, 2H), 2.7 (m, 2H), 3.1 (m, 2H), 3.6 (m, 2H), 4.1 (m, 2H), 4.2-4.4 (m, 3H), 4.5 (m, 2H), 5.1 (m, H), 5.3 (m, H), 7.1-7.9 (m, 16H). Competitive inhibition testing of the compound following the methods of Example 3 yielded the following results (average of triplicates with actual mean values described; experimental results less than 0% reported as 0%):

| Inhibition at 1 µM | | | |
|---|---|---|---|
| MC1-R | MC3-R | MC4-R | MC5-R |
| 28% | 0% | 60% | 38% |

EXAMPLE 83

A compound of the following structure:

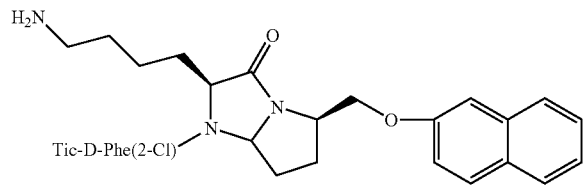

was synthesized by the general method of scheme 6 as set forth in Example 8. The molecular weight was determined to be 694.3 ESI-MS (M+1) by the method of Example 2. ($^1$H NMR, CD$_3$OD) δ: 1.0-1.8 (m, 6H), 2.2 (m, 2H), 2.4 (m, 2H), 2.7 (m, 2H), 2.8 (m, 2H), 3.2 (m, 2H), 4.2 (m, 2H), 4.2-4.4 (m, 3H), 4.4 (m, 2H), 5.2 (m, H), 5.4 (m, H), 7.1-7.9 (m, 15H). Competitive inhibition testing of the compound following the methods of Example 3 yielded the following results (average of triplicates with actual mean values described; experimental results less than 0% reported as 0%):

| Inhibition at 1 µM | | | |
|---|---|---|---|
| MC1-R | MC3-R | MC4-R | MC5-R |
| 42% | 2% | 89% | 38% |

EXAMPLE 84

A compound of the following structure:

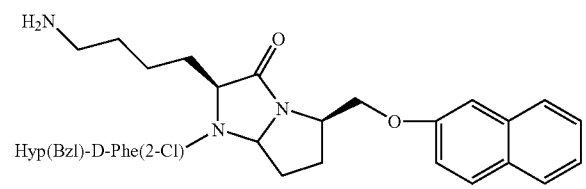

was synthesized by the general method of scheme 6 as set forth in Example 8. The molecular weight was determined to be 738.0 ESI-MS (M+1) by the method of Example 2. ($^1$H NMR, CD$_3$OD) δ: 1.0-2.0 (m, 6H), 2.2 (m, 2H), 2.3-2.9 (m, 6H), 3.2 (m, 2H), 3.4 (m, 2H), 4.2 (m, 2H), 4.2-4.4 (m, 3H), 4.6 (m, 2H), 5.2 (m, H), 5.4 (m, H), 7.1-7.9 (m, 16H). Competitive inhibition testing of the compound following the methods of Example 3 yielded the following results (average of triplicates with actual mean values described; experimental results less than 0% reported as 0%):

| Inhibition at 1 µM | | | |
|---|---|---|---|
| MC1-R | MC3-R | MC4-R | MC5-R |
| 44% | 0% | 74% | 37% |

EXAMPLE 85

A compound of the following structure:

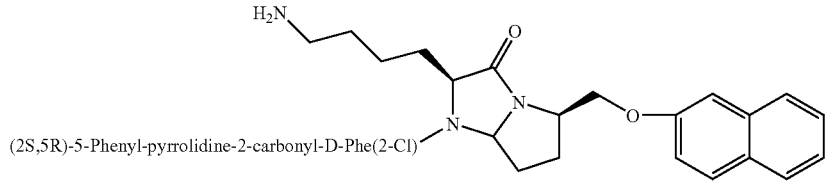

was synthesized by the general method of scheme 6 as set forth in Example 8. The molecular weight was determined to be 707.9 ESI-MS (M+1) by the method of Example 2. ($^1$H NMR, CD$_3$OD) δ: 1.0-1.8 (m, 6H), 2.1 (m, 2H), 2.2-2.9 (m, 10H), 3.2 (m, 2H), 4.2 (m, 2H), 4.2-4.4 (m, 3H), 5.3 (m, H), 5.5 (m, H), 7.1-7.9 (m, 16H). Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 4% | 0% | 44% | 13% |

EXAMPLE 86

A compound of the following structure:

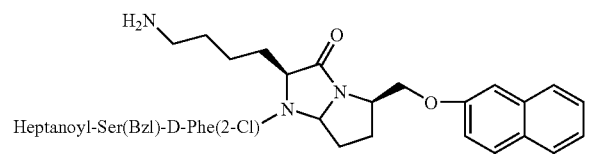

Heptanoyl-Ser(Bzl)-D-Phe(2-Cl)

was synthesized by the general method of scheme 6 as set forth in Example 8. The molecular weight was determined to be 824.0 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 71% | 30% | 82% | 47% |

EXAMPLE 87

A compound of the following structure:

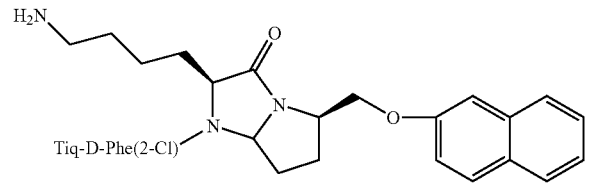

Tiq-D-Phe(2-Cl)

was synthesized by the general method of scheme 6 as set forth in Example 8. The molecular weight was determined to be 694.2 ESI-MS (M+1) by the method of Example 2. ($^1$H NMR, CD$_3$OD) δ: 1.0-1.8 (m, 6H), 2.15 (m, 1H), 2.35 (m, 1H), 2.45 (m, 1H), 2.65-2.9 (m, 3H), 3.1 (m, 3H), 3.4 (m, 3H), 3.65 (m, 1H), 4.2 (m, 1H), 4.3-4.6 (m, 3H), 5.0-5.55 (m, 3H), 6.8-7.9 (m, 15H). Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 66% | 8% | 57% | 46% |

EXAMPLE 88

A compound of the following structure:

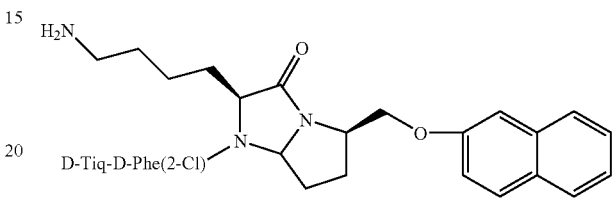

D-Tiq-D-Phe(2-Cl)

was synthesized by the general method of scheme 6 as set forth in Example 8. The molecular weight was determined to be 694.2 ESI-MS (M+1) by the method of Example 2. ($^1$H NMR, CD$_3$OD) δ: 1.0-1.8 (m, 6H), 2.15 (m, 2H), 2.4 (m, 2H), 2.7 (m, 4H), 3.15 (m, 3H), 3.45 (m, 3H), 3.75 (m, 3H), 4.15 (m, 1H), 4.2-4.5 (m, 3H), 5.0-5.55 (m, 3H), 6.8-7.9 (m, 15H). Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 48% | 0% | 37% | 20% |

EXAMPLE 89

A compound of the following structure:

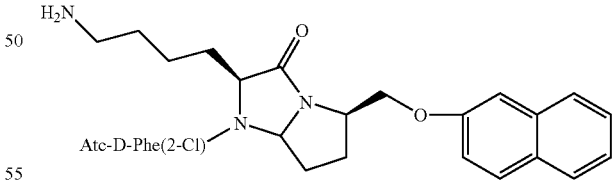

Atc-D-Phe(2-Cl)

was synthesized by the general method of scheme 6 as set forth in Example 8. The molecular weight was determined to be 708.2 ESI-MS (M+1) by the method of Example 2. ($^1$H NMR, CD$_3$OD) δ: 1.0-2.0 (m, 8H), 2.1-2.5 (m, 4H), 2.7 (m, 2H), 2.9-3.1 (m, 4H), 3.4 (m, 1H), 3.6 (m, 1H), 4.15 (m, 1H), 4.25-4.5 (m, 3H), 5.05 (m, 1H), 5.35 (m, 2H), 6.8-7.9 (m, 15H). Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 24% | 0% | 34% | 22% |

EXAMPLE 90

A compound of the following structure:

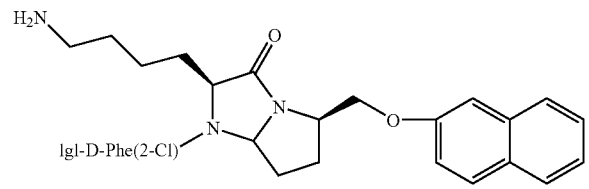

was synthesized by the general method of scheme 6 as set forth in Example 8. The molecular weight was determined to be 708.2 ESI-MS (M+1) by the method of Example 2. ($^1$H NMR, CD$_3$OD) δ: 1.1-2.0 (m, 6H), 2.2 (m, 2H), 2.5 (m, 2H), 2.65-2.9 (m, 6H), 3.05 (m, 1H), 3.25 (m, 1H)), 3.95 (m, 1H), 4.2 (m, 1H), 4.3-4.5 (m, 3H), 5.0-5.5 (m, 3H), 6.8-7.9 (m, 15H). Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 10% | 0% | 12% | 46% |

EXAMPLE 91

A compound of the following structure:

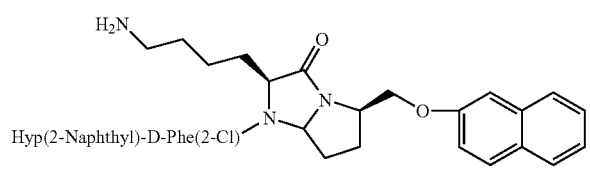

was synthesized by the general method of scheme 6 as set forth in Example 8. The molecular weight was determined to be 774.2 ESI-MS (M+1) by the method of Example 2. ($^1$H NMR, CD$_3$OD) δ: 1.1-2.0 (m, 6H), 2.0-2.9 (m, 8H), 2.95 (m, 1H), 3.15 (m, 1H), 3.55 (m, 1H), 365 (m, 1H), 4.15 (m, 1H), 4.3-4.5 (m, 3H), 5.0-5.4 (m, 3H), 6.75-7.9 (m, 16H). Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 21% | 0% | 0% | 17% |

EXAMPLE 92

A compound of the following structure:

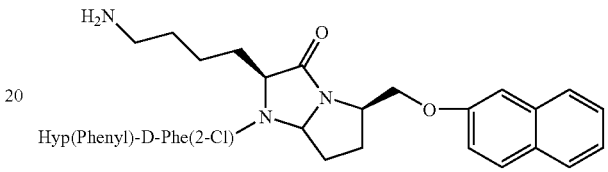

was synthesized by the general method of scheme 6 as set forth in Example 8. The molecular weight was determined to be 724.3 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 7% | 0% | 22% | 21% |

EXAMPLE 93

A compound of the following structure:

was synthesized by the general method of scheme 6 as set forth in Example 8. The molecular weight was determined to be 694.2 ESI-MS (M+1) by the method of Example 2. ($^1$H NMR, CD$_3$OD) δ: 0.9-1.85 (m, 6H), 1.95-2.85 (m, 6H), 2.95 (m, 1H), 3.05-3.55 (m, 4H), 3.55 (m, 1H), 3.65 (m, 1H), 3.9-4.5 (m, 7H), 5.0-5.4 (m, 2H), 6.75-7.9 (m, 15H). Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 47% | 12% | 79% | 18% |

EXAMPLE 94

A compound of the following structure:

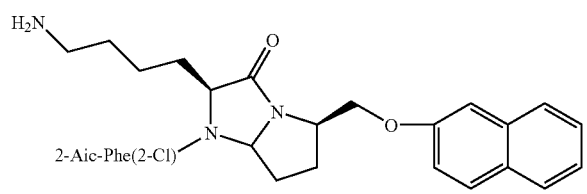

2-Aic-Phe(2-Cl)

was synthesized by the general method of scheme 6 as set forth in Example 8. The molecular weight was determined to be 693.9 ESI-MS (M+1) by the method of Example 2. ($^1$H NMR, CD$_3$OD) δ: 1.1-1.9 (m, 6H), 2.0-2.8 (m, 6H), 2.9-3.4 (m, 4H), 3.6 (m, 1H), 3.7 (m, 1H), 4.15-4.5 (m, 3H), 5.0-5.4 (m, 3H), 7.1-7.9 (m, 15H). Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 26% | 2% | 36% | 28% |

EXAMPLE 95

A compound of the following structure:

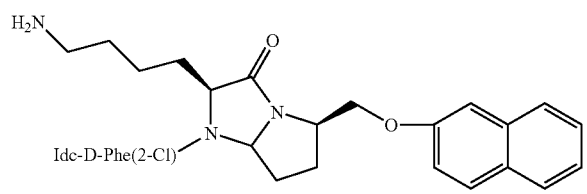

Idc-D-Phe(2-Cl)

was synthesized by the general method of scheme 6 as set forth in Example 8. The molecular weight was determined to be 679.9 ESI-MS (M+1) by the method of Example 2. ($^1$H NMR, CD$_3$OD) δ: 1.1-1.9 (m, 6H), 2.1-2.8 (m, 6H), 2.85-3.5 (m, 4H), 4.05-4.5 (m, 3H), 5.0-5.4 (m, 3H), 6.75-7.9 (m, 15H), Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 34% | 0% | 47% | 14% |

EXAMPLE 96

A compound of the following structure:

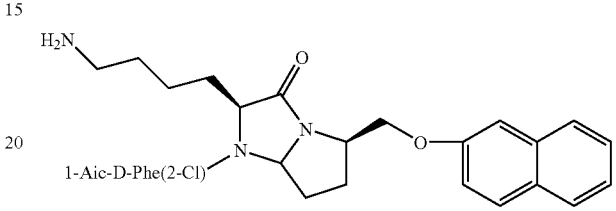

1-Aic-D-Phe(2-Cl)

was synthesized by the general method of scheme 6 as set forth in Example 8. The molecular weight was determined to be 694.2 ESI-MS (M+1) by the method of Example 2. ($^1$H NMR, CD$_3$OD) δ: 1.1-1.9 (m, 6H), 2.1-3.3 (m, 10H), 4.1-4.5 (m, 3H), 5.0-5.4 (m, 2H), 6.8-7.9 (m, 15H). Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 39% | 0% | 12% | 17% |

EXAMPLE 97

A compound of the following structure:

His-D-Phe was synthesized by the general method of scheme 6 as set forth in Example 8. The molecular weight was determined to be 666.1 ESI-MS (M+1) by the method of Example 2. ($^1$H NMR, CD$_3$OD) δ: 1.1-1.9 (m, 4H), 1.95-2.85 (m, 5H), 2.95-3.35 (m, 5H), 3.9-4.4 (m, 5H), 4.7-5.4 (m, 2H), 6.75-7.9 (m, 14H). Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 99% | 30% | 69% | 28% |

In a functional assay as in Example 4, this compound was a full agonist. The Ki was determined by the method of Example 4, with the following results:

| Ki (nM) | | | |
|---|---|---|---|
| MC1-R | MC3-R | MC4-R | MC5-R |
| 1 | >1 μM | 226 | >1 μM |

EXAMPLE 98

A compound of the following structure:

was synthesized by the general method of scheme 6 as set forth in Example 8. The molecular weight was determined to be 722.2 ESI-MS (M+1) by the method of Example 2. ($^1$H NMR, CD$_3$OD) δ: 1.1-1.9 (m, 4H), 2.0-2.55 (m, 4H), 2.7-3.2 (m, 6H), 4.1-4.55 (m, 5H), 4.9-5.5 (m, 2H), 7.15-7.9 (m, 15H). Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 77% | 42% | 98% | 87% |

In a cAMP assay as in Example 4 for determination of agonist/antagonist status, it was determined that the compound was an agonist as to MC1-R and MC4-R. The Ki was determined by the method of Example 4, with the following results:

| Ki (nM) | | | |
|---|---|---|---|
| MC1-R | MC3-R | MC4-R | MC5-R |
| 81 | 756 | 9 | 301 |

EXAMPLE 99

A compound of the following structure:

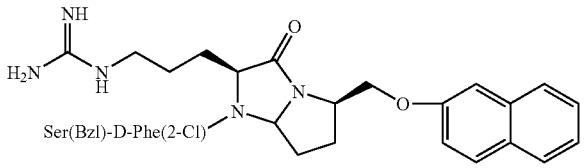

was synthesized by the general method of scheme 6 as set forth in Example 8. The molecular weight was determined to be 740.0 ESI-MS (M+1) by the method of Example 2. ($^1$H NMR, CD$_3$OD) δ: 1.1-1.9 (m, 4H), 2.0-2.5 (m, 3H), 2.7-3.2 (m, 5H), 3.5 (m, 1H), 3.7 (m, 1H), 4.05-4.6 (m, 7H), 4.9-5.5 (m, 2H), 7.15-7.9 (m, 16H). Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 57% | 29% | 94% | 94% |

In a cAMP assay as in Example 4 for determination of agonist/antagonist status, it was determined that the compound was an agonist as to MC1-R and MC4-R. The Ki was determined by the method of Example 4, with the following results:

| Ki (nM) | | | |
|---|---|---|---|
| MC1-R | MC3-R | MC4-R | MC5-R |
| 121 | >1 μM | 41 | 151 |

EXAMPLE 100

A compound of the following structure:

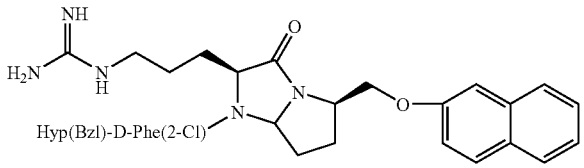

was synthesized by the general method of scheme 6 as set forth in Example 8. The molecular weight was determined to be 765.6 ESI-MS (M+1) by the method of Example 2. ($^1$H NMR, CD$_3$OD) δ: 1.2-1.95 (m, 4H), 2.0-2.95 (m, 6H), 2.0-3.2 (m, 4H), 3.4 (m, 1H), 3.5 (m, 1H), 4.1-4.55 (m, 7H), 4.9-5.5 (m, 2H), 7.15-7.9 (m, 16H). Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 54% | 40% | 95% | 93% |

In a cAMP assay as in Example 4 for determination of agonist/antagonist status, it was determined that the compound was an agonist as to MC1-R and MC4-R. The Ki was determined by the method of Example 4, with the following results:

| Ki (nM) | | | |
|---|---|---|---|
| MC1-R | MC3-R | MC4-R | MC5-R |
| 244 | 854 | 42 | 284 |

EXAMPLE 101

A compound of the following structure:

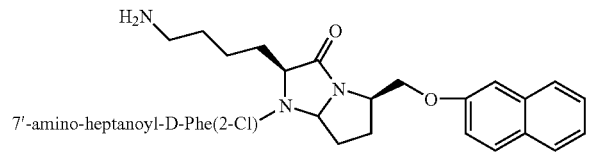

7'-amino-heptanoyl-D-Phe(2-Cl)

was synthesized by the general method of scheme 6 as set forth in Example 8. The molecular weight was determined to be 689.5 ESI-MS (M+1) by the method of Example 2. ($^1$H NMR, CD$_3$OD) δ: 1.2-2.0 (m, 12H), 2.0-2.95 (m, 6H), 2.1-3.3 (m, 12H), 4.0-4.5 (m, 4H), 4.9-5.5 (m, 2H), 7.15-7.9 (m, 11H). Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 95% | 6% | 81% | 36% |

EXAMPLE 102

A compound of the following structure:

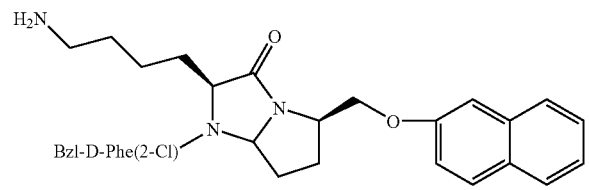

Bzl-D-Phe(2-Cl)

was synthesized by the general method of scheme 6 as set forth in Example 8. The molecular weight was determined to be 624.9 ESI-MS (M+1) by the method of Example 2. ($^1$H NMR, CD$_3$OD) δ: 1.0-1.75 (m, 6H), 1.85 (m, 1H), 2.15 (m, 1H), 2.3-2.8 (m, 4H), 3.3 (m, 2H), 3.6-4.6 (m, 7H), 4.8-5.5 (m, 1H), 7.1-7.9 (m, 16H). Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 11% | 13% | 16% | 14% |

EXAMPLE 103

A compound of the following structure:

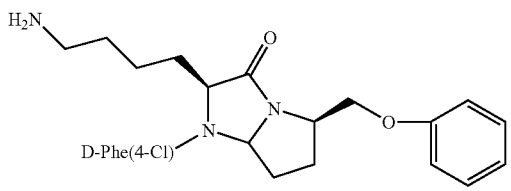

D-Phe(4-Cl)

was synthesized by the general method of scheme 6 as set forth in Example 8. The molecular weight was determined to be 485.0 ESI-MS (M+1) by the method of Example 2. ($^1$H NMR, CD$_3$OD) δ: 1.0-1.75 (m, 6H), 1.85 (m, 1H), 2.15 (m, 1H), 2.25-2.8 (m, 4H), 3.2 (m, 2H), 3.65-4.55 (m, 5H), 4.8-5.5 (m, 1H), 6.9-8.0 (m, 9H). Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 9% | 0% | 0% | 0% |

EXAMPLE 104

A compound of the following structure:

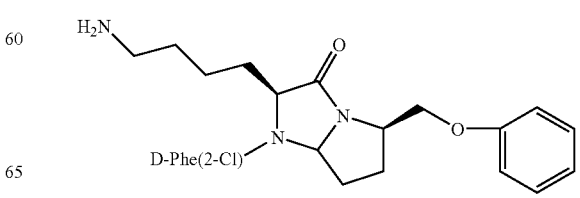

D-Phe(2-Cl)

was synthesized by the general method of scheme 6 as set forth in Example 8. The molecular weight was determined to be 484.9 ESI-MS (M+1) by the method of Example 2. ($^1$H NMR, CD$_3$OD) δ: 1.1-1.85 (m, 6H), 1.9 (m, 1H), 2.15 (m, 1H), 2.25-2.85 (m, 4H), 3.35 (m, 2H), 3.6-4.6 (m, 5H), 4.8-5.5 (m, 1H), 6.9-8.0 (m, 9H). Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 0% | 4% | 0% | 0% |

EXAMPLE 105

A compound of the following structure:

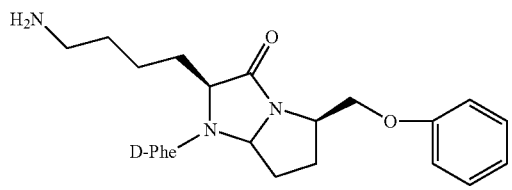

was synthesized by the general method of scheme 6 as set forth in Example 8. The molecular weight was determined to be 450.9 ESI-MS (M+1) by the method of Example 2. ($^1$H NMR, CD$_3$OD) δ: 1.1-1.75 (m, 6H), 1.85 (m, 1H), 2.15 (m, 1H), 2.45 (m, 1H), 2.65 (m, 1H), 2.8 (m, 2H), 3.2 (m, 2H), 3.4-4.5 (m, 5H), 4.6-5.5 (m, 1H), 6.9-7.5 (m, 10H). Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 1% | 4% | 0% | 0% |

EXAMPLE 106

A compound of the following structure:

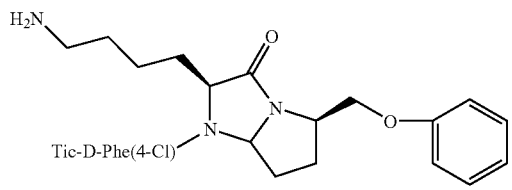

was synthesized by the general method of scheme 6 as set forth in Example 8. The molecular weight was determined to be 644.0 ESI-MS (M+1) by the method of Example 2. ($^1$H NMR, CD$_3$OD) δ: 1.0-1.85 (m, 6H), 2.15 (m, 2H), 2.35-2.85 (m, 4H), 3.0 (m, 2H), 3.15 (m, 2H), 4.0-4.5 (m, 6H), 4.8-5.4 (m, 2H), 6.9-7.5 (m, 13H). Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 81% | 19% | 51% | 25% |

EXAMPLE 107

A compound of the following structure:

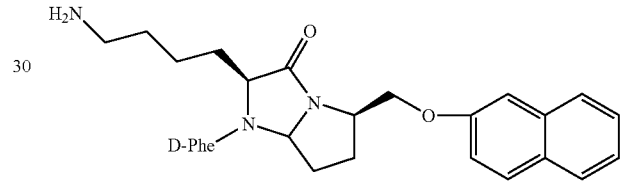

was synthesized by the general method of scheme 6 as set forth in Example 8. The molecular weight was determined to be 501.2 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 46% | 13% | 0% | 1% |

EXAMPLE 108

A compound of the following structure:

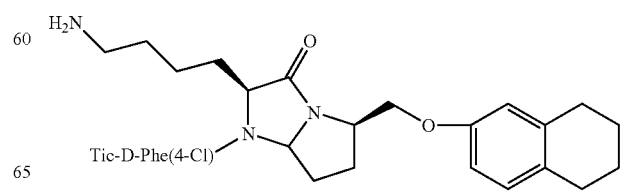

was synthesized by the general method of scheme 6 as set forth in Example 8. The molecular weight was determined to be 698.5 ESI-MS (M+1) by the method of Example 2. ($^1$H NMR, CD$_3$OD) δ: 1.0-1.9 (m, 10H), 2.0-2.45 (m, 4H), 2.6-3.1 (m, 8H), 3.2 (m, 2H), 3.95-4.5 (m, 6H), 5.0-5.4 (m, 1H), 6.4-7.5 (m, 11H). Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 96% | 19% | 94% | 66% |

EXAMPLE 109

A compound of the following structure:

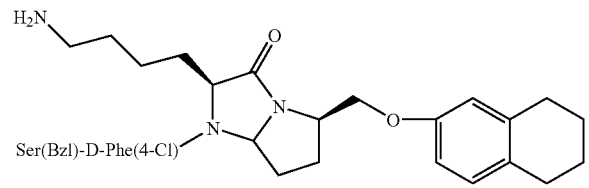

Ser(Bzl)-D-Phe(4-Cl)

was synthesized by the general method of scheme 6 as set forth in Example 8. The molecular weight was determined to be 716.5 ESI-MS (M+1) by the method of Example 2. ($^1$H NMR, CD$_3$OD) δ: 1.0-1.9 (m, 10H), 2.0-2.45 (m, 4H), 2.55-3.15 (m, 8H), 2.5-3.75 (m, 2H), 3.85-4.65 (m, 7H), 4.7-5.4 (m, 2H), 6.4-7.5 (m, 12H). Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 93% | 4% | 78% | 56% |

EXAMPLE 110

A compound of the following structure:

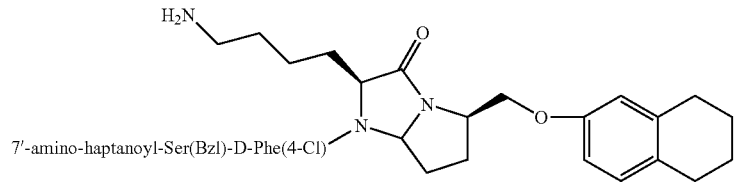

7'-amino-haptanoyl-Ser(Bzl)-D-Phe(4-Cl)

was synthesized by the general method of scheme 6 as set forth in Example 8. The molecular weight was determined to be 843.4 ESI-MS (M+1) by the method of Example 2. ($^1$H NMR, CD$_3$OD) δ: 1.0-1.9 (m, 18H), 2.0-3.05 (m, 16H), 3.7 (m, 2H), 3.9-4.65 (m, 7H), 4.7-5.4 (m, 2H), 6.4-7.5 (m, 12H). Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 97% | 59% | 96% | 84% |

EXAMPLE 111

A compound of the following structure:

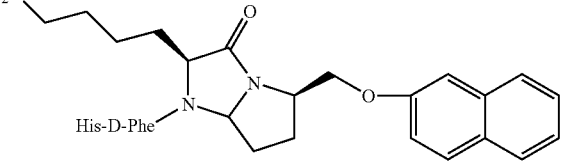

His-D-Phe was synthesized by the general method of scheme 6 as set forth in Example 8. The molecular weight was determined to be 658.1 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 94% | 9% | 10% | 0% |

EXAMPLE 112

A compound of the following structure:

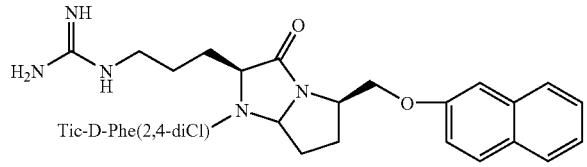

was synthesized by the general method of scheme 6 as set forth in Example 8. The molecular weight was determined to be 757.2 ESI-MS (M+1) by the method of Example 2. ($^1$H NMR, CD$_3$OD) δ: 1.3-1.95 (m, 4H), 2.0-2.5 (m, 3H), 2.7-2.95 (m, 4H), 3.05-3.25 (m, 3H), 3.3 (m, 2H), 4.1-4.55 (m, 7H), 5.0-5.6 (m, 2H), 7.1-7.9 (m, 14H). Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 75% | 88% | 100% | 96% |

In a cAMP assay as in Example 4 for determination of agonist/antagonist status, it was determined that the compound was inactive as to MC1-5, and an antagonist as to MC4-R and MC-5. The Ki was determined by the method of Example 4, with the following results:

| Ki (nM) | | | |
|---|---|---|---|
| MC1-R | MC3-R | MC4-R | MC5-R |
| 111 | 42 | 1 | 26 |

EXAMPLE 113

A compound of the following structure:

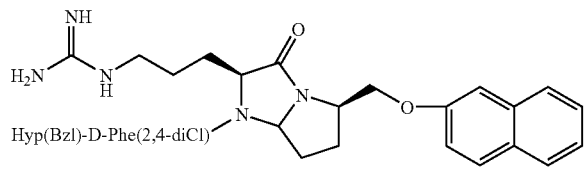

was synthesized by the general method of scheme 6 as set forth in Example 8. The molecular weight was determined to be 801.1 ESI-MS (M+1) by the method of Example 2. ($^1$H NMR, CD$_3$OD) δ: 1.3-1.95 (m, 4H), 2.0-2.7 (m, 4H), 2.55-3.15 (m, 4H), 3.3 (m, 2H), 3.5 (m, 2H), 4.1-4.65 (m, 7H), 5.0-5.6 (m, 2H), 7.1-7.9 (m, 15H) Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 53% | 84% | 100% | 100% |

In a cAMP assay as in Example 4 for determination of agonist/antagonist status, it was determined that the compound was an agonist as to MC1-R and MC5-R and an antagonist as to MC4-R.

EXAMPLE 114

A compound of the following structure:

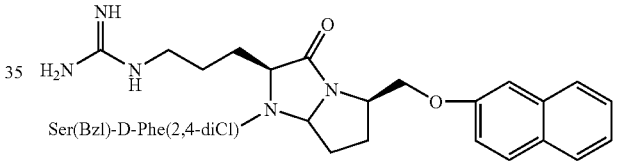

was synthesized by the general method of scheme 6 as set forth in Example 8. The molecular weight was determined to be 775.0 ESI-MS (M+1) by the method of Example 2. ($^1$H NMR, CD$_3$OD) δ: 1.3-1.95 (m, 4H), 2.0-2.5 (m, 3H), 2.65-3.2 (m, 5H), 3.5 (m, 1H), 3.7 (m, 1H), 3.75-4.65 (m, 7H), 5.0-5.6 (m, 2H), 7.1-7.9 (m, 15H). Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 53% | 77% | 100% | 94% |

In a cAMP assay as in Example 4 for determination of agonist/antagonist status, it was determined that the compound was an agonist as to MC1-R, MC4-R and MC5-R.

EXAMPLE 115

A compound of the following structure:

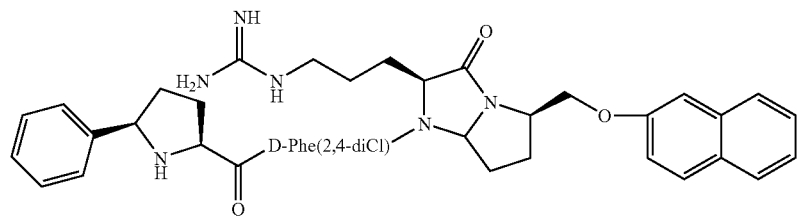

was synthesized by the general method of scheme 6 as set forth in Example 8. The molecular weight was determined to be 770.3 ESI-MS (M+1) by the method of Example 2. ($^1$H NMR, CD$_3$OD) δ: 1.3-1.95 (m, 4H), 2.0-2.55 (m, 6H), 2.75-3.3 (m, 6H), 4.1-4.7 (m, 5H), 5.1-5.6 (m, 2H), 7.1-7.9 (m, 15H). Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 16% | 43% | 97% | 86% |

In a cAMP assay as in Example 4 for determination of agonist/antagonist status, it was determined that the compound was an agonist as to MC1-R and MC-5 and an antagonist as to MC4-R. The Ki was determined by the method of Example 4, with the following results:

| Ki (nM) | | | |
|---|---|---|---|
| MC1-R | MC3-R | MC4-R | MC5-R |
| >1 μM | >1 μM | 12 | 99 |

EXAMPLE 116

A compound of the following structure:

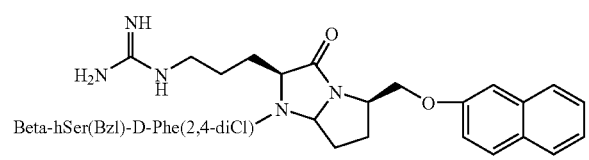

was synthesized by the general method of scheme 6 as set forth in Example 8. The molecular weight was determined to be 788.3 ESI-MS (M+1) by the method of Example 2. ($^1$H NMR, CD$_3$OD) δ: 1.2-1.9 (m, 4H), 1.9-2.75 (m, 6H), 3.0-3.25 (m, 4H), 3.45 (m, 1H), 3.6 (m, 1H), 3.7 (m, 1H), 4.15-4.65 (m, 6H), 5.0-5.4 (m, 2H), 7.1-7.9 (m, 15H). Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 65% | 77% | 99% | 96% |

EXAMPLE 117

A compound of the following structure:

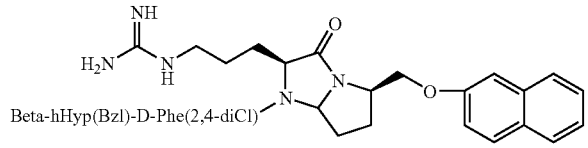

was synthesized by the general method of scheme 6 as set forth in Example 8. The molecular weight was determined to be 814.3 ESI-MS (M+1) by the method of Example 2. ($^1$H NMR, CD$_3$OD) δ: 1.3-1.95 (m, 4H), 2.0-2.5 (m, 4H), 2.6-3.25 (m, 8H), 3.35 (m, 1H), 3.45 (m, 1H), 4.05 (m, 1H), 4.15-4.65 (m, 7H), 4.9-5.5 (m, 2H), 7.1-7.9 (m, 15H). Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 59% | 88% | 99% | 95% |

EXAMPLE 118

A compound of the following structure:

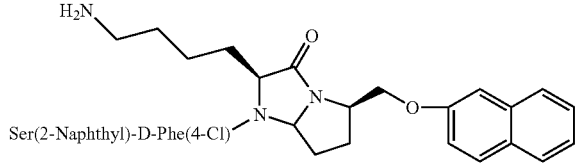

was synthesized by the general method of scheme 6 as set forth in Example 8. The molecular weight was determined to be 762.4 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 51% | 23% | 53% | 54% |

EXAMPLE 119

A compound of the following structure:

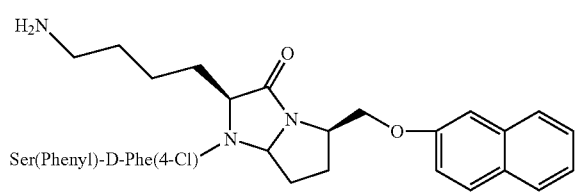

was synthesized by the general method of scheme 6 as set forth in Example 8. The molecular weight was determined to be 712.2 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 72% | 20% | 56% | 52% |

EXAMPLE 120

A compound of the following structure:

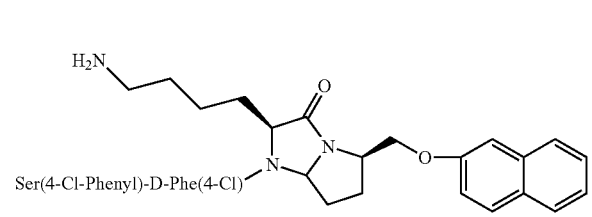

was synthesized by the general method of scheme 6 as set forth in Example 8. The molecular weight was determined to be 746.2 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 52% | 28% | 37% | 40% |

EXAMPLE 121

A compound of the following structure:

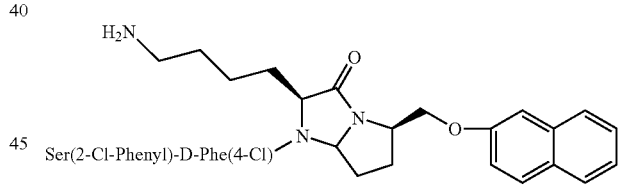

was synthesized by the general method of scheme 6 as set forth in Example 8. The molecular weight was determined to be 746.2 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 42% | 15% | 37% | 22% |

EXAMPLE 122

A compound of the following structure:

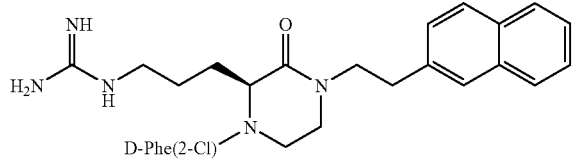

was synthesized by the general method of scheme 8 as set forth in Example 10. The molecular weight was determined to be 534.4 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 3% | 2% | 69% | 5% |

EXAMPLE 123

A compound of the following structure:

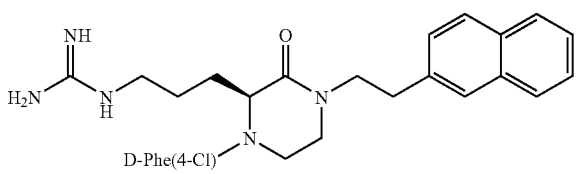

was synthesized by the general method of scheme 8 as set forth in Example 10. The molecular weight was determined to be 534.5 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 34% | 38% | 87% | 29% |

EXAMPLE 124

A compound of the following structure:

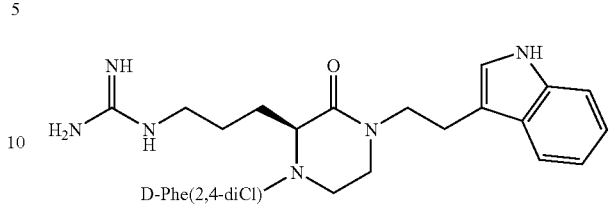

was synthesized by the general method of scheme 8 as set forth in Example 10. The molecular weight was determined to be 557.5 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 7% | 57% | 96% | 35% |

EXAMPLE 125

A compound of the following structure:

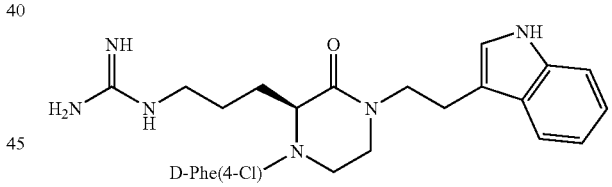

was synthesized by the general method of scheme 8 as set forth in Example 10. The molecular weight was determined to be 523.6 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 10% | 28% | 68% | 43% |

EXAMPLE 126

A compound of the following structure:

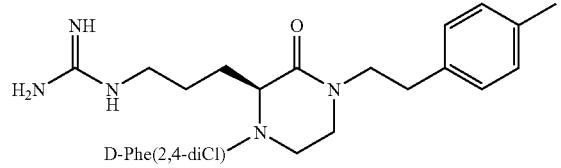

was synthesized by the general method of scheme 8 as set forth in Example 10. The molecular weight was determined to be 532.4 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 µM | | | |
|---|---|---|---|
| MC1-R | MC3-R | MC4-R | MC5-R |
| 11% | 42% | 78% | 34% |

EXAMPLE 127

A compound of the following structure:

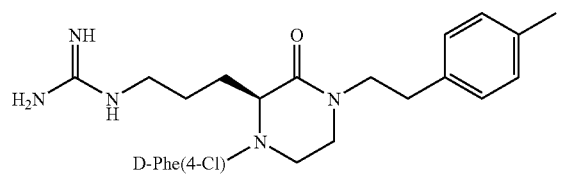

was synthesized by the general method of scheme 8 as set forth in Example 10. The molecular weight was determined to be 498.6 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 µM | | | |
|---|---|---|---|
| MC1-R | MC3-R | MC4-R | MC5-R |
| 9% | 9% | 49% | 17% |

EXAMPLE 128

A compound of the following structure:

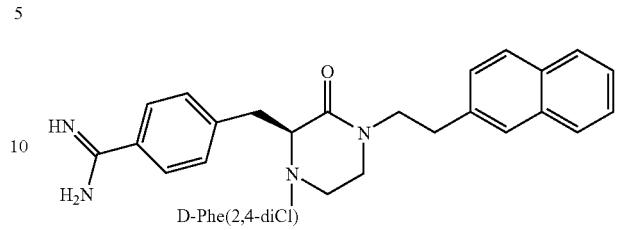

was synthesized by the general method of scheme 8 as set forth in Example 10. The molecular weight was determined to be 601.5 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 µM | | | |
|---|---|---|---|
| MC1-R | MC3-R | MC4-R | MC5-R |
| 5% | 0% | 31% | 21% |

EXAMPLE 129

A compound of the following structure:

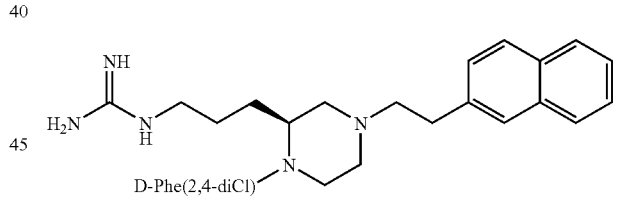

was synthesized by the general method of scheme 8 as set forth in Example 10. The molecular weight was determined to be 512.0 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 µM | | | |
|---|---|---|---|
| MC1-R | MC3-R | MC4-R | MC5-R |
| 6% | 87% | 99% | 75% |

EXAMPLE 130

A compound of the following structure:

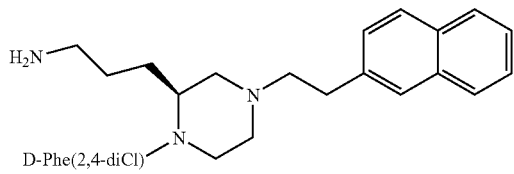

was synthesized by a modification of the general method of scheme 8 as set forth in Example 10. The molecular weight was determined to be 554.1 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 0% | 33% | 81% | 39% |

EXAMPLE 131

A compound of the following structure:

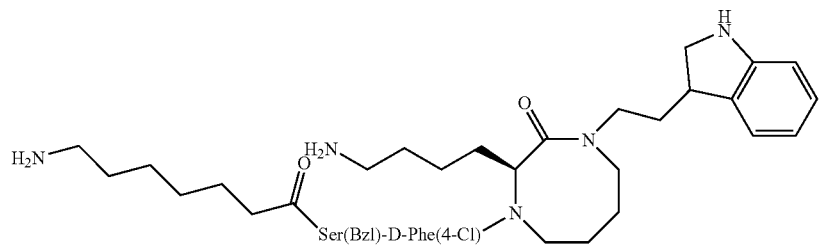

was synthesized by a modification of the general method of scheme 8 as set forth in Example 10. The molecular weight was determined to be 828.7 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 36% | 0% | 31% | 17% |

EXAMPLE 132

A compound of the following structure:

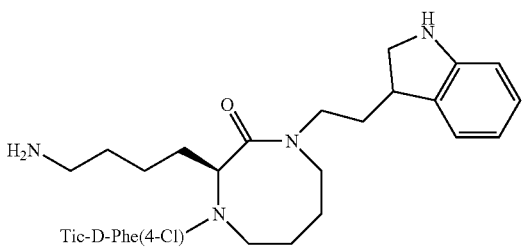

was synthesized by a modification of the general method of scheme 8 as set forth in Example 10. The molecular weight was determined to be 683.9 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 20% | 0% | 25% | 31% |

EXAMPLE 133

A compound of the following structure:

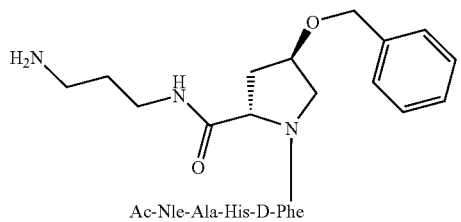

was synthesized by the general method of scheme 1 as set forth in Example 5. The molecular weight was determined to be 788.6 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 91% | 13% | 8% | 25% |

In a cAMP assay as in Example 4 for determination of agonist/antagonist status, it was determined that the metallopeptide was an agonist of MC1-R. The Ki was determined by the method of Example 4, with the following results:

| Ki (nM) | | | |
|---|---|---|---|
| MC1-R | MC3-R | MC4-R | MC5-R |
| 10 | >1 μM | >1 μM | >1 μM |

EXAMPLE 134

A compound of the following structure:

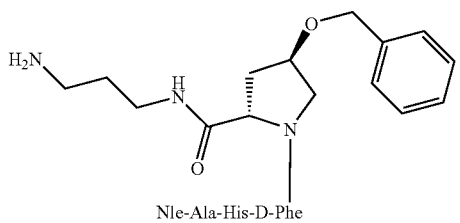

Nle-Ala-His-D-Phe was synthesized by the general method of scheme 1 as set forth in Example 5. The molecular weight was determined to be 746.6 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 83% | 6% | 2% | 7% |

The Ki was determined by the method of Example 4, with the following results:

| Ki (nM) | | | |
|---|---|---|---|
| MC1-R | MC3-R | MC4-R | MC5-R |
| 70 | >1 μM | >1 μM | >1 μM |

EXAMPLE 135

A compound of the following structure:

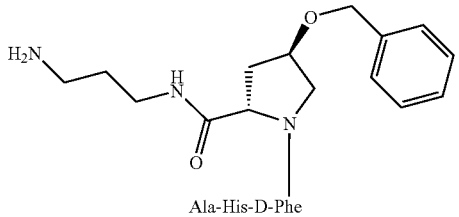

Ala-His-D-Phe was synthesized by the general method of scheme 1 as set forth in Example 5. The molecular weight was determined to be 633.4 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 93% | 0% | 0% | 0% |

EXAMPLE 136

A compound of the following structure:

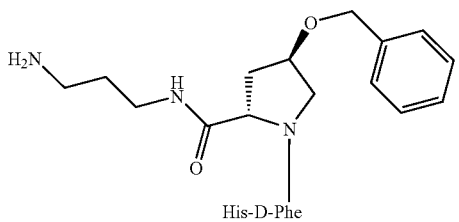

His-D-Phe was synthesized by the general method of scheme 1 as set forth in Example 5. The molecular weight was determined to be 562.4 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 48% | 0% | 0% | 2% |

EXAMPLE 137

A compound of the following structure:

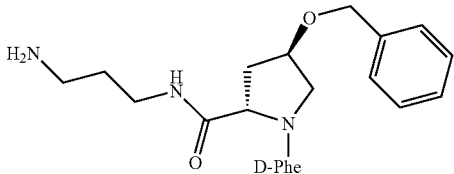

was synthesized by the general method of scheme 1 as set forth in Example 5. The molecular weight was determined to be 425.4 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 23% | 0% | 0% | 0% |

EXAMPLE 138

A compound of the following structure:

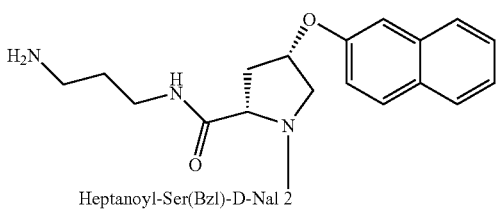

was synthesized by the general method of Example 5. The molecular weight was determined to be 800.4 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 39% | 0% | 0% | 0% |

EXAMPLE 139

A compound of the following structure:

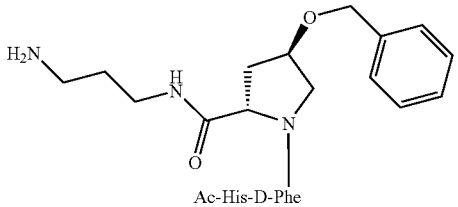

was synthesized by the general method of scheme 1 as set forth in Example 5. The molecular weight was determined to be 604.0 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 85% | 46% | 43% | 34% |

EXAMPLE 140

A compound of the following structure:

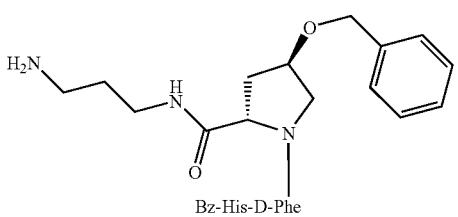

was synthesized by the general method of scheme 1 as set forth in Example 5. The molecular weight was determined to be 666.2 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 78% | 3% | 1% | 10% |

EXAMPLE 141

A compound of the following structure:

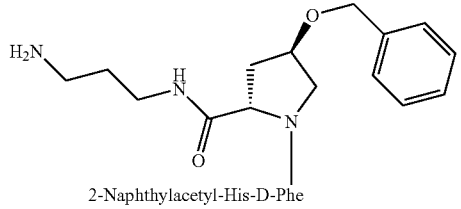

2-Naphthylacetyl-His-D-Phe was synthesized by the general method of scheme 1 as set forth in Example 5. The molecular weight was determined to be 730.2 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 84% | 4% | 0% | 19% |

EXAMPLE 142

A compound of the following structure:

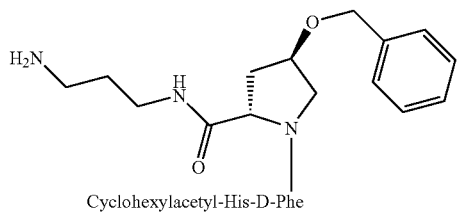

Cyclohexylacetyl-His-D-Phe was synthesized by the general method of scheme 1 as set forth in Example 5. The molecular weight was determined to be 686.2 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 85% | 3% | 0% | 12% |

EXAMPLE 143

A compound of the following structure:

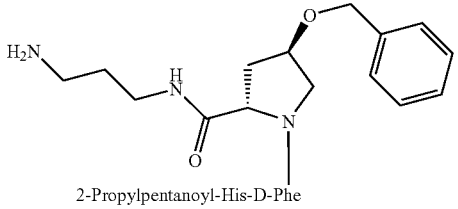

2-Propylpentanoyl-His-D-Phe was synthesized by the general method of scheme 1 as set forth in Example 5. The molecular weight was determined to be 688.2 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 73% | 0% | 0% | 7% |

EXAMPLE 144

A compound of the following structure:

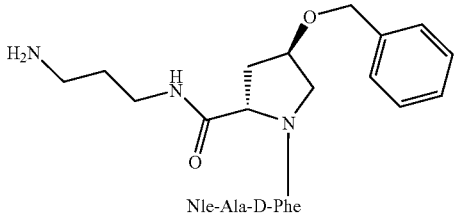

Nle-Ala-D-Phe was synthesized by the general method of scheme 1 as set forth in Example 5. The molecular weight was determined to be 771.4 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 20% | 0% | 3% | 24% |

EXAMPLE 145

A compound of the following structure:

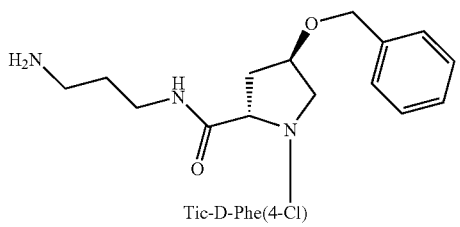

Tic-D-Phe(4-Cl)

was synthesized by the general method of scheme 1 as set forth in Example 5. The molecular weight was determined to be 618.4 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 µM | | | |
|---|---|---|---|
| MC1-R | MC3-R | MC4-R | MC5-R |
| 40% | 6% | 29% | 48% |

The Ki was determined by the method of Example 4, with the following results:

| Ki (nM) | | | |
|---|---|---|---|
| MC1-R | MC3-R | MC4-R | MC5-R |
| >1 µM | >1 µM | >1 µM | 1146 |

EXAMPLE 146

A compound of the following structure:

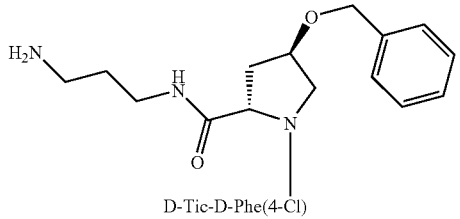

D-Tic-D-Phe(4-Cl)

was synthesized by the general method of scheme 1 as set forth in Example 5. The molecular weight was determined to be 618.0 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 µM | | | |
|---|---|---|---|
| MC1-R | MC3-R | MC4-R | MC5-R |
| 29% | 10% | 27% | 38% |

The Ki was determined by the method of Example 4, with the following results:

| Ki (nM) | | | |
|---|---|---|---|
| MC1-R | MC3-R | MC4-R | MC5-R |
| >1 µM | >1 µM | >1 µM | >1 µM |

EXAMPLE 147

A compound of the following structure:

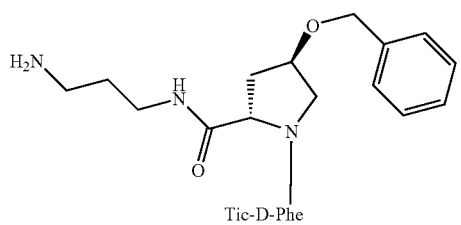

Tic-D-Phe was synthesized by the general method of scheme 1 as set forth in Example 5. The molecular weight was determined to be 584.4 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 µM | | | |
|---|---|---|---|
| MC1-R | MC3-R | MC4-R | MC5-R |
| 34% | 0% | 6% | 14% |

The Ki was determined by the method of Example 4, with the following results:

| Ki (nM) | | | |
|---|---|---|---|
| MC1-R | MC3-R | MC4-R | MC5-R |
| >1 µM | >1 µM | >1 µM | >1 µM |

EXAMPLE 148

A compound of the following structure:

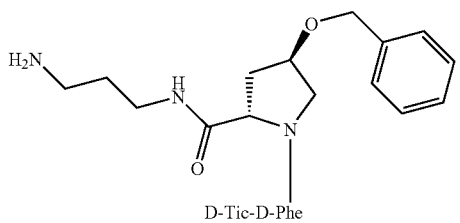

D-Tic-D-Phe was synthesized by the general method of scheme 1 as set forth in Example 5. The molecular weight was determined to be 584.4 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
| --- | --- | --- | --- |
| MC1-R | MC3-R | MC4-R | MC5-R |
| 17% | 0% | 5% | 0% |

The Ki was determined by the method of Example 4, with the following results:

| Ki (nM) | | | |
| --- | --- | --- | --- |
| MC1-R | MC3-R | MC4-R | MC5-R |
| >1 μM | >1 μM | >1 μM | >1 μM |

EXAMPLE 149

A compound of the following structure:

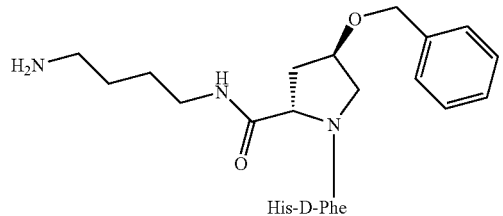

His-D-Phe was synthesized by the general method of scheme 1 as set forth in Example 5. The molecular weight was determined to be 576.5 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
| --- | --- | --- | --- |
| MC1-R | MC3-R | MC4-R | MC5-R |
| 50% | 12% | 2% | 7% |

EXAMPLE 150

A compound of the following structure:

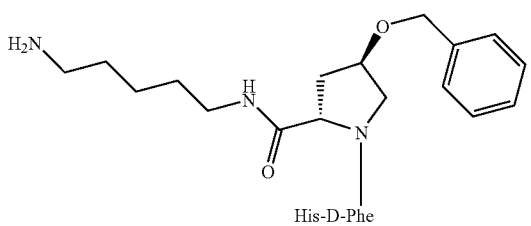

His-D-Phe was synthesized by the general method of scheme 1 as set forth in Example 5. The molecular weight was determined to be 590.4 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
| --- | --- | --- | --- |
| MC1-R | MC3-R | MC4-R | MC5-R |
| 42% | 0% | 1% | 7% |

EXAMPLE 151

A compound of the following structure:

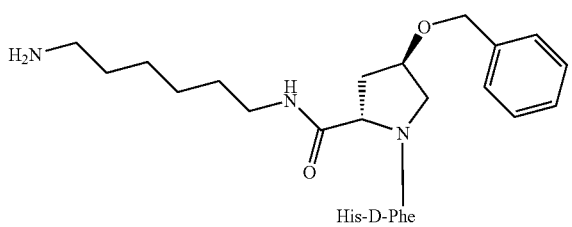

His-D-Phe was synthesized by the general method of scheme 1 as set forth in Example 5. The molecular weight was determined to be 604.3 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 36% | 0% | 2% | 8% |

EXAMPLE 152

A compound of the following structure:

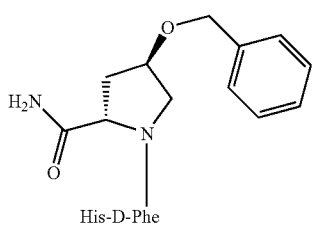

His-D-Phe was synthesized by the general method of scheme 1 as set forth in Example 5. The molecular weight was determined to be 505.4 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 0% | 0% | 0% | 5% |

EXAMPLE 153

A compound of the following structure:

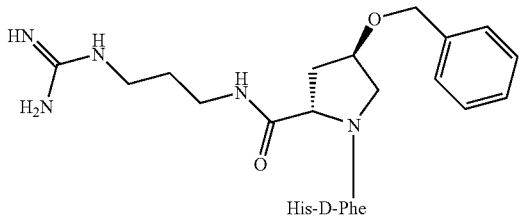

His-D-Phe was synthesized by the general method of scheme 1 as set forth in Example 5. The molecular weight was determined to be 604.6 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 0% | 0% | 6% | 4% |

EXAMPLE 154

A compound of the following structure:

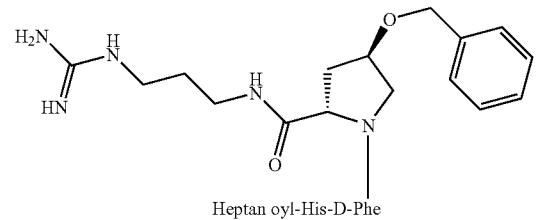

Heptan oyl-His-D-Phe was synthesized by the general method of scheme 1 as set forth in Example 5. The molecular weight was determined to be 716.5 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 92% | 7% | 1% | 1% |

EXAMPLE 155

A compound of the following structure:

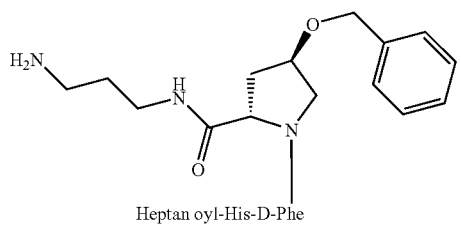

Heptan oyl-His-D-Phe was synthesized by the general method of scheme 1 as set forth in Example 5. The molecular weight was determined to be 674.5 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 71% | 5% | 0% | 7% |

EXAMPLE 156

A compound of the following structure:

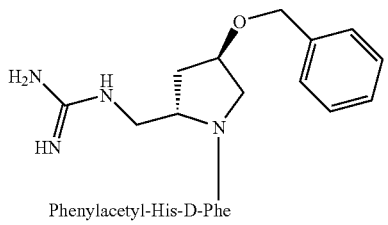

Phenylacetyl-His-D-Phe was synthesized by the general method of scheme 1 as set forth in Example 5. The molecular weight was determined to be 701.6 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 38% | 4% | 7% | 11% |

EXAMPLE 157

A compound of the following structure:

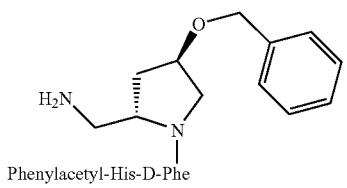

Phenylacetyl-His-D-Phe was synthesized by the general method of scheme 1 as set forth in Example 5. The molecular weight was determined to be 659.4 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 40% | 0% | 2% | 19% |

EXAMPLE 158

A compound of the following structure:

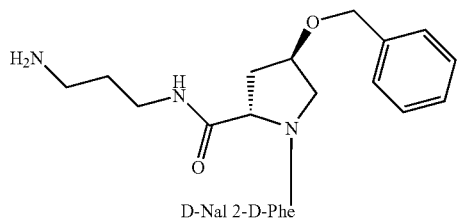

D-Nal 2-D-Phe was synthesized by the general method of scheme 1 as set forth in Example 5. The molecular weight was determined to be 622.5 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 0% | 5% | 0% | 0% |

EXAMPLE 159

A compound of the following structure:

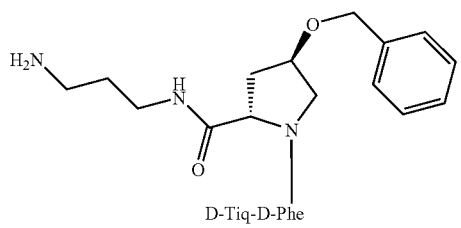

D-Tiq-D-Phe was synthesized by the general method of scheme 1 as set forth in Example 5. The molecular weight was determined to be 584.4 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 0% | 14% | 1% | 0% |

EXAMPLE 160

A compound of the following structure:

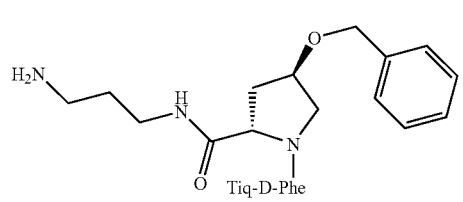

Tiq-D-Phe was synthesized by the general method of scheme 1 as set forth in Example 5. The molecular weight was determined to be 584.5 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 1% | 36% | 5% | 0% |

EXAMPLE 161

A compound of the following structure:

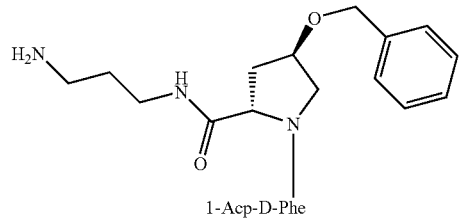

1-Acp-D-Phe was synthesized by the general method of scheme 1 as set forth in Example 5. The molecular weight was determined to be 536.5 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 3% | 23% | 10% | 0% |

EXAMPLE 162

A compound of the following structure:

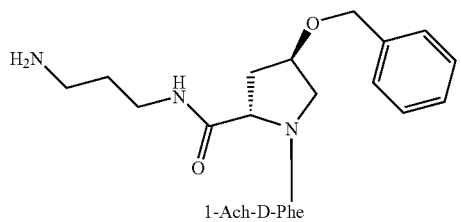

1-Ach-D-Phe was synthesized by the general method of scheme 1 as set forth in Example 5. The molecular weight was determined to be 550.3 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 0% | 41% | 8% | 0% |

EXAMPLE 163

A compound of the following structure:

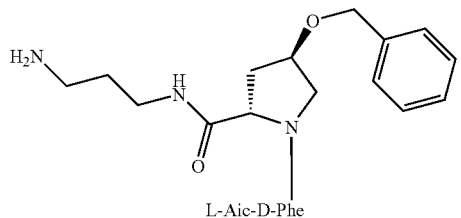

L-Aic-D-Phe was synthesized by the general method of scheme 1 as set forth in Example 5. The molecular weight was determined to be 584.5 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 0% | 16% | 15% | 0% |

EXAMPLE 164

A compound of the following structure:

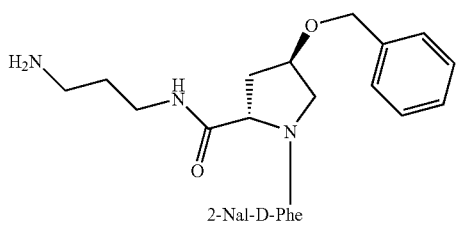

2-Nal-D-Phe was synthesized by the general method of scheme 1 as set forth in Example 5. The molecular weight was determined to be 622.5 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 0% | 0% | 13% | 1% |

EXAMPLE 165

A compound of the following structure:

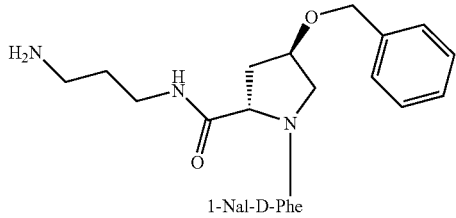

1-Nal-D-Phe was synthesized by the general method of scheme 1 as set forth in Example 5. The molecular weight was determined to be 622.5 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 0% | 2% | 16% | 0% |

EXAMPLE 166

A compound of the following structure:

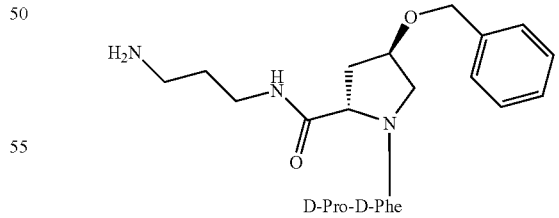

D-Nal 1-D-Phe was synthesized by the general method of scheme 1 as set forth in Example 5. The molecular weight was determined to be 622.2 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 0% | 13% | 8% | 0% |

EXAMPLE 167

A compound of the following structure:

D-Pro-D-Phe was synthesized by the general method of scheme 1 as set forth in Example 5. The molecular weight was determined to be 522.5 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 22% | 0% | 8% | 5% |

EXAMPLE 168

A compound of the following structure:

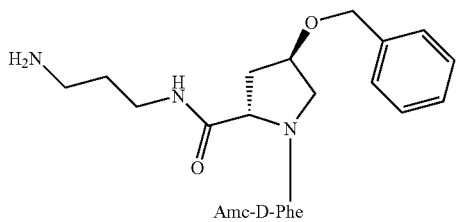

Amc-D-Phe was synthesized by the general method of scheme 1 as set forth in Example 5. The molecular weight was determined to be 564.3 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 18% | 0% | 10% | 0% |

EXAMPLE 169

A compound of the following structure:

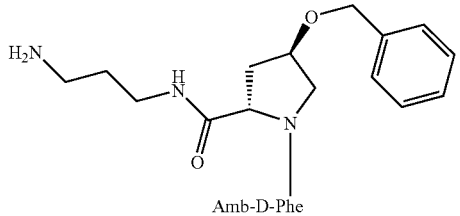

Amb-D-Phe was synthesized by the general method of scheme 1 as set forth in Example 5. The molecular weight was determined to be 558.2 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 12% | 0% | 6% | 0% |

EXAMPLE 170

A compound of the following structure:

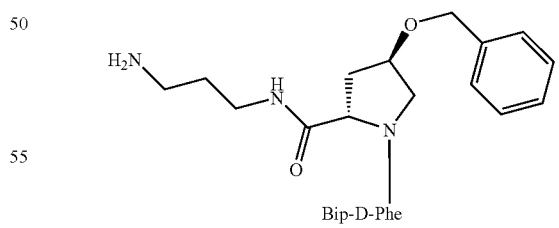

Pro-D-Phe was synthesized by the general method of scheme 1 as set forth in Example 5. The molecular weight was determined to be 522.3 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 13% | 0% | 11% | 0% |

EXAMPLE 171

A compound of the following structure:

Bip-D-Phe was synthesized by the general method of scheme 1 as set forth in Example 5. The molecular weight was determined to be 648.2 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 µM | | | |
|---|---|---|---|
| MC1-R | MC3-R | MC4-R | MC5-R |
| 11% | 0% | 9% | 25% |

EXAMPLE 172

A compound of the following structure:

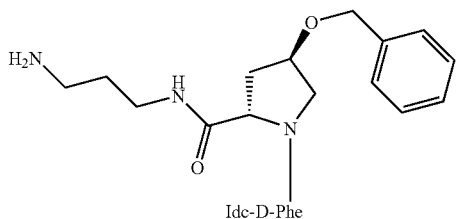

Idc-D-Phe was synthesized by the general method of scheme 1 as set forth in Example 5. The molecular weight was determined to be 570.2 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 µM | | | |
|---|---|---|---|
| MC1-R | MC3-R | MC4-R | MC5-R |
| 14% | 0% | 4% | 0% |

EXAMPLE 173

A compound of the following structure:

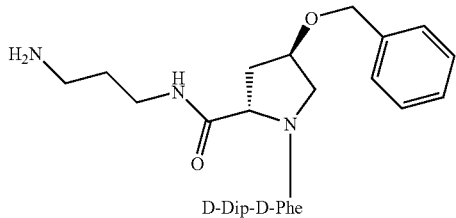

D-Dip-D-Phe was synthesized by the general method of scheme 1 as set forth in Example 5. The molecular weight was determined to be 648.3 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 µM | | | |
|---|---|---|---|
| MC1-R | MC3-R | MC4-R | MC5-R |
| 7% | 13% | 7% | 0% |

EXAMPLE 174

A compound of the following structure:

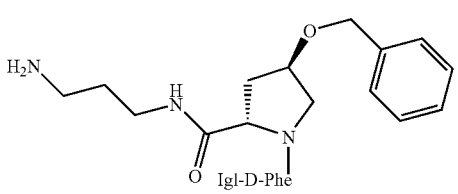

Igl-D-Phe was synthesized by the general method of scheme 1 as set forth in Example 5. The molecular weight was determined to be 598.5 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 µM | | | |
|---|---|---|---|
| MC1-R | MC3-R | MC4-R | MC5-R |
| 10% | 21% | 15% | 2% |

EXAMPLE 175

A compound of the following structure:

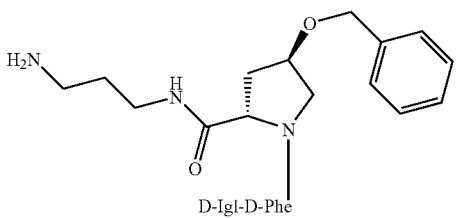

D-Igl-D-Phe was synthesized by the general method of scheme 1 as set forth in Example 5. The molecular weight was determined to be 598.3 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 3% | 0% | 19% | 0% |

EXAMPLE 176

A compound of the following structure:

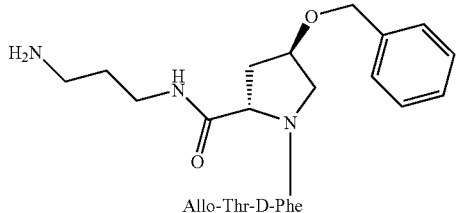

Allo-Thr-D-Phe was synthesized by the general method of scheme 1 as set forth in Example 5. The molecular weight was determined to be 526.3 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 18% | 0% | 8% | 8% |

EXAMPLE 177

A compound of the following structure:

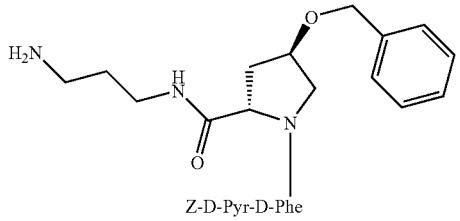

Z-D-Pyr-D-Phe was synthesized by the general method of scheme 1 as set forth in Example 5. The molecular weight was determined to be 670.4 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 2% | 0% | 7% | 0% |

EXAMPLE 178

A compound of the following structure:

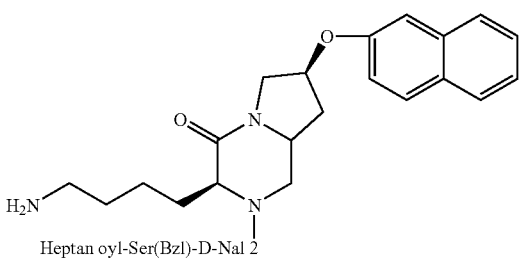

Heptan oyl-Ser(Bzl)-D-Nal 2 was synthesized by the general method of scheme 5 as set forth in Example 7. The molecular weight was determined to be 840.4 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 33% | 0% | 0% | 0% |

EXAMPLE 179

A compound of the following structure:

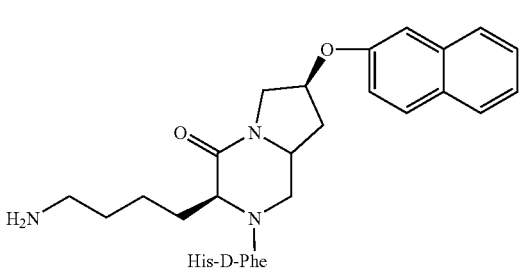

His-D-Phe was synthesized by the general method of scheme 5 as set forth in Example 7. The molecular weight was determined to be 638.4 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 0% | 0% | 0% | 0% |

EXAMPLE 180

A compound of the following structure:

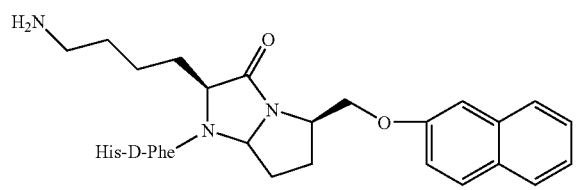

was synthesized by the general method of scheme 6 as set forth in Example 8. The molecular weight was determined to be 638.4 ESI-MS (M+1) by the method of Example 2. Competitive inhibition testing of the compound following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 94% | 9% | 10% | 0% |

In a cAMP assay as in Example 4 for determination of agonist/antagonist status, it was determined that the compound was an agonist as to MC1-R. The Ki was determined by the method of Example 4, with the following results:

| Ki (nM) | | | |
|---|---|---|---|
| MC1-R | MC3-R | MC4-R | MC5-R |
| 8 | >1 μM | >1 μM | >1 μM |

EXAMPLE 181

Determination of Induction of Penile Erection

The ability of compounds to induce penile erection (PE) in male rats is evaluated with selected melanocortin receptor-specific peptidomimetics. Male Sprague-Dawley rats weighing 200-250 g are kept on a 12 hour on/off light cycle with food and water ad libitum. All behavioral studies are performed between 10 a.m. and 5 p.m. Groups of 4-8 rats are treated with peptides at a variety of doses via intravenous (IV), subcutaneous (SC), intracerebroventricular (ICV), intraperitoneal (IP) injection or administered intranasally (IN) using a micropipetor to deliver 25 μL of solution into one nostril. Immediately after treatment, rats are placed into individual polystyrene cages (27 cm long, 16 cm wide, and 25 cm high) for behavioral observation. Rats are observed for 30 minutes and the number of yawns, grooming bouts and PEs are recorded in three 10-minute bins.

EXAMPLE 182

Effect on Food Intake and Body Weight

Food intake and body weight change are evaluated for selected melanocortin receptor-specific peptidomimetics. Male Sprague-Dawley rats weighing ~300 g at the beginning of the experiment are kept on a 12 hour on/of light cycle. Lights out is adjusted to 12:00 p.m. to allow for dosing just prior to the start of their dark period. Rats (12/group) are fed powdered chow and water ad libitum. For 1 week before treatment, 24-hour food intake and body weight change is recorded to assess a baseline for the group during vehicle treatment. The rats are dosed ICV, IV, SC or IP on day 0 and food intake and body weight measured daily for 1 week. Animals are dosed once per week for up to 6 weeks and their food intake and daily weight changed compared to their baseline.

EXAMPLE 183

Conditioned Taste Aversion

Conditioned taste aversion is evaluated in rats using peptidomimetics employed in Example 182. Male Sprague-Dawley rats weighing ~300 g are kept on a 12 hour on/of light cycle. Lights out is adjusted to 12:00 p.m. with food ad libitum. Animals are trained to be accustomed to 30 minutes of access to water per day. On day 1 of the experiment, rats are given 30 minutes of access to water containing 0.15% saccharin immediately prior to being dosed ICV, IV or IP with compound. On day two they are given plain water for the appointed time. On day 3 the rats are given saccharin-containing water again. The amount of fluid these animals consumed on day 1 and day 3 is compared. Reduced intake on day 3 indicates a conditioned taste aversion due to illness induced by drug treatment on day 1. LiCl treatment (127 mg/kg; IP) is used as a positive control.

EXAMPLE 184

Angiotensin Metallopeptide Derived Ring Compounds

Figure 3:
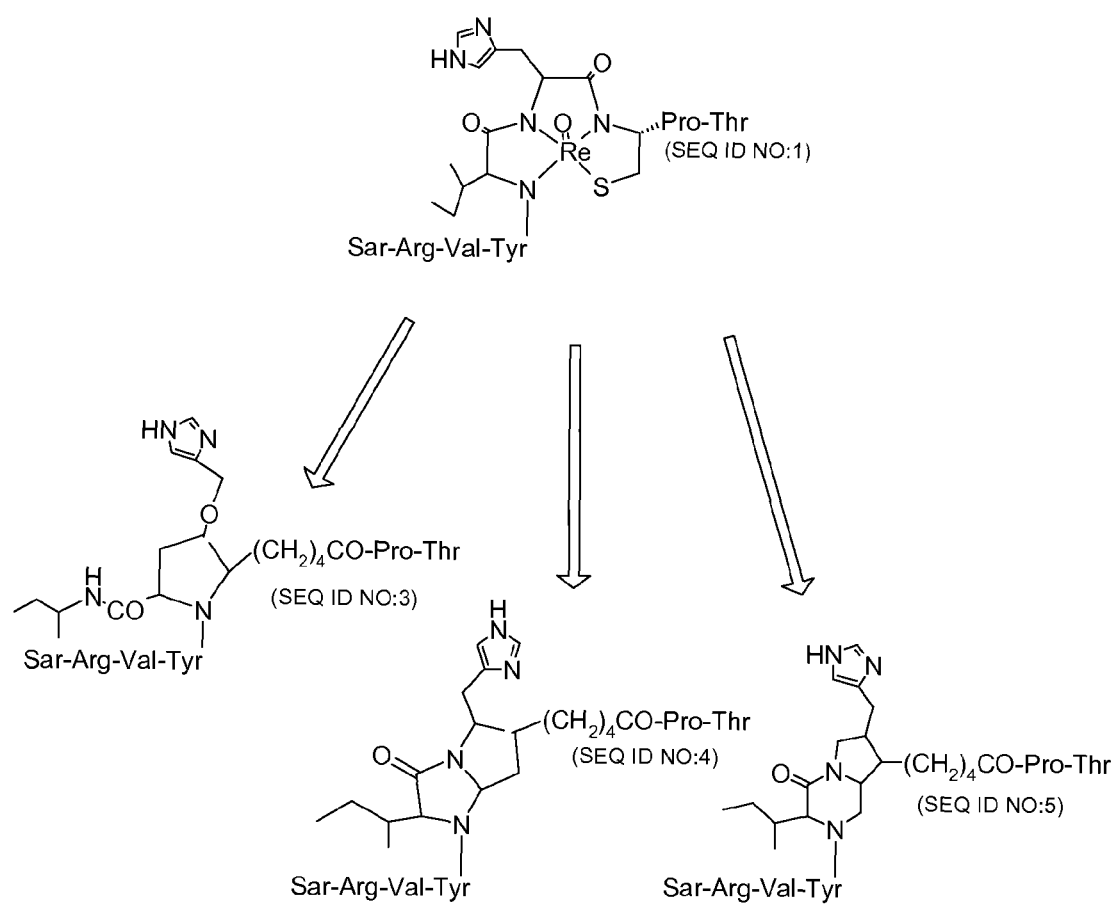
FIG. 3 depicts a scheme of this invention for deriving biologically active peptidomimetics from a metallopeptide specific for an angiotensin receptor, wherein Re depicts a rhenium metal ion.

As shown in FIG. 3, the Re-complexed angiotensin receptor-specific peptide Sar-Arg-Val-Tyr-Ile-His-Cys-Pro-Thr (SEQ ID NO:1) is utilized to derive ring structures. The peptide was synthesized and rhenium complexed as in Example 1. The metallopeptide was derived from a discrete library of peptides developed based on the known angiotensin ligand Sar-Arg-Val-Tyr-Ile-His-Pro-Thr (SEQ ID NO:2), wherein Sar is sarcosine, which served as the parent peptide, as is set forth more fully in International Patent Application Serial No. PCT/US01/50075, entitled Identification of Target-Specific Folding Sites in Peptides and Proteins, filed Dec. 19, 2001, incorporated here by reference. The metallopeptide was screened for binding to the angiotensin-II receptor using cell membranes obtained from human neuroblastoma cells (KAN-TS). The assay was performed in triplicates, using a radioiodinated tracer ligand. A final 1-3 nM concentration of $^{125}$I-Tyr$^4$, Sar$^1$, Ile$^8$-Angiotensin II ligand (obtained from Perkin Elemer—NEN Life Sciences) was used as radiotracer and angiotensin-II (1 µM final assay concentration) was used to measure non-specific binding. After filtration of the incubation medium, followed by washings, drying the filters and punching the filters into test tubes, the filters were counted for radioactivity in a gamma counter. An activity profile for test compounds was generated by ability to inhibit specific binding of the radiotracer to its receptor. In this assay, the metallopeptide exhibited 60% inhibition at 1 µM.

Derived ring structures based on the metallopeptide include:

(SEQ ID NO: 3)

(SEQ ID NO: 4)

(SEQ ID NO: 5)

EXAMPLE 185

Vasopressin Metallopeptide Derived Ring Compounds

Figure 4:
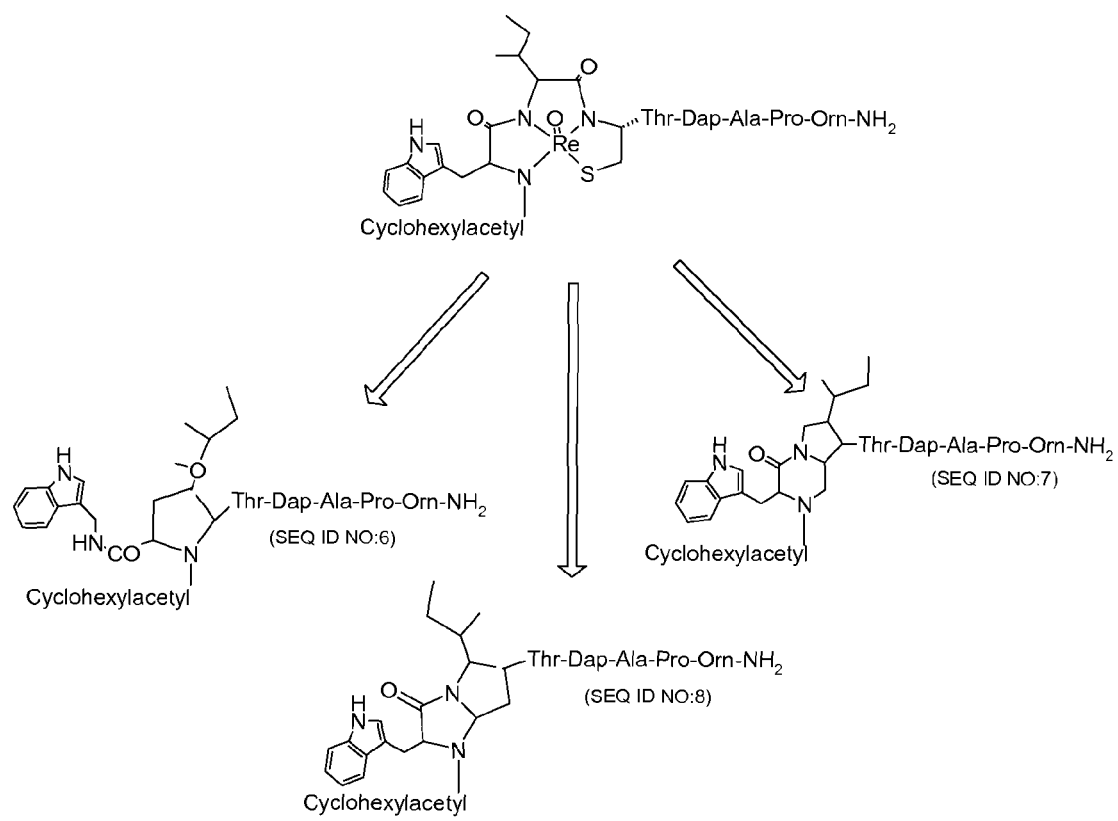
FIG. 4 depicts a scheme of this invention for deriving biologically active peptidomimetics from a metallopeptide specific for a vasopressin receptor, wherein Re depicts a rhenium metal ion.

As shown in FIG. 4, the Re-complexed vasopressin receptor-specific peptide Cyclohexylacetyl-D-Trp-Ile-Cys-Thr-Dap-Ala-Pro-Orn-NH$_2$ is utilized to derive ring structures.

The metallopeptide was selected from a discrete library of peptides developed based on the known vasopressin ligand Pmp-D-Trp-Ile-Thr-Dap-Cys-Pro-Orn, wherein Pmp is β-mercapto-β, β-cyclopentamethylenepropionyl and Dap is diaminopropionic acid, as is set forth more fully in International Patent Application Serial No. PCT/US01/50075, entitled Identification of Target-Specific Folding Sites in Peptides and Proteins, filed Dec. 19, 2001, incorporated here by reference. The peptides were made as described generally in Example 1, and were complexed with rhenium as described therein. The screening of compounds for vasopressin-1 receptor was performed using cell membranes prepared from rat liver. The assay was essentially performed as described for the oxytocin receptor assay in the following example. In this assay 2-4 nM $^3$H-vasopressin-1 antagonist (obtained from Perkin Elemer—NEN Life Sciences) was used as the radiotracer and Arg$^8$-vasopressin (1 µM final concentration in the assay) was used to determine non-specific binding. The assay was performed in triplicates. Activity profile for the test compounds was generated by their ability to inhibit specific binding of the radiotracer to its receptor. In this assay, the metallopeptide exhibited 52% inhibition at 1 µM.

Derived ring structures based on the metallopeptide include:

(SEQ ID NO: 6)

(SEQ ID NO: 7)

(SEQ ID NO: 8)

Figure 5:
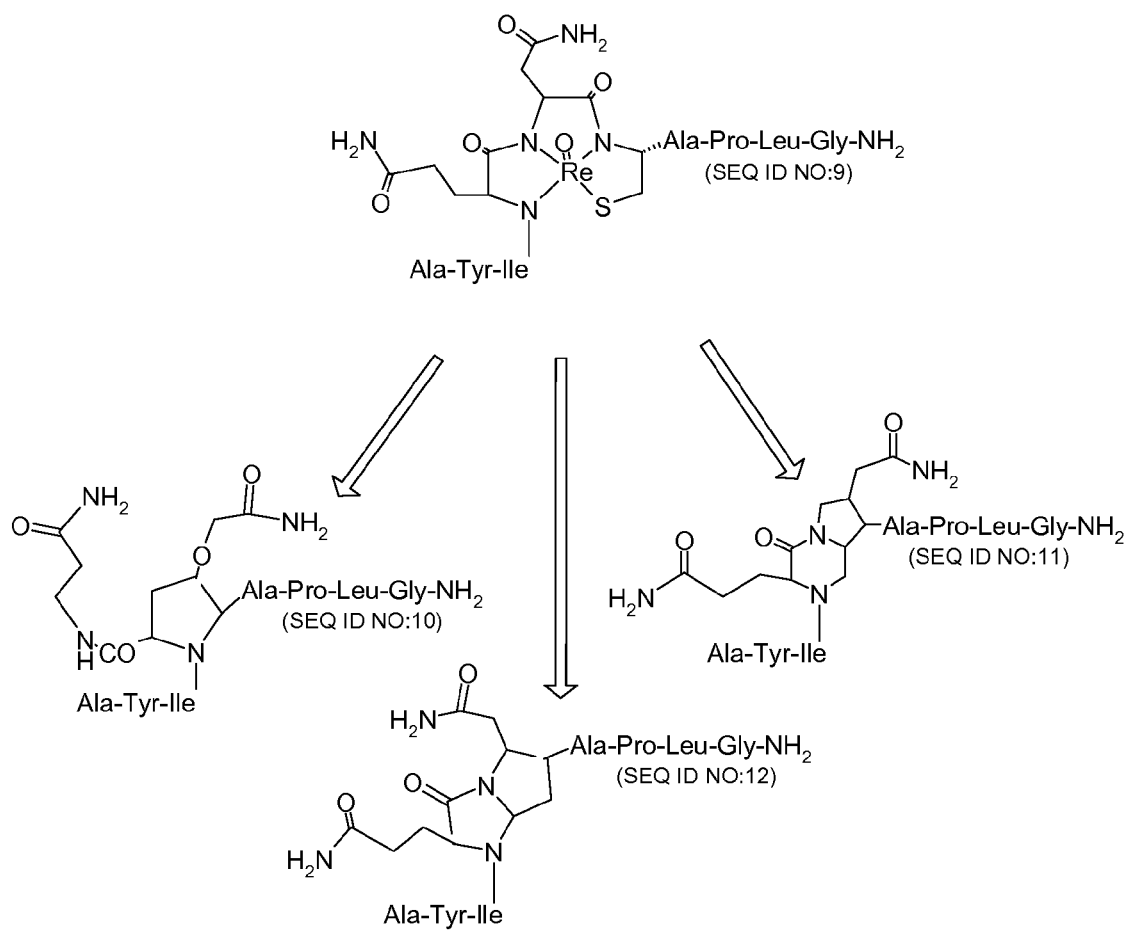
FIG. 5 depicts a scheme of this invention for deriving biologically active peptidomimetics from a metallopeptide specific for an oxytocin receptor, wherein Re depicts a rhenium metal ion.

As shown in FIG. 5, the Re-complexed oxytocin receptor-specific peptide Ala-Tyr-Ile-Gln-Asn-Cys-Ala-Pro-Leu-Gly-NH$_2$ (SEQ ID NO:9) is utilized to derive ring structures. The peptide was synthesized and rhenium complexed as in Example 1. Binding of the metallopeptide to oxytocin receptor was determined using cell membranes prepared from rat uterus. A Millipore Multi-Screen System was used for the assay, and was performed in 96-well Millipore filter plates (Durapore, 0.45 μm porosity) freshly blocked with 0.5% bovine serum albumin in phosphate buffered saline (PBS). The membrane preparations (10-50 μg/well) were incubated with 412-800 pM $^3$H-oxytocin in HEPES Buffer containing 0.2% bovine serum albumin along with a test compound (1 μM final assay concentration) for 2 hours at 4° C. Non-specific binding was determined by addition of $10^{-6}$ M oxytocin instead of the test compound. After incubation, the membranes were filtered and washed three times with ice-cold PBS. The membranes were air-dried and punched directly into scintillation vials. After addition of the scintillation cocktail, the vials were capped and gently shaken for 12 hours to dissolve the radioactivity contained in the filters. The vials were then read for tritium counts in a scintillation counter. Specific binding was determined as the radioactivity in wells containing $^3$H-oxytocin alone minus the radioactivity in wells containing $10^{-6}$ M oxytocin. The assay was performed in triplicates. The activity profile for the test compounds was generated by their ability to inhibit specific binding of the radiotracer to its receptor. In this assay, the metallopeptide exhibited 42% inhibition at 1 μM.

EXAMPLE 186

Oxytocin Metallopeptide Derived Ring Compounds

As shown in FIG. 5, the Re-complexed oxytocin receptor-specific peptide Ala-Tyr-Ile-Gln-Asn-Cys-Ala-Pro-Leu-Gly-NH$_2$ is utilized to derive ring structures. The peptide was synthesized and rhenium complexed as in Example 1. Binding of the metallopeptide to oxytocin receptor was determined using cell membranes prepared from rat uterus. A Millipore Multi-Screen System was used for the assay, and was performed in 96-well Millipore filter plates (Durapore, 0.45 μm porosity) freshly blocked with 0.5% bovine serum albumin in phosphate buffered saline (PBS). The membrane preparations (10-50 μg/well) were incubated with 412-800 pM $^3$H-oxytocin in HEPES Buffer containing 0.2% bovine serum albumin along with a test compound (1 μM final assay concentration) for 2 hours at 4° C. Non-specific binding was determined by addition of $10^{-6}$ M oxytocin instead of the test compound. After incubation, the membranes were filtered and washed three times with ice-cold PBS. The membranes were air-dried and punched directly into scintillation vials. After addition of the scintillation cocktail, the vials were capped and gently shaken for 12 hours to dissolve the radioactivity contained in the filters. The vials were then read for tritium counts in a scintillation counter. Specific binding was determined as the radioactivity in wells containing $^3$H-oxytocin alone minus the radioactivity in wells containing $10^{-6}$ M oxytocin. The assay was performed in triplicates. The activity profile for the test compounds was generated by their ability to inhibit specific binding of the radiotracer to its receptor. In this assay, the metallopeptide exhibited 42% inhibition at 1 μM.

Derived ring structures based on the metallopeptide include:

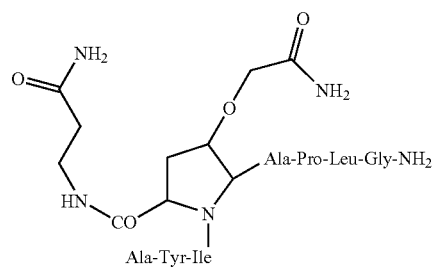
(SEQ ID NO: 10)

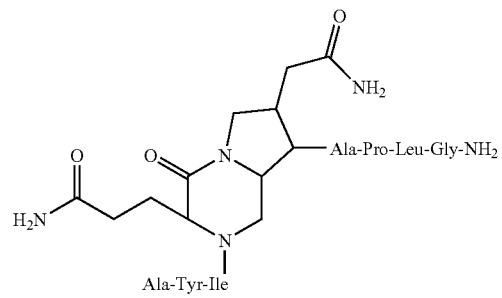
(SEQ ID NO: 11)

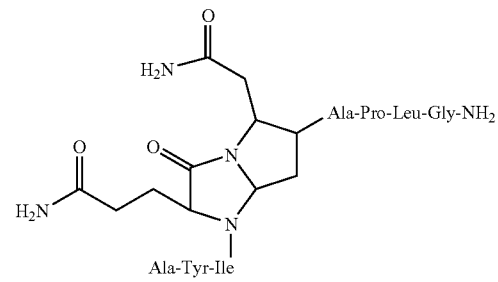
(SEQ ID NO: 12)

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A peptidomimetic of the formula:

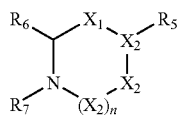

wherein $X_1$ is $(CH_2)_m$;

$X_2$ bearing the $R_5$ substituent is N and all other $X_2$ are $CH_2$;

$R_5$ is

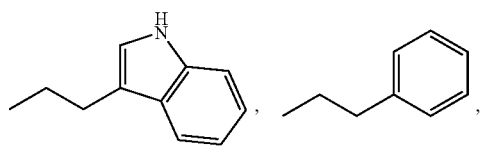

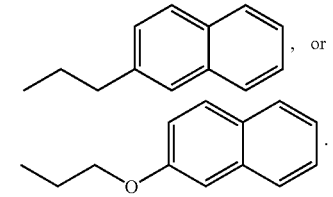

$R_6$ is —$(CH_2)_4NH_2$, —$(CH_2)_3NHC(NH_2)$=NH, —$(CH_2)_3NHCOCH_3$, —$(CH_2)_3NHCOOCH_3$, —$(CH_2)_2NHC(NH_2)$=NH, —$(CH_2)_2NHCONH_2$, —$(CH_2)_4NHCOH$, —$(CH_2)_4NHCOCH_3$, —$(CH_2)_3NHCONHCH_3$, —$(CH_2)_3NHSO_2NH_2$, —$(CH_2)_3NHSO_2CH_3$, —$(CH_2)_3NH_2$, —$(CH_2)_2CONH_2$, —$(CH_2)_3NH(C$=NH$)NHMe$, —$(CH_2)_3NH(C$=NH$)NHEt$, —$(CH_2)_3NH(C$=NH$)NHPr$, —$(CH_2)_3NH(C$=NH$)NHPr$-i, —$(CH_2)_3NH(C$=NH$)NH_2$, —$(CH_2)_4NHCONH_2$, —$(CH_2)_4NH(C$=NH$)NH_2$,

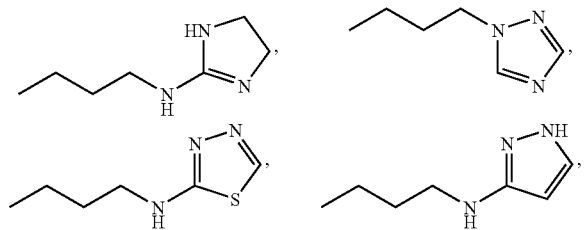

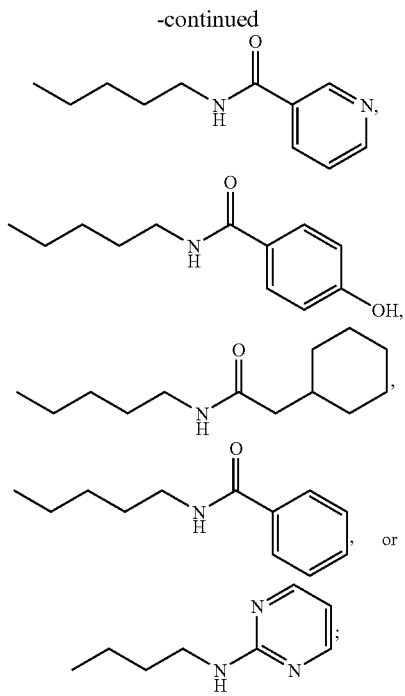

$R_7$ is $R_9$-$R_8$-;

$R_8$ is an L- or D-configuration of Phe, Phe(2-Cl), Phe(4-Cl), Phe(2,4-diCl), Phe(3,4-diCl), Phe(4-NO_2), Phe(4-Me), Phe(4-Phenyl), HPhe, Phg, Trp, Nal 1, Nal 2, Bip, Dip, Bpa, Ser(Bzl), Lys(Z), Lys(Z-2'Br), Lys(Bz), Thr(Bzl), Cys(Bzl), Tyr(BzlCl_2), pF-Phe, Phe(4-Br), Phe(4-CF_3), Phe(3,4-diF), Phe(4-I) or Phe(3,4-di-OMe);

$R_9$ is optionally not present or is an L- or D-configuration of H is, Ser(Bzl), Tic, heptanoyl-Ser(Bzl), hexanoyl-Ser(Bzl), Hyp(Bzl), 4-phenylPro, 5-phenylPro, Tiq, Atc, Igl, Hyp(O-2-Naphthyl), Hyp(O-Phenyl), 2-Aic, Idc, 1-Aic, NH_2(CH_2)_6CO—, Benzyl, Beta-homoSer(Bzl), Ser(O-2-Naphthyl), Ser(O-Phenyl), Ser(O-4-Cl-Phenyl), Ser(O-2-Cl-Phenyl), Thr(Bzl), Tic, heptanoyl-Thr(Bzl), hexanoyl-Thr(Bzl), Beta-homoThr(Bzl), Thr(O-2-Naphthyl), Thr(O-Phenyl), Thr(O-4-Cl-Phenyl) or Thr(O-2-Cl-Phenyl);

n is 1; and mist.

2. A pharmaceutical composition comprising the peptidomimetic of claim 1 and a pharmaceutically acceptable carrier.

* * * * *

UNITED STATES PATENT AND TRADEMARK OFFICE
CERTIFICATE OF CORRECTION

PATENT NO. : 7,807,678 B2  
APPLICATION NO. : 10/776419  
DATED : October 5, 2010  
INVENTOR(S) : Shubh D. Sharma et al.

Page 1 of 1

It is certified that error appears in the above-identified patent and that said Letters Patent is hereby corrected as shown below:

Claim 1, Column 156, line 53, replace "H is," with --His--.

Claim 1, Column 156, line 63, replace "mist." with --m is 1.--.

Signed and Sealed this  
Twenty-eighth Day of December, 2010

David J. Kappos  
*Director of the United States Patent and Trademark Office*

SEQUENCE LISTING

<160> NUMBER OF SEQ ID NOS: 12

<210> SEQ ID NO 1
<211> LENGTH: 9
<212> TYPE: PRT
<213> ORGANISM: Artificial

```
<220> FEATURE:
<223> OTHER INFORMATION: Angiotensin receptor-specific metallopeptide
<220> FEATURE:
<221> NAME/KEY: MISC_FEATURE
<222> LOCATION: (1)..(1)
<223> OTHER INFORMATION: Xaa is sarcosine
<220> FEATURE:
<221> NAME/KEY: METAL
<222> LOCATION: (5)..(7)
<223> OTHER INFORMATION: metal binding sequence

<400> SEQUENCE: 1

Xaa Arg Val Tyr Ile His Cys Pro Thr
1               5

<210> SEQ ID NO 2
<211> LENGTH: 8
<212> TYPE: PRT
<213> ORGANISM: Artificial
<220> FEATURE:
<223> OTHER INFORMATION: Artificial angiotensin ligand
<220> FEATURE:
<221> NAME/KEY: MISC_FEATURE
<222> LOCATION: (1)..(1)
<223> OTHER INFORMATION: Xaa is sarcosine

<400> SEQUENCE: 2

Xaa Arg Val Tyr Ile His Pro Thr
1               5

<210> SEQ ID NO 3
<211> LENGTH: 7
<212> TYPE: PRT
<213> ORGANISM: Artificial
<220> FEATURE:
<223> OTHER INFORMATION: Angiotensin receptor-specific construct
<220> FEATURE:
<221> NAME/KEY: MISC_FEATURE
<222> LOCATION: (1)..(1)
<223> OTHER INFORMATION: Xaa is sarcosine
<220> FEATURE:
<221> NAME/KEY: MISC_FEATURE
<222> LOCATION: (5)..(5)
<223> OTHER INFORMATION: Xaa is pyrrolidine core small molecule

<400> SEQUENCE: 3

Xaa Arg Val Tyr Xaa Pro Thr
1               5

<210> SEQ ID NO 4
<211> LENGTH: 7
<212> TYPE: PRT
<213> ORGANISM: Artificial
<220> FEATURE:
<223> OTHER INFORMATION: Angiotensin receptor-specific construct
<220> FEATURE:
<221> NAME/KEY: MISC_FEATURE
<222> LOCATION: (1)..(1)
<223> OTHER INFORMATION: Xaa is sarcosine
<220> FEATURE:
<221> NAME/KEY: MISC_FEATURE
<222> LOCATION: (5)..(5)
<223> OTHER INFORMATION: Xaa is hexahydro-pyrrolo[1,2-a]imidazol-3-one
      core small molecule

<400> SEQUENCE: 4

Xaa Arg Val Tyr Xaa Pro Thr
1               5
```

```
<210> SEQ ID NO 5
<211> LENGTH: 7
<212> TYPE: PRT
<213> ORGANISM: Artificial
<220> FEATURE:
<223> OTHER INFORMATION: Angiotensin receptor-specific construct
<220> FEATURE:
<221> NAME/KEY: MISC_FEATURE
<222> LOCATION: (1)..(1)
<223> OTHER INFORMATION: Xaa is sarcosine
<220> FEATURE:
<221> NAME/KEY: MISC_FEATURE
<222> LOCATION: (5)..(5)
<223> OTHER INFORMATION: Xaa is hexahydro-pyrrolo[1,2-a]pyrazin-4-one
      core small molecule

<400> SEQUENCE: 5

Xaa Arg Val Tyr Xaa Pro Thr
1               5

<210> SEQ ID NO 6
<211> LENGTH: 7
<212> TYPE: PRT
<213> ORGANISM: Artificial
<220> FEATURE:
<223> OTHER INFORMATION: Vasopressin receptor-specific construct
<220> FEATURE:
<221> NAME/KEY: MISC_FEATURE
<222> LOCATION: (1)..(1)
<223> OTHER INFORMATION: Xaa is cyclohexylacetyl
<220> FEATURE:
<221> NAME/KEY: MISC_FEATURE
<222> LOCATION: (2)..(2)
<223> OTHER INFORMATION: Xaa is pyrrolidine core small molecule
<220> FEATURE:
<221> NAME/KEY: MISC_FEATURE
<222> LOCATION: (4)..(4)
<223> OTHER INFORMATION: Xaa is diaminoproprionic acid
<220> FEATURE:
<221> NAME/KEY: MISC_FEATURE
<222> LOCATION: (7)..(7)
<223> OTHER INFORMATION: Xaa is ornithine

<400> SEQUENCE: 6

Xaa Xaa Thr Xaa Ala Pro Xaa
1               5

<210> SEQ ID NO 7
<211> LENGTH: 7
<212> TYPE: PRT
<213> ORGANISM: Artificial
<220> FEATURE:
<223> OTHER INFORMATION: Vasopressin receptor-specific construct
<220> FEATURE:
<221> NAME/KEY: MISC_FEATURE
<222> LOCATION: (1)..(1)
<223> OTHER INFORMATION: Xaa is cyclohexylacetyl
<220> FEATURE:
<221> NAME/KEY: MISC_FEATURE
<222> LOCATION: (2)..(2)
<223> OTHER INFORMATION: Xaa is hexahydro-pyrrolo[1,2-a]pyrazin-4-one
      core small molecule
<220> FEATURE:
<221> NAME/KEY: MISC_FEATURE
<222> LOCATION: (4)..(4)
<223> OTHER INFORMATION: Xaa is diaminoproprionic acid
<220> FEATURE:
<221> NAME/KEY: MISC_FEATURE
<222> LOCATION: (7)..(7)
<223> OTHER INFORMATION: Xaa is ornithine

<400> SEQUENCE: 7

Xaa Xaa Thr Xaa Ala Pro Xaa
1               5
```

```
<210> SEQ ID NO 8
<211> LENGTH: 7
<212> TYPE: PRT
<213> ORGANISM: Artificial
<220> FEATURE:
<223> OTHER INFORMATION: Vaspressin receptor-specific construct
<220> FEATURE:
<221> NAME/KEY: MISC_FEATURE
<222> LOCATION: (1)..(1)
<223> OTHER INFORMATION: Xaa is cyclohexylacetyl
<220> FEATURE:
<221> NAME/KEY: MISC_FEATURE
<222> LOCATION: (2)..(2)
<223> OTHER INFORMATION: Xaa is hexahydro-pyrrolo[1,2-a]imidazol-3-one
      core small molecule
<220> FEATURE:
<221> NAME/KEY: MISC_FEATURE
<222> LOCATION: (4)..(4)
<223> OTHER INFORMATION: Xaa is diaminoproprionic acid
<220> FEATURE:
<221> NAME/KEY: MISC_FEATURE
<222> LOCATION: (7)..(7)
<223> OTHER INFORMATION: Xaa is ornithine

<400> SEQUENCE: 8

Xaa Xaa Thr Xaa Ala Pro Xaa
1               5

<210> SEQ ID NO 9
<211> LENGTH: 10
<212> TYPE: PRT
<213> ORGANISM: Artificial
<220> FEATURE:
<223> OTHER INFORMATION: Oxytocin receptor-specific metallopeptide
<220> FEATURE:
<221> NAME/KEY: METAL
<222> LOCATION: (4)..(6)
<223> OTHER INFORMATION: metal binding sequence

<400> SEQUENCE: 9

Ala Tyr Ile Glx Asx Cys Ala Pro Leu Gly
1               5                   10

<210> SEQ ID NO 10
<211> LENGTH: 8
<212> TYPE: PRT
<213> ORGANISM: Artificial
<220> FEATURE:
<223> OTHER INFORMATION: Oxytocin receptor-specific construct
<220> FEATURE:
<221> NAME/KEY: MISC_FEATURE
<222> LOCATION: (4)..(4)
<223> OTHER INFORMATION: Xaa is pyrrolidine core small molecule

<400> SEQUENCE: 10

Ala Tyr Ile Xaa Ala Pro Leu Gly
1               5

<210> SEQ ID NO 11
<211> LENGTH: 8
<212> TYPE: PRT
<213> ORGANISM: Artificial
<220> FEATURE:
<223> OTHER INFORMATION: Oxytocin receptor-specific construct
<220> FEATURE:
<221> NAME/KEY: MISC_FEATURE
<222> LOCATION: (4)..(4)
<223> OTHER INFORMATION: Xaa is Hexahydro-pyrrolo[1,2-a]pyrazin-4-one

<400> SEQUENCE: 11

Ala Tyr Ile Xaa Ala Pro Leu Gly
1               5
```

```
<210> SEQ ID NO 12
<211> LENGTH: 8
<212> TYPE: PRT
<213> ORGANISM: Artificial
<220> FEATURE:
<223> OTHER INFORMATION: Oxytocin receptor-specific construct
<220> FEATURE:
<221> NAME/KEY: MISC_FEATURE
<222> LOCATION: (4)..(4)
<223> OTHER INFORMATION: Xaa is hexahydro-pyrrolo[1,2-a]imidazol-3-one

<400> SEQUENCE: 12

Ala Tyr Ile Xaa Ala Pro Leu Gly
1               5
```